(12) United States Patent
Brown et al.

(10) Patent No.: US 7,241,810 B2
(45) Date of Patent: Jul. 10, 2007

(54) FORMAMIDE DERIVATIVES FOR THE TREATMENT OF DISEASES

(75) Inventors: Alan Daniel Brown, Sandwich (GB); Mark Edward Bunnage, Sandwich (GB); Charlotte Alice Louise Lane, Sandwich (GB); Russell Andrew Lewthwaite, Sandwich (GB); Paul Alan Glossop, Sandwich (GB); Kim James, Sandwich (GB); David Anthony Price, Sandwich (GB)

(73) Assignee: Pfizer Inc, New York, NY (US)

( * ) Notice: Subject to any disclaimer, the term of this patent is extended or adjusted under 35 U.S.C. 154(b) by 297 days.

(21) Appl. No.: 11/086,035

(22) Filed: Mar. 21, 2005

(65) Prior Publication Data

US 2005/0215590 A1 Sep. 29, 2005

Related U.S. Application Data

(60) Provisional application No. 60/642,275, filed on Jan. 7, 2005, provisional application No. 60/591,777, filed on Jul. 27, 2004.

(30) Foreign Application Priority Data

Mar. 23, 2004 (EP) .................................. 04290767
Nov. 12, 2004 (GB) .................................. 0425054.4

(51) Int. Cl.
*A61K 31/167* (2006.01)
*C07C 233/24* (2006.01)

(52) U.S. Cl. ...................... 514/616; 564/158; 564/165; 546/111; 546/146; 546/226; 546/337; 549/28; 514/290; 514/307; 514/330; 514/357; 514/432

(58) Field of Classification Search ................ 514/616, 514/432, 290, 307, 330, 357; 564/158, 165; 549/28; 546/111, 146, 226, 337
See application file for complete search history.

(56) References Cited

U.S. PATENT DOCUMENTS 4,478,849 A   10/1984   Ainsworth et al. ......... 424/285
6,106,864 A   8/2000   Dolan et al. ................. 424/488
2002/0026065 A1   2/2002   Sher et al. ................... 558/166
2003/0229058 A1   12/2003   Moran et al. ............... 514/171
2004/0006112 A1   1/2004   Orchard et al. ............. 514/342

FOREIGN PATENT DOCUMENTS

WO   WO 9111172   8/1991
WO   WO 9402518   2/1994
WO   WO 9855148   12/1998
WO   WO 0035298   6/2000

OTHER PUBLICATIONS

Barnes, P. J. Chest, 111:2, pp. 17S-26S (1997).
Bryan, S.A. et al., Expert Opinion on Investigational Drugs, 9:1, pp. 25-42 (2000).
Haleblian, J. Pharm Sci, 64(8), pp. 1269-1288 (1975).
Liang and Chen, Expert Opinion in Therapeutic Patents, 11(6), pp. 981-986 (2001).
Finnin and Morgan, J. Pharm. Sci. 88(10), pp. 955-958 (1999).

*Primary Examiner*—Charanjit S. Aulakh
(74) *Attorney, Agent, or Firm*—Gregg C. Benson; Robert T. Ronau

(57) ABSTRACT

The invention relates to compounds of formula (1)

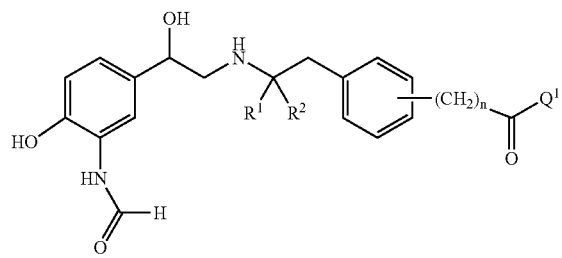

(1)

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

15 Claims, No Drawings

FORMAMIDE DERIVATIVES FOR THE TREATMENT OF DISEASES

This invention relates to β2 agonists of general formula:

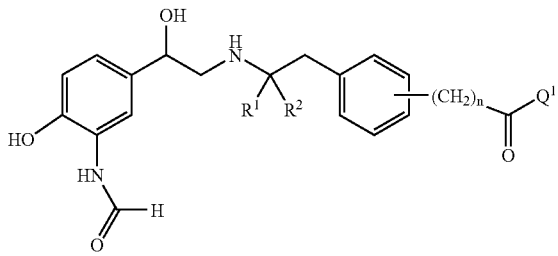

(1)

in which $R^1$, $R^2$, n and $Q^1$ have the meanings indicated below, and to processes for the preparation of, compositions containing and the uses of such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S–26S and Bryan, S. A. et al, Expert Opinion on investigational drugs, 2000, 9:1, pp 25–42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel $β_2$ agonists that would have an appropriate pharmacological profile, for example in terms of potency, selectivity, pharmacokinetics or duration of action. In this context, the present invention relates to novel β2 agonists.

Various formamide derivatives have already been disclosed. For example, US2004/0006112 discloses compounds active as β2 agonist, of formula:

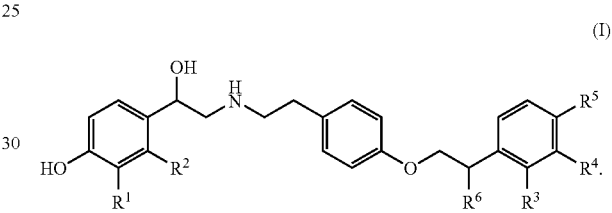

(I)

US2003/0229058 discloses selective β2 agonists of formula:

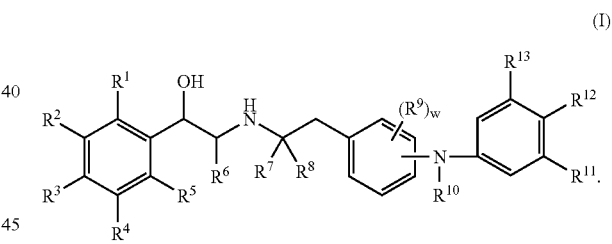

(I)

However, none of the above formamide derivative have shown a pharmacological profile allowing them to be used as efficient drugs in the treatment of β2-mediated diseases and/or conditions, such as allergic and non-allergic airways diseases; in particular by the inhalation route.

The invention relates to the compounds of general formula (1):

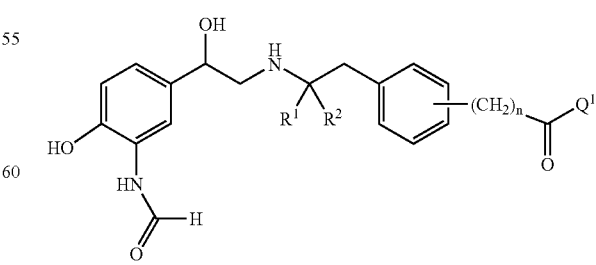

(1)

wherein the $(CH_2)_n$—$C(=O)Q^1$ group is in the meta or para position, $R^1$ and $R^2$ are independently selected from H and $C_1$–$C_4$ alkyl;

n is 0, 1 or 2;

$Q^1$ is a group selected from,

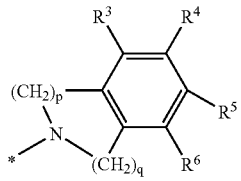

wherein p is 1 or 2 and q is 1 or 2, said group being optionally bridged by one carbon atom,

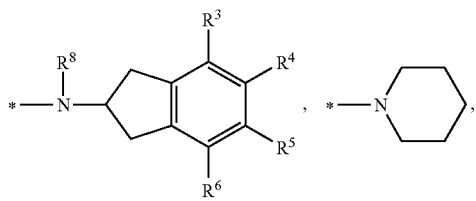

and a group *—$NR^8$-$Q^2$-A, wherein $Q^2$ is a $C_1$–$C_4$ alkylene, $R^8$ is H or $C_1$–$C_4$ alkyl and A is pyridyl, $C_3$–$C_{10}$ cycloalkyl, said cycloalkyl being optionally bridged by one or more, preferably 1, 2, 3 or 4, carbon atoms, tetrahydropyranyl, piperidinyl, tetrahydrothiopyranyl or a group

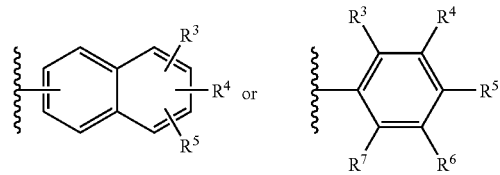

$R^3$, $R^4$, $R^5$, $R^6$ and $R^7$ are the same or different and are selected from H, $C_1$–$C_4$ alkyl, $OR^9$, $SR^9$, $SOR^9$, $SO_2R^9$, halo, CN, $CO_2R^9$, $CF_3$, $OCF_3$, $SO_2NR^9R^{10}$, $CONR^9R^{10}$, $NR^9R^{10}$, $NHCOR^{10}$ and phenyl optionally substituted with 1 to 3 groups selected from $OR^9$, halo and $C_1$–$C_4$ alkyl;

—$R^9$ and $R^{10}$ are the same or different and are selected from H or $C_1$–$C_4$ alkyl and the * represent the attachment point to the carbonyl group;

or, if appropriate, their pharmaceutically acceptable salts and/or isomers, tautomers, solvates or isotopic variations thereof.

The compounds of formula (1) are agonists of the β2 receptors, that are particularly useful for the treatment of β2-mediated diseases and/or conditions, by showing excellent potency, in particular when administered via the inhalation route.

In the here above general formula (1), $C_1$–$C_4$ alkyl and $C_1$–$C_4$ alkylene denote a straight-chain or branched group containing 1, 2, 3 or 4 carbon atoms. This also applies if they carry substituents or occur as substituents of other radicals, for example in O—($C_1$–$C_4$)alkyl radicals, S—($C_1$–$C_4$)alkyl radicals etc. . . . Examples of suitable ($C_1$–$C_4$)alkyl radicals are methyl, ethyl, n-propyl, iso-propyl, n-butyl, iso-butyl, sec-butyl, tert-butyl . . . . Examples of suitable O—($C_1$–$C_4$) alkyl radicals are methoxy, ethoxy, n-propyloxy, isopropyloxy, n-butyloxy, iso-butyloxy, sec-butyloxy and tert-butyloxy . . . .

The $C_3$–$C_{10}$ cycloalkyl wherein 2 carbon atoms or more are optionally bridged by one or more carbon atoms include cyclopropyl, cyclobutyl, cyclopentyl, cyclohexyl and cycloheptyl, adamantyl, bicyclo[3.1.1]heptane, bicyclo[2.2.1] heptane, bicyclo[2.2.2]octane. Preferred cycloalkyl groups are cyclohexyl and adamantyl.

Finally, halo denotes a halogen atom selected from the group consisting of fluoro, chloro, bromo and iodo in particular fluoro or chloro.

In the following, the free bond on the phenyl group such as in the structure below,

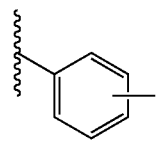

means that the phenyl can be substituted in the meta or para position. The compounds of the formula (1)

(1)

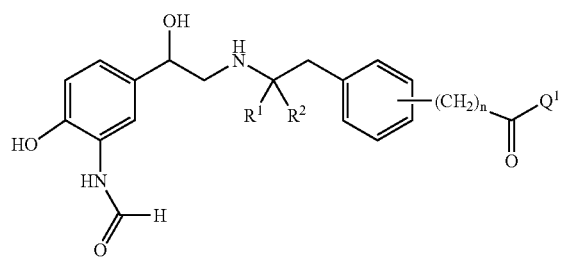

can be prepared using conventional procedures such as by the following illustrative methods in which $Q^1$, $Q^2$, $R^1$, $R^2$, A and n are as previously defined for the compounds of the formula (1) unless otherwise stated.

The amide derivatives of the formula (1) may be prepared by coupling an acid of formula (2):

(2)

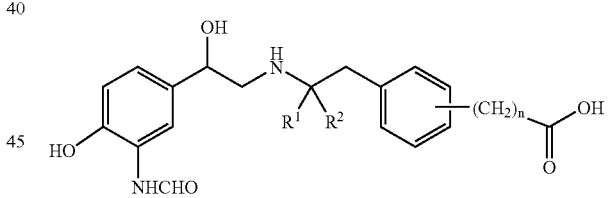

with an amine of formula $NHR^8$-$Q^2$-A (3), (3')

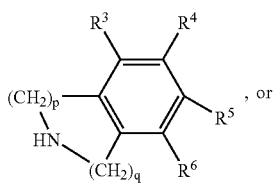

, or (3")

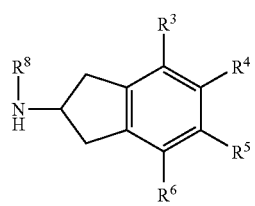

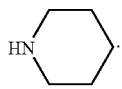
(3''')

The coupling is generally carried out in an excess of said amine as an acid receptor, with a conventional coupling agent (e.g. 1-(3-dimethylaminopropyl)-3-ethylcarbodiimide hydrochloride, N,N'-dicyclohexylcarbodiimide or O—(1H-benzotriazol-1-yl)-N,N,N',N'-tetramethyluronium hexafluorophosphate), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane or ethyl acetate, and at temperature comprised between 10° C. and 40° C. (room temperature) for a period of 1–24 hours.

Said amine (3), (3'), (3") or (3''') is either commercially available or may be prepared by conventional methods well known to the one skilled in the art (e.g. reduction, oxidation, alkylation, transition metal-mediated coupling, protection, deprotection etc. . .) from commercially available material.

The acid of formula (2) may be prepared from the corresponding ester of formula (4):

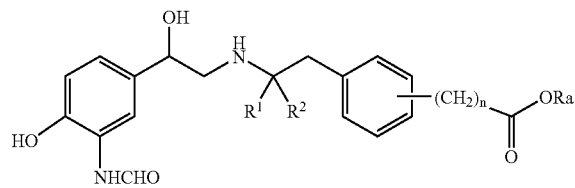
(4)

wherein Ra is a suitable acid protecting group, preferably a benzyl group or a ($C_1$–$C_4$) alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours. Alternatively, if the ester is a benzyl group, the ester may be hydrogenated in the presence of a suitable catalyst (e.g. palladium-on-carbon, or palladium hydroxide-on-carbon) in a suitable solvent such (methanol, ethanol, 2M ammonia in methanol) at a temperature comprised between 20° C. and 50° C. for 1–48 h at 1–4 atmospheres of hydrogen.

The ester of formula (4) may be prepared by reaction of an amine of formula (5):

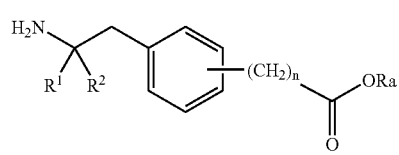
(5)

wherein Ra and n are as previously defined, with a bromide of formula (6):

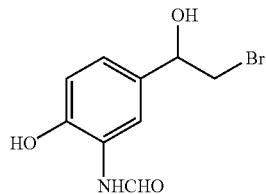
(6)

In a typical procedure, the amine of formula (5) is reacted with a bromide of formula (6) optionally in the presence of a solvent or mixture of solvents (e.g. dimethylsulfoxide, toluene, N, N-dimethylformamide, acetonitrile), optionally in the presence of a suitable base (e.g. triethylamine, diisopropylethylamine, potassium carbonate) at a temperature comprised between 80° C. and 120° C., for 12 to 48 hours.

The bromide of formula (6) may be prepared according to the method disclosed in "Organic Process Research and Development 1998, 2, 96–99".

The amine of formula (5), where $R^1$ is Me and $R^2$ is H, may be prepared as either the (R) or (S) enantiomer from the corresponding protected amine of formula (7):

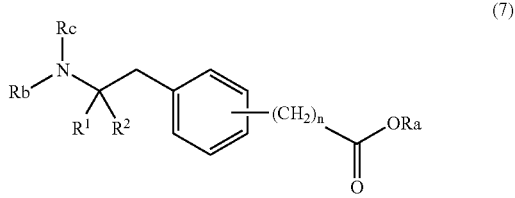
(7)

wherein Ra and n are as previously defined and Rb and Rc represent any suitable substituents so that HNRbRc is a chiral amine (for example, Rb may be hydrogen and Rc may be α-methylbenzyl), provided that the bonds between N and Rb and N and Rc can be easily cleaved to give the free amine of formula (5) using standard methodology for cleaving nitrogen protecting groups, such as those found in the text book Protective Groups in Organic Synthesis Third Edition by T. W. Greene and P. G. M. Wuts, John Wiley and Sons Inc., 1999.

The amine of formula (7) may be prepared as a single diastereomer by reaction of an amine of formula HNRbRc with a ketone of formula (8):

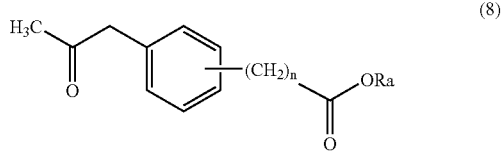
(8)

wherein Ra, Rb, Rc and n are as previously defined.

In a typical procedure, the reaction of the ketone of formula (8) with the amine of formula HNRbRc leads to a chiral intermediate which is in turn reduced by a suitable reducing agent (e.g. sodium cyanoborohydride of formula NaCNBH$_3$ or sodium triacetoxyborohydride of formula Na(OAc)$_3$BH) optionally in the presence of a drying agent (e.g. molecular sieves, magnesium sulfate) and optionally in the presence of an acid catalyst (e.g. acetic acid) to give the amine of formula (7) as a mixture of diastereomers. The reaction is generally done in a solvent such as tetrahydrofuran or dichloromethane at a temperature comprised between 20° C. and 80° C. for 3 to 72 hours. The resulting product is then converted to the hydrochloride or nitrate salt and selectively crystallised from a suitable solvent or mixture of solvents (e.g. isopropanol, ethyl acetate, ethanol, methanol, diisopropyl ether or diisopropyl ether/methanol) to give (7) as a single diastereomer.

The ketone of formula (8) where n=1 may be prepared by palladium mediated coupling of an aryl halide of formula (9):

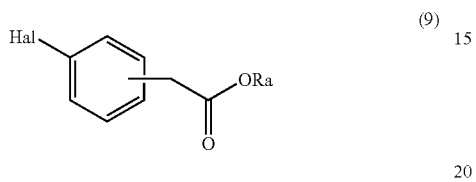

wherein Ra is as previously defined and Hal represents an halogen atom, which includes, but is not limited to bromo and iodo, with an enolate or enolate equivalent.

In a typical procedure, the aryl halide of formula (9) is reacted with a tin enolate generated in-situ by treatment of isopropenyl acetate with tri-n-butyltin methoxide of formula $Bu_3SnOMe$ in the presence of a suitable palladium catalyst (palladium acetate/tri-ortho-tolylphosphine of formula $Pd(OAc)_2/P(o-Tol)_3$) in a non-polar solvent (e.g. toluene, benzene, hexane). Preferably, the reaction is carried out at a temperature comprised between 80° C. and 110° C. for 6 to 16 hours.

The aryl halide of formula (9) may be obtained by esterification of the corresponding acid of formula (10):

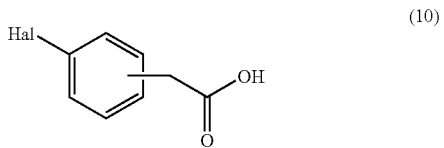

wherein Hal is as previously defined, according to any method well-known to the one skilled in the art to prepare an ester from an acid, without modifying the rest of the molecule.

In a typical procedure, the acid of formula (10) is reacted with an alcoholic solvent of formula RaOH, wherein Ra is as previously defined, in the presence of an acid such as hydrogen chloride at a temperature between 10° C. and 40° C. (room temperature) for 8 to 16 hours. Alternatively, the acid of formula (10) is reacted with a base (for example cesium or potassium carbonate) and treated with an alkyl halide (for example methyl iodide, benzyl bromide) in an appropriate solvent such as N,N-diemthylformamide at a temperature between 10° C. and 40° C. (room temperature) for 1 to 20 h.

The acid of formula (10) is a commercial product.

The amine of formula (5), where $R^1$ and $R^2$ are both $C_1$–$C_4$ alkyl, may be prepared according to the following scheme:

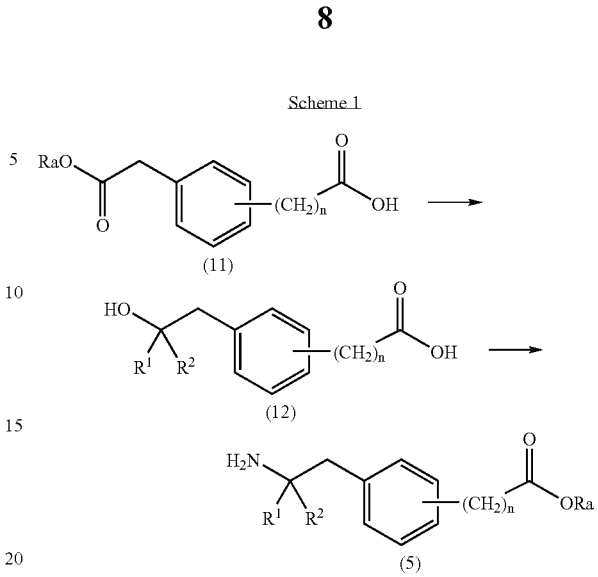

wherein $R^1$, $R^2$ and n are as previously defined.

In a typical procedure, the ester of formula (11) is reacted with an "activated" alkyl (organometallic alkyl such as $R^2MgBr$, $R^2MgCl$ or $R^2Li$) to give the corresponding tertiary alcohol of formula (12) using the method described above.

Said tertiary alcohol of formula (12) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting amino acid is then esterified using the method described herein to give the amine of formula (5).

Alternatively, the amine of formula (5), where $R^1$ are $R^2$ both $C_1$–$C_4$ alkyl and n=0, may be prepared according to the following scheme:

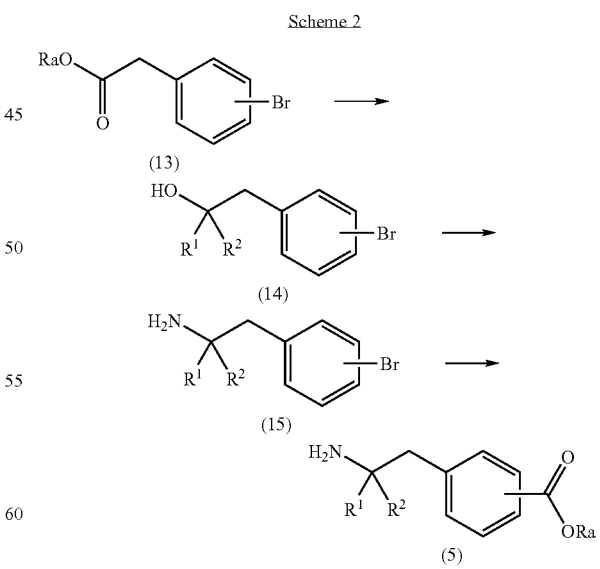

wherein $R^1$, $R^2$ and Ra are as previously defined.

In a typical procedure, the ester of formula (13) is reacted with an "activated" alkyl (organometallic alkyl such as $R^2MgBr$, $R^2MgCl$ or $R^2Li$) to give the corresponding tertiary alcohol of formula (14) using the method described above.

Said tertiary alcohol of formula (14) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks to give the bromo amine (15).

The resulting bromo amine (15) is treated with a suitable palladium catalyst (e.g. [1,1'-bis(diphenylphosphino)ferrocene]dichloropalladium(II), palladium(II) acetate 1,1'-bis (diphenylphosphino)ferrocene], tris(dibenzylideneacetone) dipalladium(0), 2,2'-bis(diphenylphosphino)-1,1'-binaphthyidichloropalladium(II)) under an atmosphere of carbon monoxide using RaOH as solvent (e.g. MeOH, EtOH, benzyl alcohol), or alternatively using a co-solvent such as DMF, at elevated temperature (100° C.) and pressure (100 psi) to give the ester of formula (5).

The ketone of formula (8) where n=2 may be prepared by reduction of an alkene of formula (16):

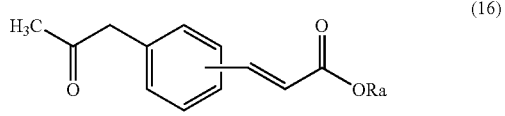

(16)

In a typical procedure, a solution of the olefin of formula (16) in a suitable solvent (e.g. methanol, ethanol, ethyl acetate) is treated with a palladium catalyst (e.g. 10% palladium on charcoal) and stirred under an atmosphere of hydrogen, optionally at elevated pressure (e.g. 60 psi), at temperature between room temperature and 60° C. for 8–24 hours.

The alkene of formula (16) may be prepared by a palladium mediated coupling of an activated olefin with an aryl halide of formula (17):

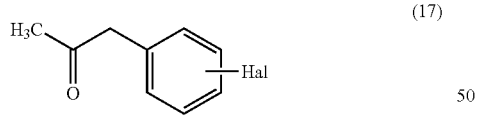

(17)

In a typical procedure, the aryl halide (17) is coupled with a vinyl ester (e.g. methyl acrylate) in the presence of a suitable palladium catalyst (e.g. tetrakis(triphenylphosphine)palladium(0) of formula $Pd(PPh_3)_4$, palladium acetate/tri-ortho-tolylphosphine of formula $Pd(OAc)_2/P(o-Tol)_3$ or (diphenylphosphino)ferrocenyl palladium chloride of formula $dppfPdCl_2$) in a suitable solvent (e.g. acetonitrile, N, N-dimethylformamide, toluene), optionally in the presence of a base such as triethylamine at a temperature between 40° C. and 110° C. for 8 to 24 hours.

The ketone of formula (17) is a commercial product. Alternatively a compound of formula (1) may be prepared by reaction of a bromide of formula (6) and an amine of formula (18):

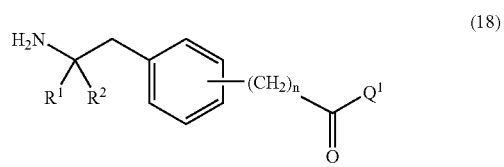

(18)

where $R^1$, $R^2$, $Q^1$ and n are as previously defined for the compounds of the formula (1) unless otherwise stated.

In a typical procedure, the amine of formula (18) is reacted with a bromide of formula (6) optionally in the presence of a solvent or mixture of solvents (e.g. dimethylsulfoxide, toluene, N, N-dimethylformamide, acetonitrile), optionally in the presence of a suitable base (e.g. triethylamine, diisopropylethylamine, potassium carbonate) at a temperature comprised between 80° C. and 120° C., for 12 to 48 hours.

The amide of formula (18) may be prepared by coupling an acid of formula (19) incorporating a suitable amine protecting group P1:

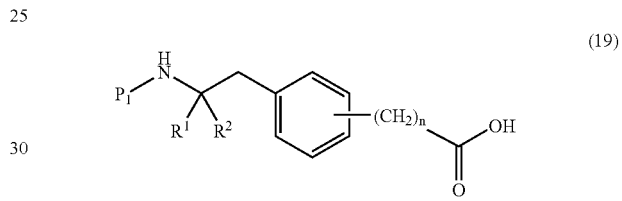

(19)

with an amine of formula $NHR^8-Q^2-A$ (3),

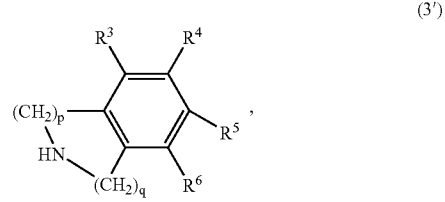

(3')

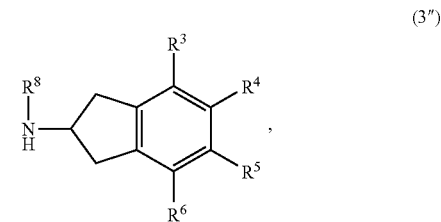

(3")

(3''')

The coupling is generally carried out in an excess of said amine as an acid receptor, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, N,N-dimethylformamide, tetrahydrofuran, dimethylsulfoxide, dichloromethane or ethyl acetate, and at temperature comprised between 10° C. and 40° C. (room temperature) for a period of 1–24 hours.

Said amine (3), (3'), (3") and (3''') is either commercially available or may be prepared by conventional methods well known to the one skilled in the art (e.g. reduction, oxidation, alkylation, transition metal-mediated coupling, protection, deprotection etc. . . . ) from commercially available material.

The acid of formula (19) may be prepared from the corresponding ester of formula (5). The acid of formula (19), where $R^1$ and $R^2$ are both $C_1$–$C_4$ alkyl, may be prepared from the ester (5) incorporating a suitable amine protecting group P1 either before or after the acid formation:

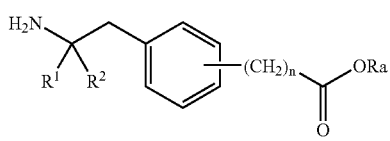

wherein Ra is a suitable acid protecting group, preferably a $(C_1$–$C_4)$alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

The amine of formula (5), where $R^1$ and $R^2$ are both H, may be prepared according to the following scheme:

Scheme 3

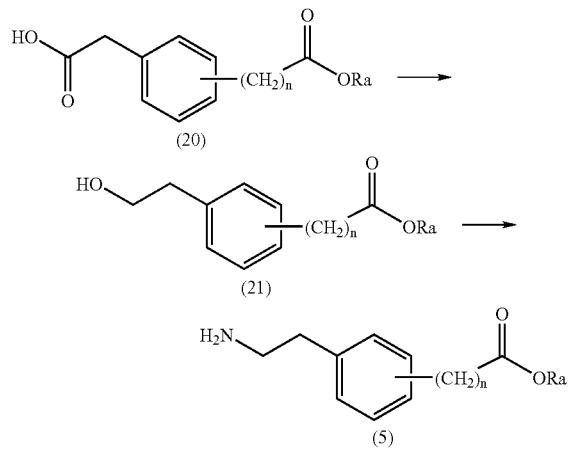

wherein $R^1$, $R^2$ and Ra are as previously defined.

In a typical procedure, the acid of formula (20) is preferentially reduced to the corresponding alcohol (21) in the presence of the ester. This may be performed by formation of the acyl imidazole or mixed anhydride and subsequent reduction with sodium borohydride or another suitable reducing agent.

Said primary alcohol of formula (21) is then converted into a leaving group such as mesylate, tosylate, bromide or iodide and displaced with an appropriate amine nucleophile. The preferred nucleophile is an azide ion which can then be reduced to the primary amine via hydrogenation or triphenylphosphine. Alternative nucleophiles could include ammonia or alkylamines such as benzylamine or allylamine and subsequent cleavage of the alkyl group to furnish the amine.

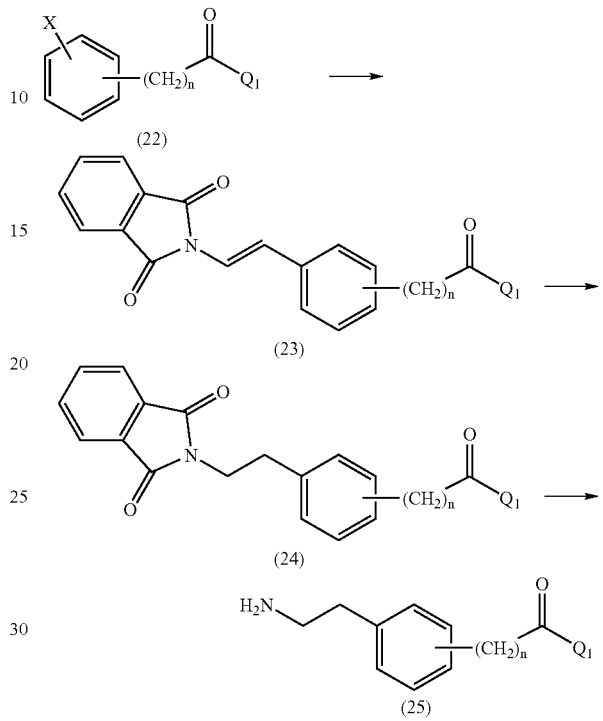

Alternatively, the amide of formula 22, can be prepared as outlined earlier using standard amide bond forming reactions. The compound of formula 22 can then be reacted with a protected vinylamine (e.g. N-vinylphthalimide) in the presence of a suitable catalyst (e.g. palladium(II)acetate) and a phosphine (e.g. triphenylphosphine, tri-ortho-tolylphosphine) in the presence of a base (e.g. N,N-diisopropylethylamine) in a solvent (e.g. N,N-dimethylformamide, acetonitrile) at a temperature comprised between 20° C. and 120° C. and for 1 to 48 hours. The alkene of formula 23 can then be reduced to an alkane of formula 24 using standard hydrogenation conditions and the protecting phthalimide group removed using standard protecting group removal. The amine of formula 25 can be reacted with a bromide of formula 6 to give a compound of formula 1 using conditions outlined earlier.

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. Greene and P. G. M. Wuts (*Protective Groups in Organic Synthesis*, John Wiley and Sons Inc., 1999) or by P. J. Kocienski (*Protecting groups*, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

Compounds of formula (1) containing the following substituents are preferred:

Preferably $Q^1$ is a group *—NH-$Q^2$-A, wherein A is cyclohexyl or adamantyl.

Preferably, $Q^1$ is wherein $R^3$, $R^4$, $R^5$ and $R^6$ are H.

Preferably $Q^1$ is wherein one of $R^3$ to $R^6$ is OH and the others are H.

Preferably, $Q^1$ is a group *—NH-$Q^2$-A, wherein A is a group wherein $R^3$, $R^4$, $R^5$, $R^6$ and $R^7$ are the same or different and are selected from H, $C_1$–$C_4$ alkyl, $OR^9$, $SR^9$, $SOR^9$, $SO_2R^9$, halo, CN, $CO_2R^9$, $CF_3$, $OCF_3$, $SO_2NR^9R^{10}$, $CONR^9R^{10}$, $NR^9R^{10}$, $NHCOR^{10}$ and phenyl optionally substituted with 1 to 3 groups selected from $OR^9$, halo and $C_1$–$C_4$ alkyl provided at least 2 of $R^3$ to $R^7$ are equal to H; wherein $R^9$ and $R^{10}$ are the same or different and are selected from H or $C_1$–$C_4$ alkyl.

More preferably, $Q^1$ is a group *—NH-$Q^2$-A, wherein A is a group wherein $R^3$, $R^4$, $R^5$, $R^6$ and $R^7$ are the same or different and are selected from H, OH, $CH_3$, $OCH_3$, $OCF_3$, $OCH_2$—$CH_3$, $SCH_3$, $N(CH_3)_2$, $N(C$=$O)CH_3$, $C$(=$O)NH_2$, $COOCH_3$, $SO_2CH_3$, $SO_2NH_2$, halo, CN, $CF_3$ and phenyl optionally substituted with OH provided at least 2 of $R^3$ to $R^7$ are equal to H.

In a preferred embodiment, A is a group wherein one of $R^3$ to $R^7$ is OH or phenyl substituted with OH.

In a preferred embodiment, A is a group wherein one of $R^3$ to $R^7$ is OH or phenyl substituted with OH and the other are selected from H, Cl or $CH_3$ provided at least 2 of $R^3$ to $R^7$ are H.

Preferably A is naphthyl optionally substituted with OH.

Preferably, A is naphthyl substituted with OH.

In the above groups of compounds, the following substituents are particularly preferred:

$Q^2$ is —$CH_2$—, —$(CH_2)_2$—, —$(CH_2)_3$—, —$CH_2$—$C(CH_3)_2$— or —$C(CH_3)_2$—, preferably —$CH_2$— or —$(CH_2)_2$.

$R^1$ is H or $C_1$–$C_4$ alkyl and $R^2$ is $C_1$–$C_4$ alkyl. More preferably, $R^1$ is H or $CH_3$ and $R^2$ is H or $CH_3$.

n is 0 or 1.

$R^1$ is H and $R^2$ is $CH_3$ and n is 0 or 1.

$R^1$ is $CH_3$, $R^2$ is $CH_3$ and n is 0 or 1.

Particularly preferred are the compounds of the formula (1) as described in the Examples section hereafter, i.e.:

N-Benzyl-2-(3-{2-[(2R)-2-(3-formylamino-4-hydroxyphenyl)-2-hydroxyethylamino]-2-methylpropyl}phenyl)acetamide;

N-(3,4-Dimethylbenzyl)-2-(3-{2-[(2R)-2-(3-formylamino-4-hydroxyphenyl)-2-hydroxyethylamino]-2-methylpropyl}phenyl)acetamide;

N-[2-(4-Chlorophenyl)ethyl]-3-{2-[(2R)-2-(3-formylamino-4-hydroxyphenyl)-2-hydroxyethylamino]-2-methylpropyl}benzamide;

N-[2-(2-Chlorophenyl)ethyl]-3-{2-[(2R)-2-(3-formylamino-4-hydroxyphenyl)-2-hydroxyethylamino]-2-methylpropyl}benzamide;

3-{2-[(2R)-2-(3-Formylamino-4-hydroxyphenyl)-2-hydroxyethylamino]-2-methylpropyl}-N-(2-naphthalen-1-ylethyl)benzamide;

3-{2-[(2R)-2-(3-Formylamino-4-hydroxyphenyl)-2-hydroxyethylamino]-2-methylpropyl}-N-[2-(4-methylphenyl)ethyl]benzamide;

N-[2-(2,6-Dimethylphenyl)ethyl]-3-{2-[(2R)-2-(3-formylamino-4-hydroxyphenyl)-2-hydroxyethylamino]-2-methylpropyl}benzamide;

N-[2-(2,3-Dimethylphenyl)ethyl]-3-{2-[(2R)-2-(3-formylamino-4-hydroxyphenyl)-2-hydroxyethylamino]-2-methylpropylbenzamide;

3-{2-[(2R)-2-(3-Formylamino-4-hydroxyphenyl)-2-hydroxyethylamino]-2-methylpropyl}-N-[2-(4-hydroxy-2,3-dimethylphenyl)ethyl]benzamide;

3-{2-[(2R)-2-(3-Formylamino-4-hydroxyphenyl)-2-hydroxyethylamino]-2-methylpropyl}-N-[2-(4-methoxyphenyl)ethyl]benzamide;

3-{2-[(2R)-2-(3-Formylamino-4-hydroxyphenyl)-2-hydroxyethylamino]-2-methylpropyl}-N-phenethyl-benzamide;

N-Cyclohexylmethyl-3-{2-[(2R)-2-(3-formylamino-4-hydroxyphenyl)-2-hydroxyethylamino]-2-methylpropyl}benzamide;

N-[5-((1R)-2-{1,1-Dimethyl-2-[3-(piperidine-1-carbonyl)phenyl]ethylamino}-1-hydroxyethyl)-2-hydroxyphenyl]formamide;

3-{2-[(2R)-2-(3-Formylamino-4-hydroxyphenyl)-2-hydroxyethylamino]-2-methylpropyl}-N-[2-(3-trifluoromethylphenyl)ethyl]benzamide;

3-{2-[(2R)-2-(3-Formylamino-4-hydroxyphenyl)-2-hydroxyethylamino]-2-methylpropyl}-N-(3-phenylpropyl)benzamide;

3-{2-[(2R)-2-(3-Formylamino-4-hydroxyphenyl)-2-hydroxyethylamino]-2-methylpropyl}-N-indan-2-ylbenzamide;

3-{2-[(2R)-2-(3-Formylamino-4-hydroxyphenyl)-2-hydroxyethylamino]-2-methylpropyl}-N-(2-pyridin-2-ylethyl)benzamide;

3-{2-[(2R)-2-(3-Formylamino-4-hydroxyphenyl)-2-hydroxyethylamino]-2-methylpropyl}-N-[2-(4-sulfamoylphenyl)ethyl]benzamide;

N-(4-Dimethylaminobenzyl)-2-(3-{(2R)-2-[(2R)-2-(3-formylamino-4-hydroxyphenyl)-2-hydroxyethylamino]propyl}phenyl)acetamide;

N-[5-(2-{(1R)-2-[3-(3,4-Dihydro-1H-isoquinoline-2-carbonyl)-phenyl]-1,1-dimethyl-ethylamino}-1-hydroxyethyl)-2-hydroxyphenyl]formamide;

3-{2-[(2R)-2-(3-Formylamino-4-hydroxyphenyl)-2-hydroxyethylamino]-2-methylpropyl}-N-(4'-hydroxybiphenyl-3-ylmethyl)benzamide 3-{2-[(2R)-2-(3-Formylamino-4-hydroxyphenyl)-2-hydroxyethylamino]-2-methylpropyl}-N-[2-(4-hydroxy-2,5-dimethylphenyl)ethyl]benzamide;

3-{2-[(2R)-2-(3-Formylamino-4-hydroxyphenyl)-2-hydroxyethylamino]-2-methylpropyl}-N-[2-(4-hydroxy-3-methylphenyl)ethyl]benzamide;

N-(4-Acetylaminobenzyl)-2-(3-{(2R)-2-[(2R)-2-(3-formylamino-4-hydroxyphenyl)-2-hydroxyethylamino]propyl}phenyl)acetamide;

4-{[2-(3-{(2R)-2-[(2R)-2-(3-Formylamino-4-hydroxyphenyl)-2-hydroxyethylamino]propyl}phenyl)acetylamino]methyl}benzamide;

N-Adamantan-1-yl-3-{2-[(2R)-2-(3-formylamino-4-hydroxyphenyl)-2-hydroxyethylamino]-2-methylpropyl}benzamide;

3-{2-[(2R)-2-(3-Formylamino-4-hydroxyphenyl)-2-hydroxyethylamino]-2-methylpropyl}-N-(2-hydroxy-naphthalen-1-ylmethyl)benzamide;

3-{2-[(2R)-2-(3-Formylamino-4-hydroxyphenyl)-2-hydroxyethylamino]-2-methylpropyl}-N-(4-hydroxy-3,5-dimethylbenzyl)benzamide;

3-{2-[(2R)-2-(3-Formylamino-4-hydroxyphenyl)-2-hydroxyethylamino]-2-methylpropyl}-N-(6-hydroxy-naphthaleN-2-ylmethyl)benzamide;

N-(3,6-Dichloro-2-hydroxybenzyl)-3-{2-[(2R)-2-(3-formylamino-4-hydroxyphenyl)-2-hydroxyethylamino]-2-methylpropyl}benzamide;

N-(3,4-Dimethylbenzyl)-2-(3-{2-[(2R)-2-(3-formylamino-4-hydroxyphenyl)-2-hydroxyethylamino]ethyl}phenyl)acetamide;

3-{2-[(2R)-2-(3-Formylamino-4-hydroxyphenyl)-2-hydroxyethylamino]-2-methylpropyl}-N-[2-(4-hydroxyphenyl)-2-methylpropyl]benzamide;

3-{2-[(2R)-2-(3-Formylamino-4-hydroxyphenyl)-2-hydroxyethylamino]-2-methylpropyl}-N-(4'-hydroxybiphenyl-4-ylmethyl)benzamide;

N-Adamantan-1-yl-2-(3-{(2R)-2-[(2R)-2-(3-formylamino-4-hydroxyphenyl)-2-hydroxyethylamino]propyl}phenyl)acetamide;

N-[5-(2-{2-[3-(10-Aza-tricyclo[6.3.1.0*2,7*]dodeca-2(7),3,5-triene-10-carbonyl)phenyl]-1,1-dimethylethylamino}-1-hydroxyethyl)-2-hydroxyphenyl]-formamide;

2-(3-{(2R)-2-[(2R)-2-(3-Formylamino-4-hydroxyphenyl)-2-hydroxyethylamino]propyl}phenyl)-N-(4'-hydroxybiphenyl-3-ylmethyl)acetamide;

4-{[2-(3-{2-[(2R)-2-(3-Formylamino-4-hydroxyphenyl)-2-hydroxyethylamino]-2-methylpropyl}phenyl)-acetylamino]methyl}benzoic acid methyl ester;

2-(3-{(2R)-2-[(2R)-2-(3-Formylamino-4-hydroxyphenyl)-2-hydroxyethylamino]-2-methylpropyl}phenyl)-N-(4-trifluoromethoxy-benzyl)acetamide;

N-(2-Chloro-4-hydroxybenzyl)-N-ethyl-2-(3-{(2R)-2-[(2R)-2-(3-formylamino-4-hydroxyphenyl)-2-hydroxyethylamino]-2-methylpropyl}phenyl)-cetamide;

N-(2-Chloro-4-hydroxybenzyl)-2-(3-{(2R)-2-[(2R)-2-(3-formylamino-4-hydroxyphenyl)-2-hydroxyethylamino]-2-methylpropyl}-phenyl)acetamide;

2-(3-{(2R)-2-[(2R)-2-(3-Formylamino4-hydroxyphenyl)-2-hydroxyethylamino]propyl}phenyl)-N-(4-hydroxy-3,5-dimethylbenzyl)acetamide;

2-(3-{(2R)-2-[(2R)-2-(3-Formylamino-4-hydroxyphenyl)-2-hydroxyethylamino]propyl}phenyl)-N-(2-hydroxynaphthalen-1-ylmethyl)acetamide;

N-(5-Chloro-2-hydroxybenzyl)-2-(3-{(2R)-2-[(2R)-2-(3-formylamino-4-hydroxyphenyl)-2-hydroxyethylamino]propyl}phenyl)acetamide;

N-(3,5-Dichloro-2-hydroxybenzyl)-2-(3-{(2R)-2-[(2R)-2-(3-formylamino-4-hydroxyphenyl)-2-hydroxyethylamino]propyl}phenyl)acetamide;

2-(3-{(2R)-2-[(2R)-2-(3-Formylamino-4-hydroxyphenyl)-2-hydroxyethylamino]propyl}phenyl)-N-(6-hydroxynaphthalen-2-ylmethyl)acetamide;

2-(3-{(2R)-2-[(2R)-2-(3-Formylamino-4-hydroxyphenyl)-2-hydroxyethylamino]propyl}phenyl)-N-(4'-hydroxybiphenyl-4-ylmethyl)acetamide;

N-(4-Cyano-benzyl)-2-(3-{2-[(2R)-2-(3-formylamino-4-hydroxyphenyl)-2-hydroxyethylamino]-2-methylpropyl}-phenyl)-acetamide;

2-(3-{2-[(2R)-2-(3-Formylamino-4-hydroxyphenyl)-2-hydroxyethylamino]-2-methylpropyl}-phenyl)-N-(4-methanesulfonyl-benzyl)-acetamide;

2-(3-{2-[(2R)-2-(3-Formylamino-4-hydroxyphenyl)-2-hydroxyethylamino]-2-methylpropyl}-phenyl)-N-(4-methylsulfanyl-benzyl)-acetamide;

2-(3-{2-[(2R)-2-(3-Formylamino-4-hydroxyphenyl)-2-hydroxyethylamino]-2-methylpropyl}-phenyl)-N-(4-trifluoromethyl-benzyl)-acetamide;

2-(3-{2-[(2R)-2-(3-Formylamino-4-hydroxyphenyl)-2-hydroxyethylamino]-2-methylpropyl}phenyl)-N-(4'-hydroxy-biphenyl-4-ylmethyl)acetamide;

N-[2-(5-Chloro-2-hydroxyphenyl)-ethyl]-3-{2-[(2R)-2-(3-formylamino-4-hydroxyphenyl)-2-hydroxyethylamino]-2-methylpropy}-benzamide;

2-(3-{2-[(2R)-2-(3-Formylamino-4-hydroxyphenyl)-2-hydroxyethylamino]-2-methylpropyl}phenyl)-N-(4'-hydroxybiphenyl-3-ylmethyl)-acetamide;

3-{2-[(2R)-2-(3-Formylamino-4-hydroxyphenyl)-2-hydroxyethylamino]-propyl}-N-[2-(4-hydroxyphenyl)-2-methylpropyl]-benzamide;

N-(2-Chloro-4-hydroxybenzyl)-2-(3-{(2R)-2-[(2R)-(2R)-2-(3-formylamino-4-hydroxyphenyl)-2-hydroxyethylamino]propyl}phenyl)acetamide;

N-[2-(5-Chloro-2-hydroxyphenyl)-ethyl]-3-{2-[(2R)-2-(3-formylamino-4-hydroxyphenyl)-2-hydroxyethylamino]-2-methylpropyl}benzamide;

3-{2-[(2R)-2-(3-Formylamino-4-hydroxyphenyl)-2-hydroxyethylamino]-propyl}-N-[2-(4-hydroxyphenyl)-2-methylpropyl]benzamide;

2-(3-{2-[(2R)-2-(3-Formylamino-4-hydroxyphenyl)-2-hydroxyethylamino]-2-methylpropyl}phenyl)-N-(tetrahydro-thiopyran-4-yl)acetamide;

N-(5-Chloro-2-hydroxybenzyl)-2-(3-{2-[(2R)-2-(3-formylamino-4-hydroxyphenyl)-2-hydroxyethylamino]-2-methylpropyl}phenyl)acetamide; and, N-{5-[(1R)-2-((1R)-2-{3-[3-(3,4-Dihydro-1H-isoquinolin-2-yl)-3-oxopropyl]phenyl}-1-methylethylamino)-1-hydroxyethyl]-2-hydroxyphenyl}formamide.

According to one aspect of the present invention, the compounds of formula (1) wherein the $(CH_2)_n—C(=O)Q^1$ group is in the meta position are generally preferred.

Pharmaceutically acceptable salts of the compounds of formula (1) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:

(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269–1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs'_of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (1) contains a carboxylic acid functionality (—COOH), an ester thereof, for example, a compound wherein the hydrogen of the carboxylic acid functionality of the compound of formula (1) is replaced by $(C_1-C_8)$alkyl;
(ii) where the compound of formula (1) contains an alcohol functionality (—OH), an ether thereof, for example, a compound wherein the hydrogen of the alcohol functionality of the compound of formula (1) is replaced by $(C_1-C_6)$alkanoyloxymethyl; and
(iii) where the compound of formula (1) contains a primary or secondary amino functionality (—NH$_2$ or —NHR where R≠H), an amide thereof, for example, a compound wherein, as the case may be, one or both hydrogens of the amino functionality of the compound of formula (1) is/are replaced by $(C_1-C_{10})$alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a methyl group, an hydroxymethyl derivative thereof (—CH$_3$→—CH$_2$OH):
(ii) where the compound of formula (1) contains an alkoxy group, an hydroxy derivative thereof (—OR→—OH);
(iii) where the compound of formula (1) contains a tertiary amino group, a secondary amino derivative thereof (—NR$^1$R$^2$→—NHR$^1$ or —NHR$^2$);
(iv) where the compound of formula (1) contains a secondary amino group, a primary derivative thereof (—NHR$^1$→—NH$_2$);
(v) where the compound of formula (1) contains a phenyl moiety, a phenol derivative thereof (—Ph→—PhOH); and
(vi) where the compound of formula (1) contains an amide group, a carboxylic acid derivative thereof (—CONH$_2$→COOH).

Compounds of formula (1) containing one or more asymmetric carbon atomscan exist as two or more stereoisomers. Where a compound of formula (1) contains an alkenyl or alkenylene group, geometric cisitrans (or Z/E) isomers are possible. Where structural isomers are interconvertible via a low energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, N.Y., 1994).

According to one aspect of the present invention, the (R,R)-stereoisomer of the formula below, wherein $R^1$ is hydrogen and $R^2$ is $C_1-C_4$ alkyl, preferably methyl, and n and $Q^1$ are as defined above, is generally preferred:

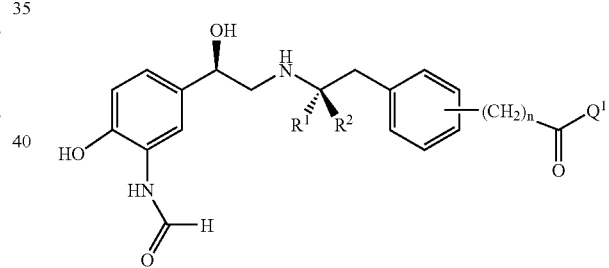

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (1), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the_effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981–986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose,_croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1–14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA)_ microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955–958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided dosesand may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-α) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκβ pathway, e.g. IKK inhibitors,
(w) modulators of cytokine signalling pathyways such as p38 MAP kinase or syk kinase,
(x) Agents that can be classed as mucolytics or anti-tussive,
(y) Antibiotics,
(z) HDAC inhibitors, and,
(aa) PI3 kinase inhibitors.

According to the present invention, combination of the compounds of formula (1) with H3 antagonists,
Muscarinic M3 receptor antagonists,
PDE4 inhibitors,
glucocorticosteroids,
Adenosine A2a receptor agonists,
Modulators of cytokine signalling pathyways such as p38 MAP kinase or syk kinase, or,
Leukotriene antagonists (LTRAs) including antagonists of $LTB_4$, $LTC_4$, $LTD_4$, and $LTE_4$, are preferred.

According to the present invention, combination of the compounds of formula (1) with:

glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or muscarinic M3 receptor antagonists or anticholinergic agents including in particular ipratropium salts, namely bromide, tiotropium salts, namely bromide, oxitropium salts, namely bromide, perenzepine, and telenzepine, are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the β2 receptor and thereby have a wide range of therapeutic applications, as described further below, because of the essential role which the β2 receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the β2 receptor is involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions in a mammal, including a human being, in particular the diseases and/or conditions listed above, comprising administering said mammal with an effective amount of a compound of formula (1), its pharmaceutically acceptable salts and/or derived forms.

The following examples illustrate the preparation of the compounds of the formula (1):

Preparation 1:
(3-Ethoxycarbonylmethylphenyl)acetic acid ethyl ester

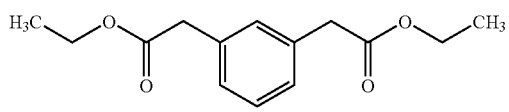

2,2'-(1,3-Phenylene)diacetic acid (10.0 g, 51 mmol) was dissolved in ethanol (100 mL) and the solution treated dropwise with acetyl chloride (2.5 mL). The reaction mixture was stirred at reflux for 18 hours before being allowed to cool and concentrated in vacuo. The residue was taken up in ethyl acetate (100 mL) and extracted with sodium bicarbonate solution (3×50 mL) and brine (3×50 mL). The organic phase was dried (MgSO$_4$), concentrated in vacuo and the residue triturated with pentane to yield the product (11.8 g). $^1$HNMR (CDCl$_3$, 400 MHz) δ: 1.31 (6H, t), 3.65 (4H, s), 4.20 (4H, q), 7.24–7.36 (4H, m); LRMS ESI m/z 251 [M+H]$^+$ Preparation 2:
(3-Ethoxycarbonylmethylphenyl)acetic acid

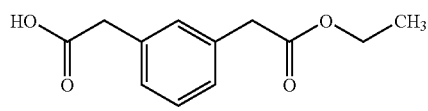

A solution of preparation 1 (44.3 g, 177 mmol) and 2,2'-(1,3-phenylene)diacetic acid (59.2 g, 308 mmol) in ethanol (24 mL) and dioxan (290 mL) was treated dropwise with hydrochloric acid (12 M, 4.9 mL, 58.8 mmol). The reaction mixture was stirred at reflux for 18 hours before being allowed to cool and concentrated to low volume. The reaction mixture was diluted with toluene (125 mL) and the resulting slurry filtered. The filtrate was concentrated in vacuo and the residue taken up in water and basified with sodium bicarbonate until pH neutral. The mixture was diluted with ethyl acetate (200 mL) and the organic layer was separated and washed with sodium bicarbonate solution (5×30 ml) and brine (50 mL). The combined aqueous extracts were acidified to pH 3 with 6M hydrochloric acid and extracted with diethylether (3×30 mL). The organics were combined, dried (MgSO$_4$) and concentrated in vacuo. The residue was triturated with pentane to yield a colourless solid (10.8 g). $^1$HNMR (CD$_3$OD, 400 MHz) δ: 1.25 (3H, t), 3.60 (2H, m), 3.63 (2H, m), 4.15 (2H, q), 7.18–7.32 (4H, m); LRMS ESI m/z 245 [M+Na]$^+$ Preparation 3:
[3-(2-Hydroxy-2-methylpropyl)phenyl]acetic acid

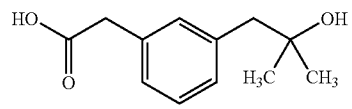

Methyl magnesium chloride (51 mL of a 3M solution in tetrahydrofuran, 153 mmol) was added dropwise to a stirred solution of the preparation 2 (11.6 g, 51 mmol) (International Journal of Peptide and Protein Research, 1987, 29(3), 331) in tetrahydrofuran (300 mL) at 0° C. under nitrogen. The reaction was allowed to warm to room temperature overnight with the formation of a thick white precipitate and then water (50 mL) and 2N hydrochloric acid (80 mL) were cautiously added. The aqueous was extracted with ethyl acetate (2×300 mL) and the combined organics washed with brine (50 mL), dried (sodium sulfate), and the solvent removed in vacuo to furnish the title compound as a golden oil (11.2 g). $^1$HNMR (CDCl$_3$, 400 MHz) δ: 1.22 (6H, s), 2.75 (2H, s), 3.63 (2H, s), 7.12–7.30 (4H, m); LRMS ESI m/z 209 [M+H]$^+$

Preparation 4: (3-{2-[(Chloroacetyl)amino]-2-methylpropyl}phenyl) acetic acid

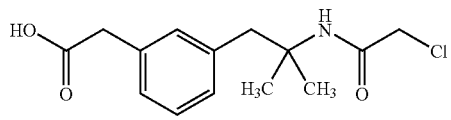

2-Chloroacetonitrile (8.8 mL, 140 mmol) was added to a solution of preparation 3 (16.0 g, 70 mmol) in acetic acid (33 mL) and cooled to 0° C. The resulting solution was treated with concentrated sulphuric acid (33 mL) and allowed to warm gradually to room temperature. After 4 hours the reaction mixture was poured onto ice and basified with solid sodium carbonate. The solution was extracted with ethyl acetate (2×500 mL) and the combined organic extracts dried (MgSO$_4$) and concentrated in vacuo to give the title product as a colourless solid (19.0 g). $^1$HNMR (CDCl$_3$, 400 MHz) δ: 1.36 (6H, s), 3.02 (2H, s), 3.62 (2H, s), 3.95 (2H, s), 6.19 (1H, m), 7.06–7.31 (4H, m); LRMS ESI m/z 282 [M−H]$^-$

Preparation 5: [3-(2-Amino-2-methylpropyl)phenyl]acetic acid methyl ester

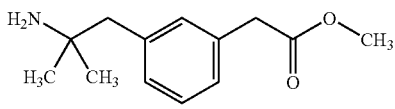

A solution of preparation 4 (5.1 g, 18 mmol), thiourea (1.6 g, 21 mmol) and acetic acid (18 mL) in ethanol (80 mL) was heated to reflux under a nitrogen atmosphere for 16 hours. The reaction mixture was allowed to cool to room temperature and filtered and the filtrate concentrated in vacuo. The residue was dissolved in ethanol (150 mL), saturated with hydrogen chloride gas and the resulting solution heated to reflux for 16 hours. The mixture was concentrated in vacuo and ethyl acetate (200 mL) and 5% aqueous sodium carbonate solution (200 mL) added. The organic phase was washed with brine (100 mL), dried (MgSO$_4$) and concentrated in vacuo. The residue was purified by strong cation exchange resin (methanol and then a 2M solution of ammonia in methanol) to give a yellow oil (2.68 g). $^1$HNMR (CDCl$_3$, 400 MHz) δ: 1.14 (6H, s), 2.68 (2H, s), 3.62 (2H, s), 3.69 (3H, s), 7.08–7.16 (3H, m), 7.23–7.27 (1H, m); LRMS ESI m/z 222 [M+H]$^+$

Preparation 6: [3-(2-tert-Butoxycarbonylamino-2-methylpropyl)phenyl] acetic acid methyl ester

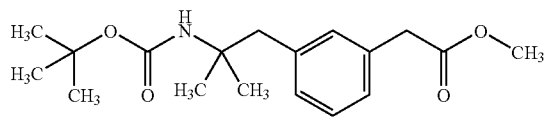

A solution of di-tert-butyldicarboxylate (8.19 g, 38.0 mmol) in dichloromethane (40 mL) was added to a solution of preparation 5 (8.4 g, 38.0 mmol) and triethylamine (5.2 mL, 38.0 mmol) in dichloromethane (60 mL) at 0–5° C. The mixture was allowed to warm to RT and stirred overnight. The solvent was removed and the residue treated with sodium carbonate solution and extracted with ethyl acetate (3×30 mL). The combined organic layers were washed with brine (3×20 mL) and dried (Na$_2$SO$_4$). The product was purified by chromatography (0–80% ethyl acetate in hexane) to yield a colourless oil which was dissolved in diethylether (×3) and evaporated (10.1 g). $^1$HNMR (CDCl$_3$, 400 MHz) δ: 1.26 (6H, s), 1.46 (9H, s), 2.97 (2H, s), 3.60 (2H, s), 3.68 (3H, s), 4.26 (1H, bs), 7.05–7.07 (2H, m), 7.13–7.17 (1H, m), 7.22–7.26 (1H, m); LRMS ESI m/z 344 [M+Na]$^+$

Preparation 7: [3-(2-tert-Butoxycarbonylamino-2-methylpropyl)phenyl] acetic acid

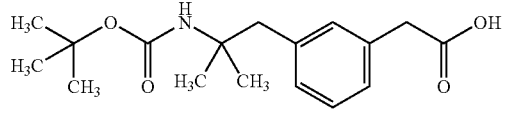

Preparation 6 (7.45 g, 23.0 mmol), sodium hydroxide solution (5M, 4.6 mL, 115 mmol), dioxane (30 mL) and water (8 mL) were stirred at RT for 18 h. The solvent was removed and the material dissolved in water, cooled and acidified to pH 3 with hydrochloric acid (2M). The product was extracted with ethyl acetate (3×30 mL), and the organics washed with brine (3×30 mL) and dried (Na$_2$SO$_4$). The resulting oil was dissolved in diethylether and evaporated to yield a colourless gum (7.0 g). $^1$HNMR (CD$_3$OD, 400 MHz) δ: 1.23(6H, s), 1.48(9H, s), 2.96(2H, s), 3.57(2H, s), 7.04–7.06(2H, m), 7.11–7.13(1H, m), 7.18–7.22 (1H, m). LRMS APCI m/z 308 [M+H]$^+$

Preparation 8: (2-{3-[(3,4-Dichlorobenzylcarbamoyl)methyl]phenyl}-1,1-dimethyl-ethyl)carbamic acid tert-butyl ester

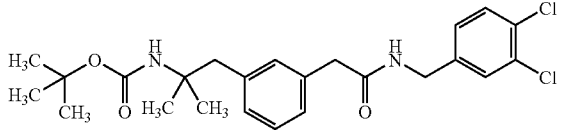

3,4-Dichlorobenzylamine (1.30 mL, 9.76 mmol) was added to a solution of preparation 7 (3.00 g, 9.76 mmol), hydroxybenzotriazole hydrate (1.50 g, 9.76 mmol), 1-(3-dimethylaminopropyl)-3-ethylcarbodiimide hydrochloride (1.87 g, 9.76 mmol) and triethylamine (4.07 mL, 11.2 mmol) and the resulting solution was stirred at RT for 18 h. The solvent was removed and the crude material taken up in ethyl acetate (50 mL) and washed with water (30 mL), sodium carbonate solution (2×30 mL), brine (30 ml), hydrochloric acid (0.5 M, 2×30 ml) and brine (30 mL) and then dried (Na$_2$SO$_4$). The resulting white solid was triturated with diethylether (3.1 g). $^1$HNMR (CDCl$_3$, 400 MHz) δ: 1.25 (6H, s), 1.45 (9H, s), 2.97 (2H, s), 3.62 (2H, s), 4.22 (1 H, bs), 4.34 (2H, d), 5.78 (1H, bs), 6.99–7.01 (1H, dd), 7.04 (1H, s), 7.07–7.09 (1H, d), 7.12–7.14 (1H, d), 7.22 (1H, d), 7.27 (1H, d), 7.32 (1H, d). LRMS APCI m/z 465 [M+H]$^+$

Preparation 9: (2-{3-[(3,4-Dimethylbenzylcarbamoyl)methyl]phenyl}-1,1-dimethyl-ethyl)carbamic acid tert-butyl ester

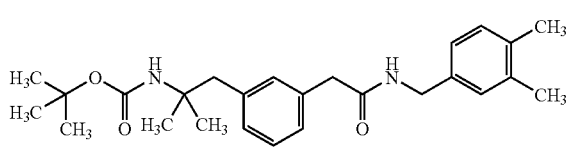

Prepared using the acid from Preparation 7 and the method described for Preparation 8 and 3,4-dimethylbenzylamine. $^1$HNMR (CDCl$_3$, 400 MHz) δ: 1.19 (6H, s), 1.46 (9H, s), 2.20 (6H, d), 2.95 (2H, s), 3.59 (2H, s), 4.15 (1H, bs), 4.32 (2H, d), 5.59 (1H, bs), 6.86–6.93 (2H, m), 7.02–7.06 (3H, m), 7.13–7.15 (1H, d), 7.23–7.27 (1H, m). LRMS APCI m/z 425 [M+H]$^+$

Preparation 10: 2-[3-(2-Amino-2-methylpropyl)phenyl]-N-(3,4-dichloro benzyl)acetamide

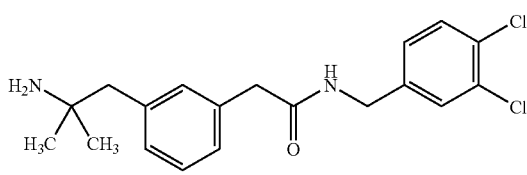

Preparation 8 (3.0 g, 6.50 mmol) in dioxane (5 mL) was treated with hydrogen chloride (4M in dioxane, 20 mL) and the resulting solution left to stir at RT for 18 h. The solvent was removed and the compound re-dissolved in methanol (×2) and evaporated, then the resulting gum suspended in diethylether (×2) and evaporated to yield a white solid (2.7 g). mp (ethyl acetate-methanol) 214–216 (dec)° C. $^1$HNMR (CD$_3$OD, 400 MHz) δ: 1.33 (6H, s), 2.90 (2H, s), 3.59 (2H, s), 4.35 (2H, s), 7.13–7.19 (3H, m), 7.24–7.27 (1H, m), 7.31–7.38 (2H, m), 7.42 (1H, d). LRMS ESI m/z 365 [M+H]$^+$

Preparation 11: 2-[3-(2-Amino-2-methylpropyl)phenyl]-N-(3,4-dimethyl benzyl)acetamide

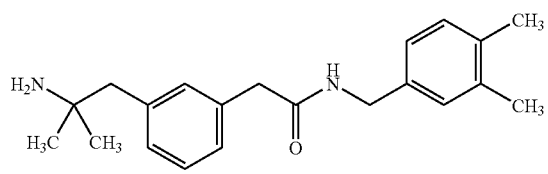

Prepared using the amide from Preparation 9 and the method described for Preparation 10. $^1$HNMR (CD$_3$OD, 400 MHz) δ: 1.32 (6H, s), 2.21 (6H, s), 2.89 (2H, s), 3.56 (2H, s), 4.29 (2H, s), 6.95–7.05 (3H, m), 7.14–7.16 (2H, m), 7.24–7.26 (1H, m), 7.31–7.35 (1H, m). LRMS ESI m/z 325 [M+H]$^+$

Preparation 12: N2-Benzyloxy-5-[(1R)-2-bromo-1-(tert-butyldimethyl silanyloxy)ethyl]phenyl}formamide

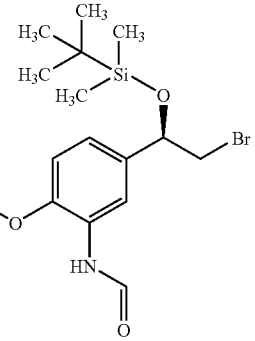

To a solution of N-[2-benzyloxy-5-(2-bromo-1-hydroxyethyl)phenyl]formamide (Organic Process Research and Development 1998, 2, 96–99) (4.12 g, 11.8 mmol) in N,N-dimethylformamide (25 mL) at RT under N$_2$ was added tert-butyldimethylsilyl chloride (3.50 g, 23.2 mmol), imidazole (1.90 g, 27.9 mmol) and 4-(dimethylamino)pyridine (40 mg, 330 □mol). The resulting solution was stirred at RT overnight, the solvent was removed and the product taken up in ethyl acetate (70 mL). The organics were washed with water (100 mL), and the aqueous extracted with ethyl acetate (20 mlmL The combined organics were washed with hydrochloric acid (2M, 50 ml), brine (100 mL) and dried (MgSO$_4$). The crude material was purified by chromatography (5–25% ethyl acetate in pentane) to yield a colourless oil (5.7 g). $^1$HNMR (CDCl$_3$, 400 MHz) δ: –0.08 to –0.05 (3H, m), 0.09–0.11 (3H, s), 0.89–0.90 (9H, m), 3.38–3.55 (2H, m), 3.78–3.84 (1H, m), 5.06–5.11 (2H, m), 6.90–6.97 (1H, m), 7.03–7.12 (1H, m), 7.24 (m), 7.36–7.43 (5H, m), 7.67–7.78 (m), 7.88 (d), 8.74 (d); LRMS APCI m/z 464/466 [M+H]$^+$

Preparation 13: 2-(3-{2-[(2R)-2-(4-Benzyloxy-3-formylaminophenyl)-2-(tert-butyl-dimethylsilanyloxy)ethylamino]-2-methylpropyl}phenyl)-N-(3,4-dichlorobenzyl)acetamide

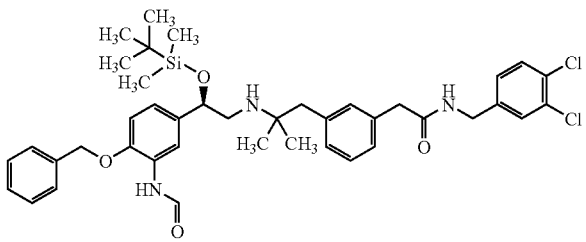

Preparation 12 (500 mg, 1.08 mmol) and preparation 10 (780 mg, 216 mmol) were heated and stirred at 90° C. for 24 h. After cooling the material was dissolved in methanol and evaporated, the material was suspended in diethylether and the precipitate filtered off. The filtrate was evaporated and the material purified by chromatography (0–5% methanol in dichloromethane) and then suspended in diethylether (×3) and evaporated to yield a foam (425 mg). $^1$HNMR (CD$_3$OD, 400 MHz) δ: –0.20 to –0.18 (3H, m), –0.04 to 0.00 (3H, m), 0.78–0.81 (9H, m), 1.01–1.03 (3H, m), 1.05 (3H, bs), 2.62–2.74 (3H, m), 2.83–2.88 (1H, m), 3.52 (2H, d), 4.31

(2H, s), 4.68–4.71 (1H, m), 5.17–5.19 (2H, m), 7.00–7.23 (7H, m), 7.29–7.41 (5H, m), 7.44–7.49 (2H, m), 8.57 (s); LRMS ESI m/z 748 [M+H]+; HRMS $C_{41}H_{51}Cl_2N_3O_4Si$ 748.3099 [M+H]+ found 748.3066.

Preparation 14: 2-(3-{2-[(2R)-2-(4-Benzyloxy-3-formylaminophenyl)-2-(tert-butyl-dimethylsilanyloxy)ethylamino]-2-methylpropylphenyl)-N-(3,4-dimethylbenzyl)acetamide

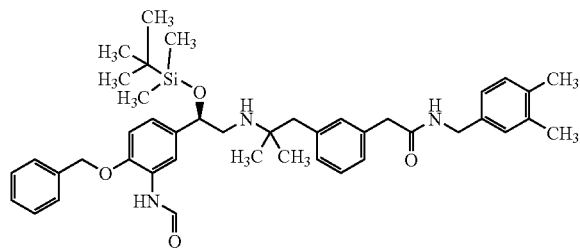

Prepared using the amide from Preparation 13, the bromide from Preparation 12 and the method described for Preparation 11. ¹HNMR (CDCl₃, 400 MHz) δ: −0.17, −0.16 (3H, 2x s), −0.05 to −0.01 (3H, m), 0.78–0.82 (9H, m), 0.97–1.01 (6H, m), 2.19 (3H, s), 2.20 (3H, s), 2.56–2.90 (4H, m), 3.54–3.63 (2H, m), 4.28–4.35 (2H, m), 4.67–4.74 (1H, m), 5.06–5.09 (2H, m), 5.58–5.62 and 5.99–6.03 (1H, m), 6.87–7.25 (9H, m), 7.35–7.44 (5H, m), 7.68–7.79 (1H, m), 8.30 (d), 8.43 (d), 8.71 (s), 8.74 (s); LRMS ESI m/z 748 [M+H]+; HRMS $C_{43}H_{57}N_3O_4Si$ 708.4191 [M+H]+ found 708.4156.

Preparation 15: N-Benzyl-2-(3-{2-[(2R)-2-(tert-butyldimethylsilanyloxy)-2-(3-formylamino-4-hydroxyphenyl)ethylamino]-2-methylpropyl)phenyl)acetamide

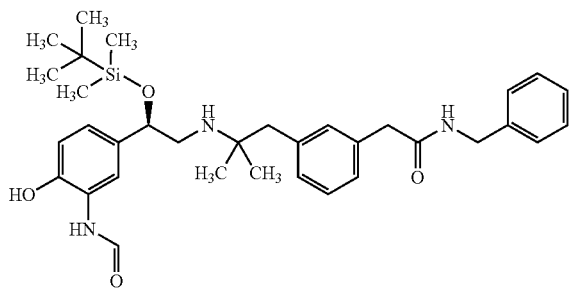

Preparation 13 (100 mg, 134 □mol) and palladium-on-carbon (10%, 20 mg) in methanol (10 mL) were hydrogenated at 50 psi/RT for 6 h. The mixture was filtered through a 'filter-aid' and the solvent removed. The material was suspended in sodium hydrogen carbonate solution and extracted with ethyl acetate (30 mL). The organic layer was washed with sodium hydrogen carbonate solution, brine (2×mL) and dried (Na₂SO₄). The resulting material was suspended in diethylether (×3) and evaporated to yield a film (24 mg). ¹HNMR (CD₃OD, 400 MHz) δ: −0.19 (3H, s), −0.02 (3H, s), 0.79 (9H, s), 1.04 (3H, s), 1.07 (3H, s), 2.62–2.89 (4H, m), 3.48–3.56 (2H, dd), 4.35 (2H, s), 4.61 (1H, bs), 4.69–4.72 (1H, m), 5.17–5.19 (2H, m), 6.79–6.85 (1H, m), 6.91–6.94 (1H, m), 7.04–7.06 (1H, m), 7.11–7.28 (7H, m), 8.12 (1H, d), 8.27, 8.59 (1H, 2xs). LRMS ESI m/z 590 [M+H]+; HRMS $C_{34}H_{47}N_3O_4Si$ 590.3402 [M+H]+ found 590.3409.

Preparation 16: 2-(3-{2-[(2R)-2-(tert-Butyldimethylsilanyloxy)-2-(3-formylamino-4-hydroxyphenyl)ethylamino]-2-methylpropylphenyl)-N-(3,4-dimethylbenzyl)acetamide

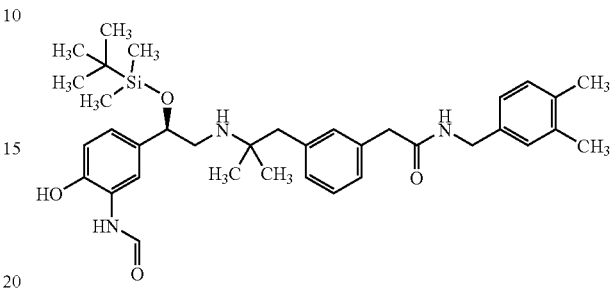

Prepared using the amide from Preparation 14 and the method described for Preparation 15. The product was purified by chromatography (0–3.5% methanol in dichloromethane+0.3% ammonia) to yield a foam (85 mg). ¹HNMR (CD₃OD, 400 MHz) δ: −0.20 to −18 (3H, m), −0.03–0.00 (3H, m), 0.79–0.81 (9H, m), 1.02–1.05 (6H, m), 2.19 (3H, s), 2.20 (3H, s), 2.61–2.73 (3H, m), 2.83–2.88 (1H, m), 3.46 (2H, dd), 4.27 (2H, s), 4.65 (1H, dd), 6.78–7.22 (8H, m), 8.12 (d), 8.27 (s), 8.59(s). LRMS ESI m/z 618 [M+H]+. ¹HRMS $C_{36}H_{51}N_3O_4Si$ 618.3722 [M+H]+ found 618.3701.

Preparation 17: Methyl (3-bromophenyl)acetate

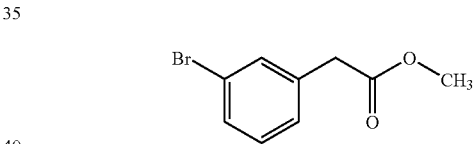

Acetyl chloride (0.7 mL, 9.3 mmol) was slowly added to a solution of (3-bromo-phenyl)acetic acid (20.0 g, 93 mmol) in methanol (500 mL) at 0° C. under nitrogen and the reaction was allowed to warm gradually to room temperature over a period of 5 hours. The solvent was removed in vacuo and the residual oil was re-dissolved in dichloromethane, dried over sodium sulfate and concentrated in vacuo to give the title compound as a colourless oil (20.6 g). ¹H NMR(400 MHz, CDCl₃): δ: 3.59(2H, s), 3.70(3H, s), 7.17–7.24(2H, m), 7.37–7.45(2H, m); LRMS ESI m/z 253 [M+Na]+

Preparation 18: Methyl [3-(2-oxopropyl)phenyl]acetate

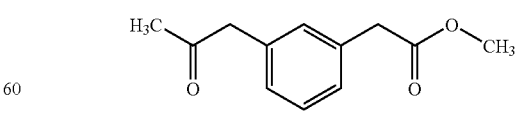

Tributyltin methoxide (28.3 mL, 98 mmol), the product of preparation 17 (15.0 g, 65 mmol), isopropenyl acetate (10.8 mL, 98 mmol), palladium(II)acetate (750 mg, 3.30 mmol) and tri-ortho-tolylphosphine (2.0 g, 6.5 mmol) were stirred together in toluene (75 mL) at 100° C. for 5 hours. After cooling, the reaction was diluted with ethyl acetate (150 mL) and 4M aqueous potassium fluoride solution (90 mL), and stirred for 15 minutes. The mixture was filtered through Arbocel® and the organic phase was separated and concentrated in vacuo. The residue was then purified by column chromatography on silica gel eluting with diethyl ether:pentane, 0:100 to 25:75, followed by dichloromethane to give the title compound as a pale yellow oil in 94% yield (12.6 g). $^1$H NMR (400 MHz, CDCl$_3$): δ: 2.15 (3H, s), 3.61 (2H, s), 3.69 (5H, s), 7.10–7.13 (2H, m), 7.19 (1H, d), 7.30 (1H, t); LRMS ESI: m/z 229 [M+Na]$^+$ Preparation 19: Methyl [3-((2R)-2{[(1R)-1-phenyl-ethyl]amino}propyl)-phenyl]acetate hydrochloride

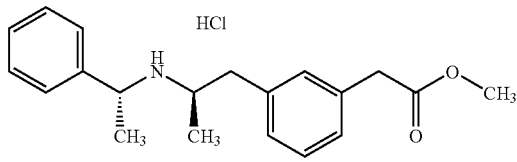

A solution of the product of preparation 18 (8.5 g, 41.2 mmol), (R)-α-methyl benzylamine (4.8 mL, 37.2 mmol), sodium triacetoxyborohydride (11.6 g, 56 mmol) and acetic acid (2.2 mL, 38 mmol) in dichloromethane (400 mL) was stirred at room temperature for 48 hours. The reaction mixture was quenched by addition of saturated sodium hydrogen carbonate solution (200 mL) and allowed to stir until effervescence ceased. The aqueous phase was separated and extracted with dichloromethane (100 mL). The combined organic solution was then dried over magnesium sulfate and concentrated in vacuo. Purification by column chromatography on silica gel, eluting with dichloromethane:methanol: ammonia, 99:1:0.1 to 95:5:0.5, gave a 4:1 mixture of diastereomers (R,R major) as a pale yellow oil (8.71 g). Treatment with hydrogen chloride (40 mL of a 1M solution in methanol, 40 mmol) followed by three successive crystallisations (diisopropylether/methanol) gave the title compound as a white crystalline solid in 50% yield, 5.68 g. $^1$H NMR (400 MHz, CD$_3$OD): δ: 1.18 (3H, d), 1.68 (3H, d), 2.60–2.66 (1H, m), 3.15–3.26 (1H, m), 3.25–3.30 (1H, m), 3.31 (3H, s), 3.62 (2H, s), 4.59 (1H, q), 6.99–7.02 (2H, m), 7.17 (1H, m), 7.25–7.28 (1H, m), 7.48–7.52 (5H, m) LRMS ESI m/z 312 [M+H]$^+$ Preparation 20: Methyl {3-[(2R)-2-aminopropyl]phenyl}acetate

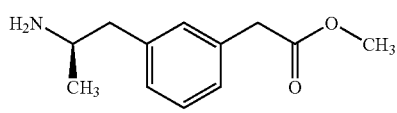

A solution of the product of preparation 19 (7.69 g, 22 mmol) and ammonium formate (6.94 g, 110 mmol) was heated to 75° C. in the presence of 20% palladium hydroxide-on-charcoal (2.00 g). After 90 minutes the reaction mixture was cooled to room temperature, filtered through Arbocel® and the filtrate concentrated in vacuo. The residue was partitioned between dichloromethane (100 mL) and 0.88 ammonia (100 mL) and the phases were separated. The aqueous phase was extracted with dichloromethane (100 mL) and the combined organic solution was dried over magnesium sulfate and concentrated in vacuo to afford the title compound as a colourless oil in quantitative yield (4.78 g). $^1$H NMR (400 MHz, CD$_3$OD): δ: 1.06 (3H, d), 2.57–2.67 (2H, m), 3.05–3.12 (1H, m), 3.63 (2H, s), 3.67 (3H, s), 7.09–7.13 (3H, m), 7.23–7.27 (1 H, t); LRMS ESI m/z 208 [M+H]$^+$ Preparation 21: Methyl (3(2R)-2-[(tert-butoxycarbonyl)amino]propyl} phenyl)acetate

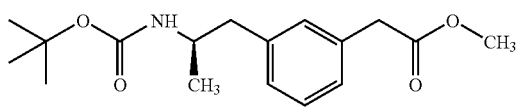

The title compound was prepared from the product of preparation 20 and di-tertbutyl dicarboxylate, using a method similar to that of preparation 6, as a yellow oil in 97% yield. $^1$H NMR (400 MHz, CD$_3$Cl$_3$): δ: 1.07 (3H, d), 1.43 (9H, s), 2.61 (1H, dd), 2.81 (1H, dd), 3.60 (2H, s), 3.69 (3H, s), 3.89 (1H, bs), 4.36 (1H, bs), 7.06–7.19 (3H, m), 7.22–7.27 (1H, m); LRMS APCI m/z 306 [M–H]$^-$ Preparation 22: (3-{(2r)-2-[(tert-butoxycarbonyl)amino]propyl}phenyl) acetic acid

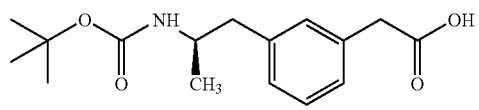

A mixture of preparation 21 (8.31 g, 27.1 mmol) and lithium hydroxide solution (1M in water, 54 mL, 54 mmol) in tetrahydrofuran (100 mL) was stirred at room temperature for 20 hours. The reaction mixture was then concentrated in vacuo and the aqueous residue was acidified to pH 2 with 2M hydrochloric acid. The mixture was then extracted with ethyl acetate (3×75 mL) and the combined organic solution was washed with brine (100 mL), dried over magnesium sulfate and concentrated in vacuo to afford the title compound as a yellow oil in 82% yield (6.50 g) $^1$H NMR(400 MHz, CD$_3$Cl$_3$): δ: 1.07(3H, d), 1.40(9H, s), 2.61(1H, dd), 2.77–2.88(1H, bs), 3.62 (2H, s), 3.89(1 H, bs), 4.39(1 H, bs), 7.07–7.16(3H, m), 7.22–7.27(1H, m); LRMS APCI m/z 292 [M–H]$^-$ Preparation 23: Benzyl (3-{(2R)-2-[(tert-butoxycarbonyl)amino]propyl}phenyl)acetate

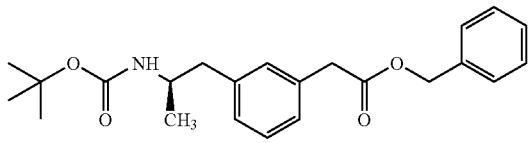

The product of preparation 22 (6.30 g, 21.5 mmol), 1-(3-dimethylaminopropyl)-3-ethylcarbodiimide hydrochloride (4.14 g, 21.5 mmol), 1-hydroxybenzotriazole hydrate (3.30 g, 21.5 mmol) and triethylamine (4.85 mL, 43 mmol) were stirred together in dichloromethane (100 mL) for 10 minutes at room temperature. Benzyl alcohol (2.2 mL, 21.5 mmol) was then added and the mixture was stirred at room temperature for 18 hours. The reaction mixture was then diluted with dichloromethane (50 mL), washed with sodium hydrogen carbonate solution (100 mL) and brine (100 mL), dried over magnesium sulfate and concentrated in vacuo to afford the title compound as a clear oil in 50% yield, 4.16 g. ¹H NMR (400 MHz, CD₃Cl₃): δ: 1.04 (3H, d), 1.44 (9H, s), 2.59 (1H, dd), 2.81 (1H, dd), 3.64 (2H, s), 3.87 (1H, bs), 4.34 (1H, bs), 5.13 (2H, s), 7.07–7.11(2H, m), 7.13(1H, bd), 7.22–7.27(1H, m), 7.29–7.38(5H, m); LRMS APCI m/z 382 [M−H]⁻

Preparation 24: Benzyl {3-[(2R)-2-aminopropyl]phenyl}acetate

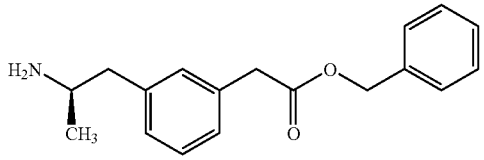

Hydrogen chloride (4M in dioxane, 5.43 mL, 21.72 mmol) was added to a solution of the product of preparation 23 (4.16 g, 10.86 mmol) in dioxane (50 mL) and the resulting solution stirred at room temperature for 72 hours. The solvent was removed in vacuo and the residue was dissolved in dichloromethane and washed with sodium hydrogen carbonate solution (50 mL) and brine (50 mL). The organic solution was then dried over magnesium sulfate and concentrated in vacuo to afford the title compound as a yellow oil in 93% yield (2.85 g). ¹H NMR (400 MHz, CD₃Cl₃): δ: 1.09(3H, d), 1.55(2H, bs), 2.48(1H, dd), 2.66 (1H, dd), 3.10–3.18(1H, m), 3.65(2H, s), 5.17(2H, s), 7.09–7.13(2H, m), 7.14–7.18(1H, bd), 7.24–7.38(6H, m); LRMS APCI m/z284 [M−H]⁻

Preparation 25: Benzyl (3-{(2R)-2-[((2R)-2-[4-(benzyloxy)-3-(formylamino)phenyl]-2-{[tert-butyl(dimethyl)silyl]oxy}ethyl)amino]-propyl}phenyl)acetate

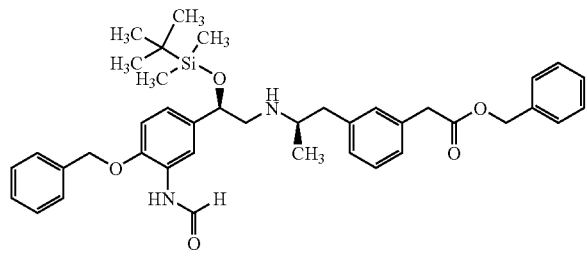

The title compound was prepared from the products of preparation 12 and preparation 24, using a similar method to that of preparation 13, as a brown oil in 25% yield.

LRMS APCI m/z 667 [M+H]⁺

Preparation 26: {3-[(2R)-2-({(2R)-2-{[tert-Butyl(dimethyl)silyl]oxy}-2-[3-(formylamino)-4-hydroxyphenyl]ethyl}amino)propyl]phenyl}acetic acid

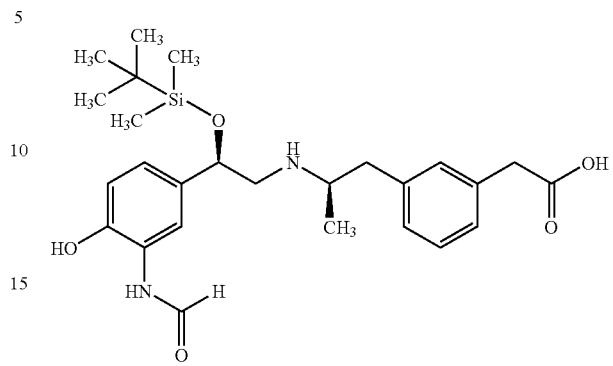

The product of preparation 25 (851 mg, 1.27 mmol) and 10% Pd/C (50 mg) were suspended in methanol and the mixture was stirred under 60 psi of hydrogen gas, at room temperature for 72 hours. The reaction mixture was then filtered through Filter aid® and the filtrate was concentrated in vacuo to afford the title product as a brown foam in 94% yield, 580 mg. ¹H NMR (400 MHz, CDCl₃): δ: −0.09 (3H, s), 0.08 (3H, s), 0.88 (9H, s), 1.12,1.24 (3H, 2xd), 2.07–2.82 (2H, m), 2.99 (1H, dd), 3.18 (1H, dd), 3.60 (2H, s), 4.16–4.22 (1H, m), 4.97–5.07 (1H, m), 6.87 (1H, d), 6.99–7.32 (6H, m), 7.93 (s), 8.17 (d), 8.33 (s); LRMS APCI m/z 487 [M+H]⁻

Preparation 27: 2-{3-[(2R)-2-({(2R)-2[tert-Butyl(dimethyl)silyl]oxy}-2-[3-(formylamino)-4-hydroxyphenyl]ethyl}amino)propyl]phenyl}-N-[4-(dimethyl amino)benzyl]acetamide

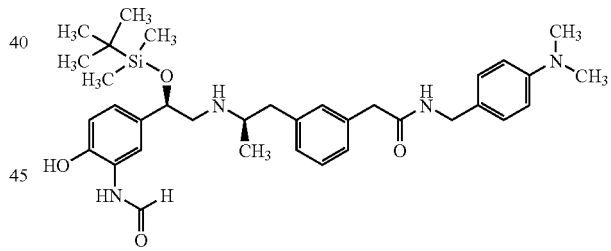

A mixture of the product of preparation 26 (100 mg, 206 μmol), hydroxybenzotriazole hydrate (32 mg, 206 μmol), 1-(3-dimethylaminopropyl)-3-ethylcarbodiimide hydrochloride (40 mg, 206 μmol) and triethylamine (58 μL, 412 μmol) in N,N-dimethylformamide (2 mL) was stirred at room temperature for 10 minutes. 4-(Dimethylamino)benzylamine (31 mg, 206 ∞mol) was then added and the mixture was stirred at room temperature for 20 hours. The solvent was then removed in vacuo and the residue was diluted with dichloromethane, washed with sodium hydrogen carbonate solution (20 mL) and brine (20 mL), dried over magnesium sulfate and concentrated in vacuo to afford the title compound as a brown gum in 10% yield, 131 mg. ¹H NMR (400 MHz, CD₃Cl₃): 0.17 (3H, s), 0.00 (3H, s), 0.83 (9H, s), 1.08 (3H, m), 2.80–3.00 (10H, m), 3.47 (1H, m), 3.66 (2H, m), 4.23 (2H, m), 5.48 (1H, m), 6.66 (1H, d), 6.70–7.23 (10H, m), 7.97 (m), 8.27 (s); LRMS APCI m/z 504 [M+H]⁻

Preparations 28 to 29:

The following compounds, of the general formula shown below were prepared from the product of preparation 26 and the appropriate amine, using a method similar to that described for preparation 27. The reactions were monitored by tlc analysis and were stirred at room temperature for 18–72 hours.

mixture and the methanol removed in vacuo. The resulting precipitate was filtered off and washed with water (20 mL) and a mixture of ethanol/diethyl ether, 20:80, to afford the title compound as a solid in 91% yield, 11.89. $^1$H NMR (400 MHz, CD$_3$OD) δ: 1.16 (3H, d), 1.62 (3H, d), 2.66–2.62 (1H, m), 3.13–3.26 (2H, m), 3.46 (2H, s), 4.48–4.56 (1H, q), 6.92 (1H, d), 7.19 (1H, s), 7.18–7.22 (2H, m), 7.45–7.52 (5H, m); LRMS ESI m/z 298 [M+H]$^+$

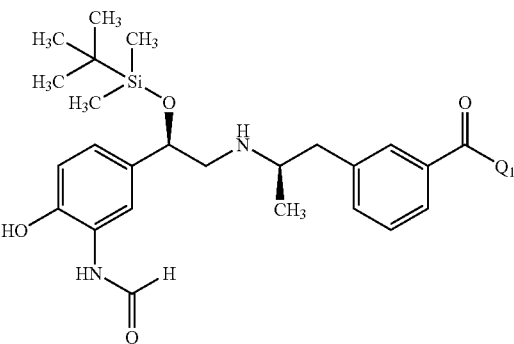

| No. | Q$_1$ | Data | Yield |
|---|---|---|---|
| 28 | CH3) | LRMS APCl m/z 632 [M − H]$^-$ | 99% |
| 29 | NH2) | LRMS APCl m/z 6618 [M − H]$^-$ | 99% |

Preparation 28: N-[4-(aminomethyl)phenyl]acetamide may be prepared as described in *J. Med. Chem,* 46, 3116; 2003

Preparation 29: 4-(aminomethyl)benzamide may be prepared as described in WO 02085860 p239

Preparation 30: [3-((2R)-2-{[(1R)-1-Phenylethyl]amino}propyl)phenyl]acetic acid

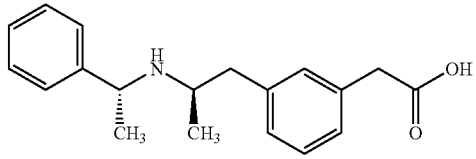

Lithium hydroxide solution (1M in water, 90 mL, 90 mmol) was added to a solution of the product of preparation 19 (13.50 g, 43.5 mmol) in methanol (200 mL) and the mixture was stirred at room temperature for 18 hours. 1M Hydrochloric acid (90 mL) was then added to the reaction Preparation 31: N-1-Adamantyl-2-[3-((2R)-2-{[(1R)-1-phenylethyl]amino}propyl)phenyl]acetamide

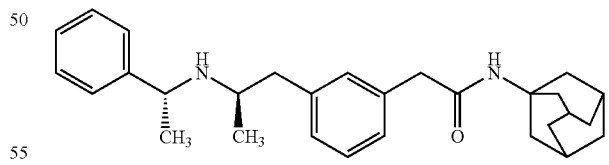

1-Adamantylamine (5.44 g, 36.0 mmol) and triethylamine (15 mL, 108 mmol) were added to a solution of the product of preparation 30 (10.7 g, 36.0 mmol) in dichloromethane (200 mL). 2-Chloro-1,3-dimethylimidazolidinum hexafluorophosphate (10.0 g, 36.0 mmol) was then added and the mixture was stirred at room temperature for 2 hours. The reaction mixture was washed with water and the organic solution was dried over magnesium sulfate and concentrated in vacuo. Purification of the residue by column chromatography on silica gel, eluting with dichloromethane:methanol:

0.88 ammonia, 95:5:0.5, afforded the product as a foam in quantitative yield, 17.6 g. ¹H NMR (400 MHz, CD₃OD) δ: 0.89 (3H, d), 1.35 (3H, d), 1.65–1.75 (6H, m), 1.98 (6H, m), 2.04 (3H, m), 2.37–2.42 (1H, dd), 2.65–2.74 (1H, m), 2.95–3.00 (1H, dd), 3.36 (2H, s), 3.98 (1H, q), 6.89 (1H, d), 6.98 (1H, s), 7.09 (1H, d), 7.17 (1H, t), 7.22–7.27 (1H, m), 7.30–7.38 (4H, m); LRMS ESI m/z 431 [M+H]⁺.

Preparation 32: N-1-Adamantyl-2-{3-[(2R)-2-aminopropyl]phenyl}-acetamide

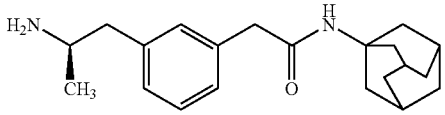

The title compound was prepared from preparation 31, using a similar method to that of preparation 20, as a solid in 92% yield. ¹H NMR (400 MHz, CD₃OD) δ: 1.09 (3H, d), 1.66–1.72 (6H, m), 2.00 (6H, m), 2.03 (3H, m), 2.58–2.70 (2H, m), 3.10–3.16 (1H, q), 3.40 (2H, s), 7.05–7.28 (4H, m); LRMS ESI m/z327 [M+H]⁺

Preparation 33: 2-(3-{(2R)-2-[((2R)-2-[3-(Acetylamino)-4-(benzyloxy)phenyl]-2-([tert-butyl(dimethyl)silyl]oxy}ethyl)amino]propyl}-phenyl)-N-1-adamantylacetamide

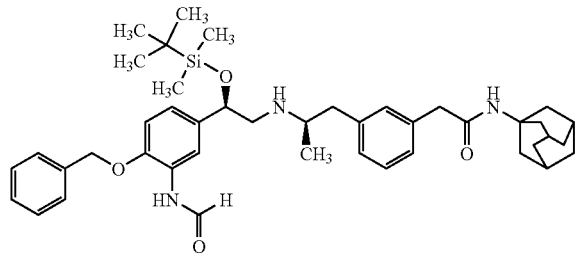

A mixture of the products of preparation 12 (696 mg, 1.5 mmol) and preparation 32 (978 mg, 3.0 mmol) in dichloromethane (0.5 mL) was heated at 90° C. for 5 minutes allowing the dichloromethane to evaporate. The reaction mixture was then heated as a melt at 90° C. for 18 hours before cooling to room temperature. The crude product was then purified by column chromatography on silica gel, eluting with dichloromethane:methanol:0.88 ammonia, 98:2:0.2, to afford the title compound as a pale foam in 59% yield, 630 mg. ¹H NMR (400 MHz, CD₃OD) δ: −0.18 (3H, s), 0.00 (3H, s), 0.83 (9H, s), 1.05–1.08 (d, 3H), 1.66–1.72 (6H, m), 2.00 (6H, m), 2.02 (3H, m), 2.52–2.71 (3H, m), 2.84–2.96 (2H, m), 3.36–3.41 (2H, m), 4.68–4.72 (1H, m), 5.20 (2H, s), 6.92–7.18 (6H, m), 7.30–7.50 (5H, m), 8.22 (m), 8.36 (s), 8.54 (s); LRMS ESI m/z 710 [M+H]⁺

Preparation 34: N-Adamantan-1-yl-2-(3-{2-[(2R)-2-({(2R)-2-(tert-butyldimethylsilanyloxy)-2-(3-formylamino-4-hydroxyphenyl)ethylamino]propyl}phenyl)acetamide

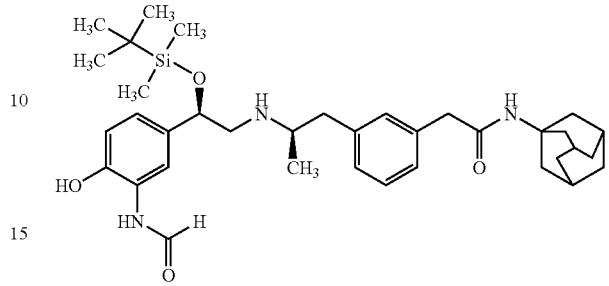

The title compound was prepared from the product of 33, using a similar method to that of preparation 20, as a clear foam in quantitative yield. ¹H NMR (400 MHz, CD₃OD) δ: −0.17 (3H, s), 0.00 (3H, s), 0.83 (9H, s), 1.04–1.06 (d, 3H), 1.69–1.70 (6H, m), 2.00 (6H, m), 2.03 (3H, m), 2.52–2.70 (3H, m), 2.88–2.94 (2H, m), 3.37–3.38 (2H, m), 4.64–4.69 (1H, m), 6.92–7.18 (6H, m), 8.00 (1H, d), 8.30 (s), 8.56 (s); LRMS ESI m/z 620 [M+H]⁺.

Preparation 35: 1-(3-Bromophenyl)-2-methylpropan-2-ol)

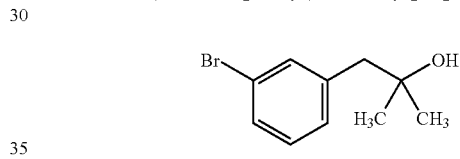

Methylmagnesium bromide (3M solution in diethyl ether, 51.6 mL, 155 mmol) was slowly added to a solution of 1-(3-bromo-phenyl)propan-2-one (15.0 g, 70 mmol) in dry diethyl ether (200 mL) at 0° C. and the mixture was stirred for 3 hours. The reaction mixture was then re-cooled to 0° C. and slowly quenched with saturated aqueous ammonium chloride solution. The organic solution was washed with brine, dried over sodium sulfate and concentrated in vacuo. The residual yellow oil was then purified by column chromatography on silica gel eluting with dichloromethane: pentane:methanol, 90:5:5, to afford a pale yellow oil in 83% yield, 13.26 g. ¹H NMR (400 MHz, CDCl₃) δ: 1.22 (6H, s), 1.42 (1H, bs), 2.74 (2H, s), 7.15 (2H, m), 7.40 (2H, m)

Preparation 36: N-[2-(3-Bromophenyl)-1,1-dimethylethyl]-2-chloroacetamide

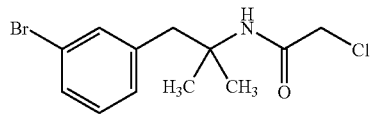

Chloroacetonitrile (6.63 mL, 105 mmol) was added to a stirred solution of the product of preparation 35 (12.0 g, 52.0 mmol) in acetic acid (25 mL) at room temperature. The resulting solution was cooled to 0° C. and concentrated sulfuric acid (25 mL) was added whilst the temperature was maintained below 10° C. The resulting solution was left to stir for 1 hour and was then poured onto ice and basified by the addition of solid potassium carbonate. The product was extracted with ethyl acetate (2×500 mL) and the combined organic solution was washed with water (50 mL), dried over sodium sulfate and the concentrated in vacuo to afford the title compound as an orange solid in quantitative yield, 16.08 g. ¹H NMR (400 MHz, CDCl₃) δ: 1.37 (6H, s), 3.02 (2H, s), 3.94 (2H, s), 6.17 (1H, bs), 7.08–7.03 (1H, d), 7.10–7.13 (1H, t), 7.26 (1H, s), 7.39–7.32 (1H d,); LRMS ESI m/z 306 [M+H]⁺; Microanalysis: C₁₂H₁₅BrClNO requires: C, 47.32; H, 4.96; N, 4.60. found C, 47.26; H, 4.87; N, 4.65.

Preparation 37:
2-(3-Bromophenyl)-1,1-dimethylethylamine

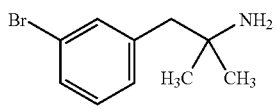

A solution of the product of preparation 36 (32.0 g, 105 mmol), thiourea (9.60 g, 126 mmol) and acetic acid (50 mL) in ethanol (250 mL) was heated to reflux overnight. The reaction mixture was cooled to room temperature and filtered. The filtrate was concentrated in vacuo, basified using aqueous sodium hydroxide solution (1M, 450 mL) and extracted with dichloromethane (2×500 mL). The combined organic solution was washed with brine (50 mL), dried over sodium sulfate and concentrated in vacuo to afford the title compound as a black oil in 96% yield, 23 g. ¹H NMR (400 MHz, CDCl₃) δ: 1.12 (6H, s), 1.84 (2H, bs), 2.62 (2H, s), 7.16–7.08 (2H, m), 7.36–7.32 (2H, m); LRMS ESI m/z 228 [M+H]⁺

Preparation 38:
[2-(3-Bromophenyl)-1,1-dimethylethyl]carbamic acid tert-butyl ester

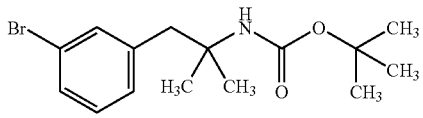

The product of preparation 37 (5.0 g, 22 mmol) was treated with di-tert-butyl dicarbonate (5.26 g, 24 mmol) in dichloromethane (50 mL) and stirred for 20 hours. The reaction mixture was washed with water (50 mL) and the combined organic solution was dried over sodium sulfate and concentrated in vacuo. The crude material was purified using a cation exchange column (methanol followed by 2M ammonia in methanol), followed by purification by flash column chromatography on silica gel eluting with dichloromethane to afford the title compound as a brown oil in quantitative yield, 7.23 g. ¹H NMR (400 MHz, CDCl₃) δ: 1.27 (6H, s) 1.50 (9H, s), 2.97 (2H, s), 4.24 (1H, bs), 7.05 (1H, d), 7.15–7.11 (1H, t), 7.30 (1H, d), 7.35 (1H, d); LRMS ESI m/z 350 [M+NH₄]⁺

Preparation 39: Benzyl 3-{(2-[(tert-butoxycarbonyl)amino]-2-methylpropyl}benzoate

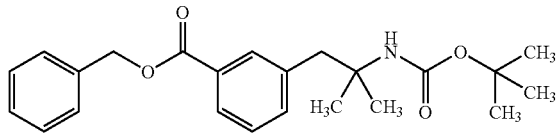

A solution of the product of preparation 38 (3.9 g, 12 mmol), [1,1'-bis(diphenylphosphino)ferrocene]dichloropalladium(II) (1.00 g, 1.3 mmol) and triethylamine (3.3 mL, 24 mmol) in benzyl alcohol (60 mL) was heated to 100° C. under 100 psi carbon monoxide for 5 hours. The cooled reaction mixture was then filtered through Arbocel® and the filtrate concentrated in vacuo. The residue was dissolved in ethyl acetate and washed with sodium hydrogen carbonate solution (50 mL) and brine (2×50 mL). The organic solution was then dried over sodium sulfate and concentrated in vacuo to give a dark oil. This oil was purified by column chromatography on silica gel, eluting with hexane:ethyl acetate 100:0 to 84:16, to afford the title compound as a pale yellow oil in 61% yield, 2.81 g. ¹H NMR(400 MHz, CDCl₃) δ: 1.25(6H, s), 1.45(9H, s), 3.05(2H, s), 4.22(1H, bs), 5.35(2H, s), 7.32–7.48(7H, m), 7.86(1H, s), 7.93–7.97(1H, m)

Preparation 40: Benzyl 3-(2-amino-2-methylpropyl)benzoate hydrochloride

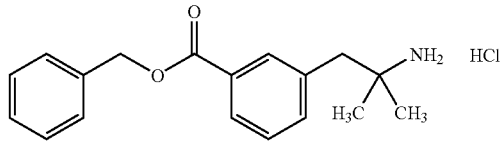

The title compound was prepared from the product of preparation 39, using a method similar to that of preparation 24, as a white solid in 91% yield. ¹H NMR (400 MHz, CD₃OD) δ: 1.33 (6H, s), 2.98 (2H, s), 5.37 (2H, s), 7.31–7.53 (7H, m), 7.93 (1H, s), 8.00–8.04 (1H, m); LRMS APCI m/z 284 [M+H]⁺

Preparation 41: Benzyl 3-{2-[((2R)-2-[4-(benzyloxy)-3-(formylamino)phenyl]-2-([tert-butyl(dimethyl)silyl]oxy}ethyl)amino]-2-methylpropyl}benzoate

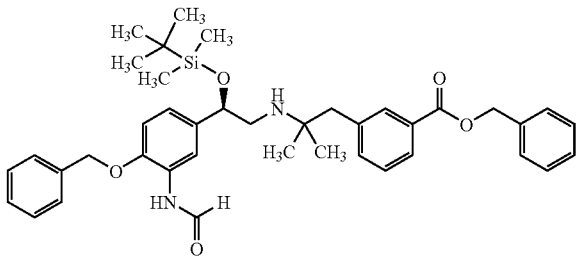

A mixture of the product of preparation 40 (1.81 g, 6.38 mmol), preparation 12 (2.96 g, 6.38 mmol) and potassium carbonate (1.76 g, 12.8 mmol) in dimethylsulfoxide (10 mL) was heated at 95° C. for 40 hours. The cooled reaction mixture was then diluted with water (250 mL) and extracted with ethyl acetate (3×50 mL). The combined organic solution was washed with sodium hydrogen carbonate solution (50 mL) and brine (2×50 mL), dried over sodium sulfate and concentrated in vacuo to give an orange oil. This oil was purified by column chromatography on silica gel, eluting with dichloromethane:hexane, 50:50, followed by dichloromethane:methanol, 100:0 to 98:2. The appropriate fractions were evaporated under reduced pressure and the residue was further purified by column chromatography on silica gel, eluting with dichloromethane:methanol, 100:0 to 98:2, to give a yellow gum. The gum was azeotroped with diethyl ether (x3) to afford the title compound as a yellow gum in 20% yield, 0.83 g. $^1$H NMR (400 MHz, CDCl$_3$): δ: -0.15 to -0.17 (3H, m), -0.03 (3H, s), 0.79-0.82 (9H, s), 1.01 (3H, s), 1.04 (3H, s), 2.62-2.86 (4H, m), 4.66-4.74 (1H, m), 5.06-5.07 (2H, m), 5.36 (2H, s), 6.88 (1H, d), 7.01-7.05 (1H, m), 7.27-7.50 (12H, m), 7.74 (1H, m), 7.87-7.96 (2H, m), 8.39 (s), 8.40 (s), 8.76 (s), 8.78 (s); LRMS APCI m/z 667 [M+H]$^-$ Preparation 42: 3-[2-({(2R)-2-[tert-Butyl(dimethyl)silyl]oxy}-2-[3-(formylamino)-4-hydroxyphenyl]ethyl}amino)-2-methylpropyl]benzoic acid

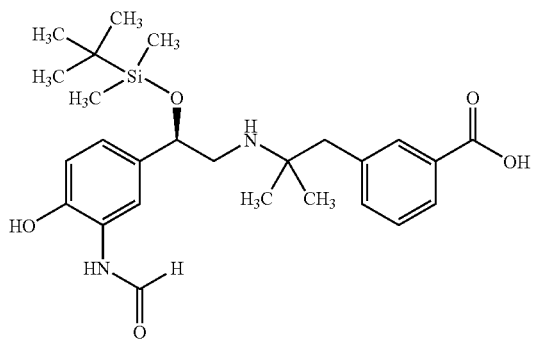

The title compound was prepared from the product of preparation 41, using a method similar to that of 26. The crude product was then azeotroped with diethyl ether (x3) to afford the title compound as a pale yellow solid in 97% yield. $^1$H NMR (400 MHz, CD$_3$OD): δ: -0.12 (3H, s), 0.05 (3H, s), 0.81 (9H, s), 1.24 (6H, s), 2.98 (2H, dd), 3.26-3.30 (2H, m), 4.91 (1H, t), 6.89 (1H, d), 7.02 (1H, m), 7.37-7.49 (2H, m), 7.85 (1H, bs), 7.93-7.96 (1H, d), 8.11 (s, 1H), 8.32 (s), 8.61 (s); LRMS ESI m/z 487 [M+H]$^-$ Preparation 43:(4-Hydroxy-2,5-dimethylphenyl)acetonitrile

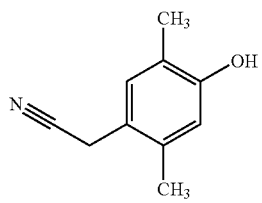

A solution of (4-methoxy-2,5-dimethylphenyl)acetonitrile (0.5 g, 2.9 mmol) in dichloromethane (10 mL) was cooled to -80° C. and treated with borontribromide (1M in dichloromethane, 14.3 mL, 14.3 mmol). The reaction mixture was stirred at -80° C. for a further 30 minutes and then was allowed to warm to room temperature over a period of 2 hours. The reaction mixture was quenched with saturated sodium hydrogen carbonate solution (20 mL) and the organic layer was separated. The organic solution was washed with brine (20 mL), dried over sodium sulfate and the concentrated in vacuo to afford a pale brown solid. Purification by column chromatography on silica gel, eluting with ethyl acetate:pentane 20:80 to 33:67, afforded the title compound as a colourless solid in 60% dispersion in mineral oil yield, 0.28 g. $^1$H NMR (400 MHz, CD$_3$OD) δ: 2.13 (3H, s), 2.23 (3H, s), 3.66 (2H, s), 6.60 (1H, s), 6.98 (1H, s); LRMS ESI m/z 160 [M-H]$^-$ Preparation 44: (4-Hydroxy-2,3-dimethyl-phenyl)acetonitrile

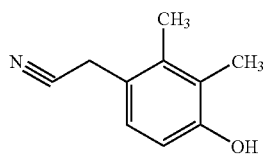

The title compound was prepared from (4-methoxy-2,3-dimethyl-phenyl)acetonitrile using a similar method to that of preparation 43, as a colourless solid in 94% yield. $^1$H NMR (400 MHz, CDCl$_3$) δ: 2.20(3H, s), 2.24(3H, s), 3.62(2H, s), 6.64(1 H, d), 7.03(1 H, d); LRMS APCI m/z 160 [M-H]$^-$ Preparation 45: (4-Hydroxy-3-methylphenyl)acetonitrile

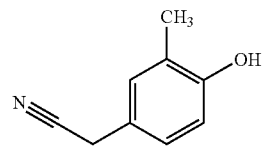

The title compound was prepared from (4-methoxy-3-methylphenyl)acetonitrile using a similar method to that of preparation 43, as a pale yellow solid. $^1$H NMR (400 MHz, CDCl$_3$) δ: 2.25 (3H, s), 3.65 (2H, s), 4.98 (1H, bs), 6.76 (1H, d), 7.01 (1H, d), 7.07 (1 H, s); LRMS ESI m/z 146 [M-H]$^-$ Preparation 46: 4-(2-Aminoethyl)-2,5-dimethylphenol

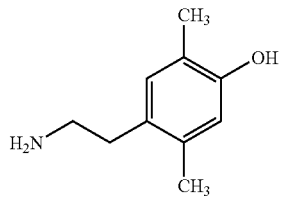

A solution of the product of preparation 43 (0.28 g, 1.74 mmol) in ethanol (15 mL) was hydrogenated at 60 psi over Raney Nickel® (0.1 g, 50% w/w) for 16 hours. The reaction mixture was then filtered and the solvent was removed in vacuo. The residue was purified using a cation exchange resin, eluting with methanol and then 1M ammonia in methanol to afford the title compound as a colourless oil. ¹HNMR(400 MHz, CD₃OD) δ: 2.11 (3H, s), 2.19 (3H, s), 2.63–2.67 (2H, m), 2.72–2.76 (2H, m), 6.54 (1H, s), 6.81 (1H, s); LRMS ESI m/z 166 [M+H]⁺

Preparation 47:
4-(2-Amino-ethyl)-2,3-dimethyl-phenol

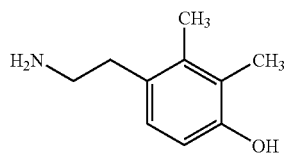

The title compound was prepared from the product of preparation 44 using a similar method to that of preparation 46, as a colourless solid in 95% yield. ¹H NMR (400 MHz, CDCl₃) δ: 6.78 (1H, d), 6.55 (1H, d), 2.75–2.68 (4H, m), 2.19 (3H, s), 2.12 (3H, s); LRMS APCI m/z 166 [M+H]⁺

Preparation 48: 4-(2-Aminoethyl)-2-methylphenol

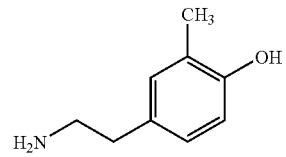

The title compound was prepared from the product of preparation 45, using a similar method to that of preparation 46, as a colourless oil. ¹HNMR(400 MHz, CD₃OD) δ: 2.15 (3H, s), 2.60–2.64 (2H, m), 2.79–2.83 (2H, m), 6.66 (d, 1H), 6.82 (1H, d), 6.90 (1H, s); LRMS ESI m/z 152 [M+H]⁺

Preparation 49: tert-Butyl (3-iodobenzyl)carbamate

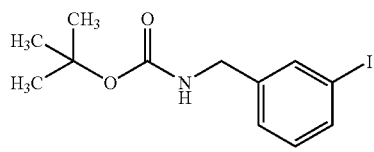

A suspension of 3-iodobenzylamine hydrochloride (4.95 g, 18.4 mmol) in dichloromethane (100 mL) was treated with triethylamine (3.1 mL, 22 mmol) and di-tert-butyl dicarbonate (4.40 g, 20 mmol) and the resulting solution stirred at room temperature for 1.5 hours. The reaction mixture was then washed with 2M hydrochloric acid (30 mL), water (30 mL), dried over sodium sulfate and concentrated in vacuo to afford the title compound as a colourless solid in quantitative yield, 6.43 g. ¹HNMR (400 MHz, CDCl₃) δ: 1.46 (9H, s), 4.21–4.30 (2H, m), 4.79–4.89 (1H, bs), 7.06 (1H, dd), 7.25 (1H, d), 7.60 (1H, d), 7.63 (1 H, s); LRMS ESI m/z 332 [M–H]⁻

Preparation 50: tert-Butyl [(4'-hydroxybiphenyl-3-yl)methyl]carbamate

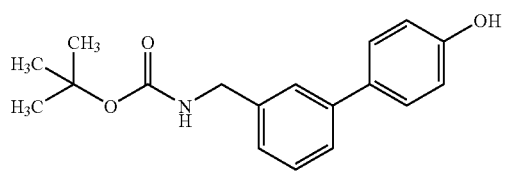

A solution of the product of preparation 49 (0.75 g, 2.25 mmol), 4-hydroxy phenylboronic acid (0.62 g, 4.50 mmol) and 1,1'-bis(diphenylphosphino)ferrocenyl palladium(II) chloride (0.11 g, 0.14 mmol) in N,N-dimethylformamide (14 mL) was treated with 2M aqueous sodium carbonate solution (4 mL) and the resulting mixture was heated at 80° C. for 16 hours. The solvent was removed in vacuo and the residue was purified by column chromatography on silica gel, eluting with ethyl acetate: pentane, 25:75, to afford the title compound as a pale pink crystalline solid in quantitative yield, 0.73 g. ¹H NMR (400 MHz, CDCl₃) δ: 1.47 (9H, s), 4.33–4.41 (2H, m), 4.87–4.94 (1 H, bs), 6.89 (2H, d), 7.21 (1 H, d), 7.37 (1 H, dd), 7.43–7.45 (4H, m); LRMS ESI m/z 298 [M–H]⁻

Preparation 51: 3'-(Aminomethyl)biphenyl-4-ol hydrochloride

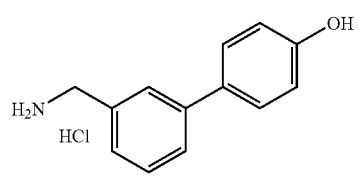

The product of preparation 50 (0.73 g, 2.43 mmol) was treated with 4M hydrochloric acid in dioxan (6.1 mL, 24.3 mmol) and the resulting solution allowed to stir at room temperature for 3 hours. The reaction mixture was then concentrated in vacuo to afford the title compound as a colourless solid. ¹H NMR (400 MHz, CD₃OD) δ: 4.17 (2H, s), 6.87 (2H, d), 7.34 (1H, d), 7.45–7.50 (3H, m), 7.61 (1H, d), 7.65 (1h, s); LRMS ESI m/z 198 [M–H]⁻

Preparation 52: 2-Hydroxy-1-naphthamide

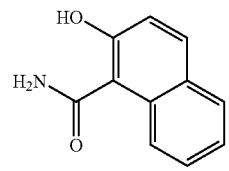

A solution of 2-hydroxy-1-napthoic acid (5.0 g, 26.6 mmol), 1-(3-dimethylaminopropyl)-3-ethylcarbodiimide hydrochloride (5.6 g, 29.2 mmol), and 1-hydroxybenzotriazole (3.95 g, 29.2 mmol) in tetrahydrofuran (70 mL) was stirred at room temperature for 30 minutes prior to the addition of 0.88 ammonia (6 mL). The resulting suspension was stirred at room temperature for 2 hours. The reaction mixture was then filtered, and the filtrate was diluted with water (80 mL) and extracted with ethyl acetate (4×80 mL). The combined organic extracts were washed with water (2×50 mL) and brine (50 mL), dried over sodium sulfate and concentrated in vacuo to give an orange oil. Purification of the oil by column chromatography on silica gel, eluting with dichloromethane:methanol:0.880 ammonia, 95:5:0.5, afforded the title compound as a pink solid in 37% yield, 1.83 g. $^1$HNMR(400 MHz, CDCl$_3$) δ: 6.11–6.35(2H, bs), 7.17(1H, d), 7.36(1H, dd), 7.54(1H, dd), 7.79(1H, d), 7.84 (1H, d), 8.22(1 H, d), 11.70–11.88(1 H, bs); LRMS ESI m/z 186 [M–H]$^-$ Preparation 53:
3,5-Dichloro-N-ethyl-2-hydroxybenzamide

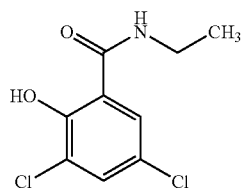

The title compound was prepared from 3,5-dichloro-2-hydroxybenzoic acid and ethylamine, using a similar method to that of preparation 52, to afford the title compound as a pale yellow solid. $^1$HNMR (400 MHz, CDCl$_3$) δ: 1.28 (3H, t), 3.47–3.54 (2H, m), 6.29–6.36 (1H, bs), 7.27 (1H, d), 7.48 (1H, d); LRMS ESI m/z 232 [M–H]$^-$ Preparation 54:
4-(Aminomethyl)-2,6-dimethylphenol hydrochloride

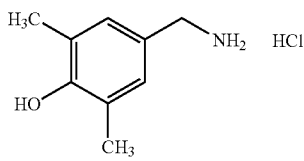

A solution of borane in tetrahydrofuran (1M in tetrahydrofuran, 27.1 mL, 27.1 mmol) was added dropwise to a solution of 3,5-dimethyl-4-hydroxybenzonitrile (1.0 g, 6.79 mmol) in tetrahydrofuran (70 mL) and the resulting solution was heated under reflux for 16 hours. The reaction mixture was cooled to room temperature, treated with 6N hydrochloric acid (20 mL) and heated under reflux for a further 30 minutes. The reaction mixture was then cooled to room temperature and the solvent was removed in vacuo. The residue was purified using a strong cation exchange resin eluting with methanol followed by 2M ammonia in methanol, to give an orange oil. This oil was then treated with 1M hydrogen chloride in methanol (20 mL) and the reaction mixture was concentrated in vacuo to afford the title compound as a pale yellow solid in quantitative yield, 1.12 g. $^1$HNMR (400 MHz, CDCl$_3$) δ: 2.22 (6H, s), 3.75 (2H, s), 6.90 (2H, s).

Preparation 55: 2-(Aminomethyl)-4-chlorophenol hydrochloride

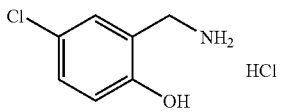

The title compound was prepared from 5-chloro-2-hydroxybenzonitrile, using a method similar to that described for preparation 54. $^1$HNMR (400 MHz, CDCl$_3$) δ: 4.08 (2H, s), 6.87 (1H, d), 7.27 (1H, d), 7.35 (1H, s); LRMS APCI m/z 156 [M–H]$^-$ Preparation 56: 4'-(Aminomethyl)biphenyl-4-ol hydrochloride

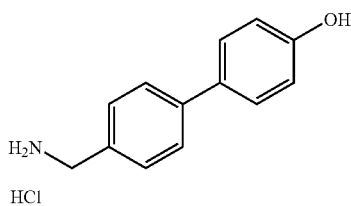

The title compound was prepared from 4'-hydroxybiphenyl-4-carbonitrile, using a method similar to that of preparation 54. $^1$HNMR (400 MHz, CD$_3$OD) δ: 4.10 (s, 2H), 6.83 (d, 2H), 7.44–7.46 (m, 4H), 7.60 (d, 2H).

Preparation 57: 1-(Aminomethyl)-2-naphthol

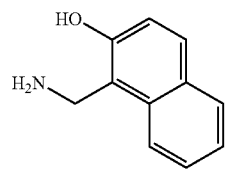

A solution of borane in tetrahydrofuran (19.23 mL of a 1M solution, 19.23 mmol) was added dropwise to a solution of the amide from preparation 52 (0.90 g, 4.81 mmol) in tetrahydrofuran (10 mL) and the reaction was then heated under reflux for 2 hours. The solution was cooled, treated with 6M hydrochloric acid (10 mL) and heated under reflux for a further 2 hours. The resulting suspension was cooled to room temperature and the pH was adjusted to pH 9 by addition of 0.88 ammonia and extracted with ethyl acetate (3×50 mL). The combined organic solution was washed with brine (20 mL), dried over sodium sulfate and concentrated in vacuo. Purification of the residue by column chromatography on silica gel, eluting with dichloromethane:methanol: 0.88 ammonia, 95:5:0.5 to 90:10:1, afforded the title compound as a pink solid in 23% yield, 0.19 g. $^1$H NMR (400 MHz, CD$_3$OD) δ: 4.41 (2H, s), 7.07 (1H, d), 7.23 (dd, 1H), 7.43 (1H, dd), 7.66 (1H, d), 7.72 (1H, d), 7.87 (1H, d); LRMS ESI m/z 174 [M+H]$^+$

Preparation 58:
2,4-Dichloro-6-[(ethylamino)methyl]phenol

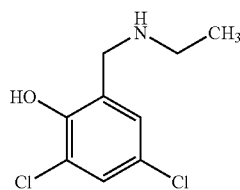

A solution of the product of preparation 53 (0.77 g, 3.29 mmol) in tetrahydrofuran (10 mL) was cooled to 0° C. and treated with borane-tetrahydrofuran complex (1M in tetrahydrofuran, 9.9 mL, 9.9 mmol). The resulting solution was allowed to warm to room temperature over 20 minutes and was then heated under reflux for 16 hours. The reaction mixture was cooled to 0° C. and quenched by addition of methanol. The resulting solution was allowed to warm to room temperature over 2 hours and was then concentrated in vacuo. The residue was dissolved in dichloromethane (40 mL) and washed with water (2×10 mL), brine (10 mL), dried over sodium sulfate and reduced in vacuo to give a colourless oil. Purification of the oil by column chromatography on silica gel, eluting with methanol:dichloromethane, 2:98 to 5:95 afforded the title compound as a colourless solid in 74% yield, 0.53 g. $^1$HNMR (400 MHz, CDC$_3$) δ: 1.17 (3H, t), 2.72 (2H, q), 3.98 (2H, s), 6.86 (1H, d), 7.23 (1H, d).

Preparations 59 to 68:

The following compounds, of the general formula shown below were prepared from the product of preparation 42 and the appropriate amine, using a method similar to that described for preparation 27. The reactions were monitored by TLC analysis and were stirred at room temperature for 18–72 hours.

| No. | Q$_1$ | Data | Yield |
|---|---|---|---|
| 59 | 4-Cl-C$_6$H$_4$-CH$_2$CH$_2$-NH- | $^1$H NMR (400MHz, CD$_3$OD) δ: −0.19 (3H, s), −0.04(3H, s), 0.78(9H, s), 1.08(3H, s), 1.10 (3H, s), 2.65–2.85(4H, m), 2.89(2H, t), 3.57 (2H, t), 4.67(1H, dd), 6.79(1H, d), 6.93(1H, dd), 7.21–7.37(6H, m), 7.59–7.65(2H, m), 8.08(1H, d), 8.29(s); LRMS ESI m/z 624 [M + H]$^+$ | 21% |
| 60 | 2,3-dimethyl-4-hydroxyphenyl-CH$_2$CH$_2$-NH- | $^1$H NMR(400MHz, CDCl$_3$) δ: −0.23(3H, s), −0.09(3H, s), 0.71(9H, s), 1.06(3H, s), 1.08 (3H, s), 2.18(3H, s), 2.26(3H, s), 2.60–2.82 (4H, m), 2.90–2.94(2H, m), 3.61–3.71(2H, m), 4.61–4.65(1H, m), 6.29–6.33(1H, m), 6.62–6.64(1H, m), 6.85–6.89(2H, m), 6.96(1H, d), 7.18(1H, s), 7.27–7.32(2H, m), 7.40–7.42(1H, m), 7.78(1H, s), 8.23(1H, s), 9.62(1H, bs) LRMS APCl m/z 634 [M − H]$^-$ | 56% |
| 61 | 4'-hydroxybiphenyl-3-yl-CH$_2$-NH- | LRMS APCl m/z 668 [M + H]$^+$ | 88% |

-continued

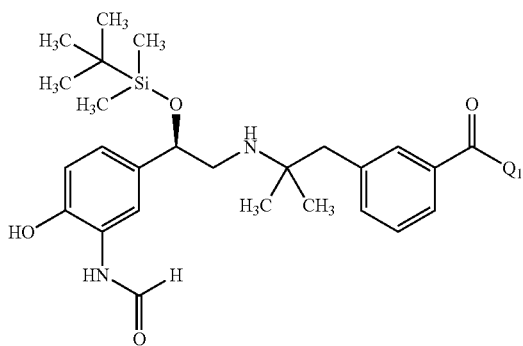

| No. | Q₁ | Data | Yield |
|---|---|---|---|
| 62 | (4'-hydroxybiphenyl-4-ylmethyl)NH— | LRMS APCl m/z 668 [M + H]⁺ | 48% |
| 63 | 2-(4-hydroxy-2,5-dimethylphenyl)ethyl-NH— | LRMS APCl m/z 634 [M + H]⁺ | 77% |
| 64 | 2-(3-hydroxy-4-methylphenyl)ethyl-NH— | LRMS APCl m/z 620 [M + H]⁺ | 96% |
| 65 | (2-hydroxynaphthalen-1-ylmethyl)NH— | LRMS APCl m/z 642 [M + H]⁺ | 91% |
| 66 | (4-hydroxy-3,5-dimethylbenzyl)NH— | LRMS APCl m/z 620 [M + H]⁺ | 95% |
| 67 | (3,5-dichloro-2-hydroxybenzyl)NH— | LRMS APCl m/z 660 [M + H]⁺ | 89% |
| 68 | (6-hydroxynaphthalen-2-ylmethyl)NH— | LRMS APCl m/z 642 [M + H]⁺ | 91% |

Preparation 60: purified by column chromatography using a 12 g Redisep® cartridge, eluting with dichloromethane: methanol: 0.88 ammonia, 96:4:0.3

Preparation 62: was further azeotroped with diethyl ether (×3) to afford the desired product Preparation 68: 6-(aminomethyl)-2-naphthalenol may be prepared as described in US20040204455, p 19

Preparation 69: 3-[2-({(2R)-2-{[tert-Butyl(dimethyl)silyl]oxy}-2-[3-(formyl amino)-4-hydroxyphenyl]ethyl}amino)-2-methylpropyl]-N-[2-(4-hydroxyphenyl)-2-methylpropyl]benzamide

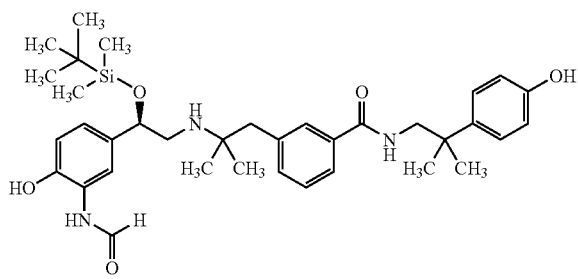

4-(2-Amino-1,1-dimethylethyl)phenol hydrochloride (*Acta Chem. Scand.* 8, 1203, 1207; 1954), (41 mg, 0.21 mmol) was added to a mixture of the product of preparation 42 (100 mg, 0.21 mmol), O-(1H-benzotriazol-1-yl)-N,N,N',N'-tetramethyluronium hexafluorophosphate (78 mg, 0.21 mmol) and triethylamine (35 µL, 0.4 mmol) in N,N-dimethylformamide (3 mL) and the mixture was stirred for 18 hours at room temperature. The solvent was then removed in vacuo and the residue was taken up in ethyl acetate and washed with saturated sodium hydrogen carbonate solution (3×20 mL) and brine (3×20 mL). The organic solution was then dried over sodium sulfate and concentrated in vacuo to afford the title compound as a brown foam in 54% yield. LRMS APCI m/z 634 [M+H]+

Preparations 70 to 76:

The following compounds, of the general formula shown below were prepared from the product of preparation 42 and the appropriate amine, using a method similar to that described for preparation 69. The reactions were monitored by TLC analysis and were stirred at room temperature for 18–72 hours.

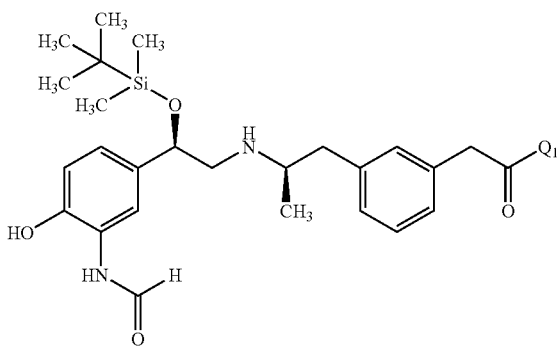

| No. | Q1 | Data | Yield |
|---|---|---|---|
| 70 | ![structure: HN-CH2-biphenyl-OH] | LRMS APCI m/z 668 [M + H]+ | 96% |
| 71 | ![structure: HN-CH2-(3,5-dimethyl-4-hydroxyphenyl)] | LRMS APCI m/z 620 [M + H]+ | 89% |
| 72 | ![structure: HN-CH2-(2-hydroxynaphthalen-1-yl)] | LRMS APCI m/z 642 [M + H]+ | 84% |

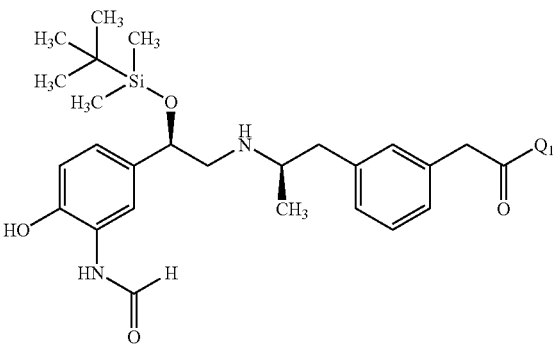

| No. | Q₁ | Data | Yield |
|---|---|---|---|
| 73 | (HN-CH2- group attached to phenyl with Cl and OH) | LRMS APCl m/z 626 [M + H]⁺ | 96% |
| 74 | (HN-CH2- group attached to phenyl with 2 Cl and OH) | LRMS APCl m/z 660 [M + H]⁺ | 83% |
| 75 | (HN-CH2- group attached to naphthyl with OH) | LRMS APCl m/z 642 [M + H]⁺ | 99% |
| 76 | (HN-CH2- group attached to biphenyl with OH) | LRMS APCl m/z 668 [M + H]⁺ | 80% |

Preparation 77: Diethyl 2,2'-(1,3-phenylene)diacetate

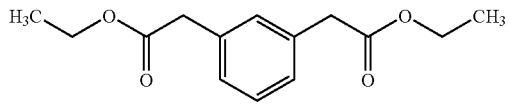

Acetyl chloride (12.5 mL, 175 mmol) was added to a suspension of 2,2'-(1,3-phenylene)diacetic acid (50.0 g, 260 mmol) in ethanol (500 mL) and the resulting solution was heated under reflux for 16 hours. The reaction was then cooled to room temperature and the solvent was removed in vacuo. The residue was partitioned between saturated aqueous sodium hydrogen carbonate solution (300 mL) and ethyl acetate (500 mL). The organic phase was separated and washed with water (200 mL) and brine (300 mL), dried over sodium sulfate and the concentrated in vacuo to afford the title compound as a pale yellow oil in quantitative yield, 63.5 g. ¹HNMR (CDCl₃, 400 MHz) δ: 1.31 (6H, t), 3.65 (4H, s), 4.20 (4H, q), 7.24–7.36 (4H, m); LRMS ESI m/z 251 [M+H]⁺

Preparation 78: [3-(2-Oxo-propyl)-phenyl]-acetic acid ethyl ester

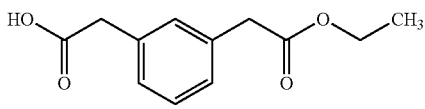

A solution of the diester from preparation 77 (44.3 g, 177 mmol) and 2,2'-(1,3-phenylene)diacetic acid (59.2 g, 308 mmol) in ethanol (24 mL) and dioxan (290 mL) was treated dropwise with 12M hydrochloric acid (4.9 mL, 58.8 mmol). The reaction mixture was stirred under reflux for 18 hours, cooled to room temperature and concentrated in vacuo. The reaction mixture was then diluted with toluene (125 mL) and the resulting slurry was filtered. The filtrate was concentrated in vacuo and the residue was taken up in water and basified with sodium bicarbonate until pH neutral. The mixture was diluted with ethyl acetate (200 mL) and the organic layer was separated and washed with sodium hydrogen carbonate solution (5×30 mL) and brine (50 mL). The combined aqueous extracts were acidified to pH 3 with 6M hydrochloric acid and extracted with diethyl ether (3×30 mL). The combined organic solution was dried over magnesium sulphate and concentrated in vacuo. Trituration of the residue with pentane afforded the title compound as a colourless solid in 27% yield, 10.8 g. $^1$HNMR (CD$_3$OD, 400 MHz) δ: 1.25 (3H, t), 3.60 (2H, m), 3.63 (2H, m), 4.15 (2H, q), 7.18–7.32 (4H, m); LRMS ESI: m/z 245 [M+Na]$^+$ Preparation 79:
[3-(2-Hydroxy-2-methyl-propyl)-phenyl]-acetic acid

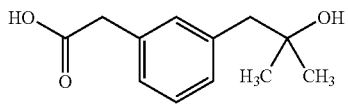

Methyl magnesium chloride (51 mL of a 3M solution in tetrahydrofuran, 153 mmol) was added dropwise to a stirred solution of the product of preparation 78 (11.6 g, 51 mmol) (International Journal of Peptide and Protein Research, 1987, 29(3), 331) in tetrahydrofuran (300 mL) at 0° C. The reaction was then allowed to warm to room temperature overnight with the formation of a thick white precipitate and then water (50 mL) and 2N hydrochloric acid (80 mL) were cautiously added. The aqueous layer was separated and extracted with ethyl acetate (2×300 mL). The combined organic solution was washed with brine (50 mL), dried over sodium sulfate and concentrated in vacuo to afford the title compound as a golden oil in quantitative yield, 11.2 g. $^1$HNMR (CDCl$_3$, 400 MHz) δ: 1.22 (6H, s), 2.75 (2H, s), 3.63 (2H, s), 7.12–7.30 (4H, m); LRMS ESI m/z 209 [M+H]$^+$ Preparation 80: {3-[2-(2-Chloro-acetylamino)-2-methyl-propyl]-phenyl}-acetic acid

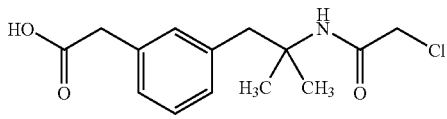

2-Chloroacetonitrile (8.8 mL, 140 mmol) was added to a solution of the product of preparation 79 (16.0 g, 70 mmol) in acetic acid (33 mL). The resulting solution was cooled to 0° C., treated with concentrated sulphuric acid (33 mL), and the reaction mixture allowed to warm gradually to room temperature. After 4 hours, the reaction mixture was poured onto ice and basified with solid sodium carbonate. The solution was extracted with ethyl acetate (2×500 mL) and the combined organic extract solution was dried over magnesium sulphate and concentrated in vacuo to afford the title product as a colorless solid in 96% yield 19.0 g. $^1$HNMR (CDCl$_3$, 400 MHz) δ: 1.36(6H, s), 3.02(2H, s), 3.62(2H, s), 3.95(2H, s), 6.19(1H, m), 7.06–7.31(4H, m); LRMS ESI m/z 282 [M–H]$^−$ Preparation 81:
[3-(2-Amino-2-methyl-propyl)-phenyl]-acetic acid methyl ester

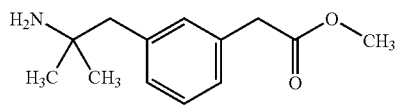

A solution of the product of preparation 80 (5.1 g, 18 mmol), thiourea (1.6 g, 21 mmol) and acetic acid (18 mL) in ethanol (80 mL) was heated under reflux 16 hours. The reaction mixture was then allowed to cool to room temperature and was filtered. The filtrate was concentrated in vacuo and the residue was dissolved in methanol (150 mL) and saturated with hydrogen chloride gas. The resulting solution was heated to reflux for 16 hours. The mixture was concentrated in vacuo and the residue partitioned between ethyl acetate (200 mL) and 5% aqueous sodium carbonate solution (200 mL). The organic phase was washed with brine (100 mL), dried over magnesium sulphate and concentrated in vacuo. The residue was purified by strong cation exchange resin, eluting with methanol followed by 2M solution of ammonia in methanol to afford the title compound as a yellow oil in 67% yield, 2.68 g. $^1$HNMR (CDCl$_3$, 400 MHz) δ: 1.14(6H, s), 2.68(2H, s), 3.62(2H, s), 3.69(3H, s), 7.08–7.16(3H, m), 7.23–7.27(1H, m); LRMS ESI m/z 222 [M+H]$^+$ Preparation 82: Methyl (3-{2-[(tert-butoxycarbonyl)amino]-2-methyl propyl}phenyl) acetate

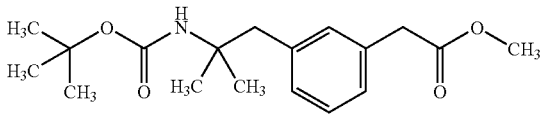

The title compound was prepared form the product of preparation 81, using a method similar to that of preparation 49, to afford the title compound as a colourless oil in 81% yield. $^1$HNMR (CDCl$_3$, 400 MHz) δ: 1.25 (6H, s), 1.45 (9H, s), 2.95 (2H, s), 3.60 (2H, s), 3.70 (3H, s), 4.25 (1H, bs), 7.02–7.06 (2H, m), 7.15 (1H, d), 7.25 (1H, m); LRMS ESI m/z 344 [M+Na]$^+$ Preparation 83: (3-{2-[(tert-Butoxycarbonyl)amino]-2-methylpropyl} phenyl)acetic acid

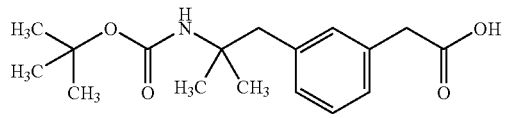

5M Sodium hydroxide solution (4.6 mL 23 mmol) was added to a solution of the product of preparation 82 (7.45 g, 23 mmol) in dioxan (30 mL) and water (8 mL) and the mixture was stirred at room temperature for 18 hours. The reaction mixture was then concentrated in vacuo and the residue was dissolved in water and acidified to pH3 with 2M hydrochloric acid. The mixture was then extracted with ethyl acetate (3×30 mL) and the combined organic solution was washed with brine (3×30 mL), dried over sodium sulfate and concentrated in vacuo to give an oil. This oil was then azeotroped with diethyl ether to afford the title compound as a colourless gum in 99% yield, 7.0 g. ¹HNMR (CDCl₃, 400 MHz) δ: 1.25 (6H, s), 1.50 (9H, s), 2.95 (2H, s), 3.55 (2H, s), 3.65 (s, 1H), 7.05 (2H, m), 7.10 (1H, d), 7.20 (1H, m), 7.25 (1H, m)

Preparation 84: Benzyl (3-{2-[(tert-Butoxycarbonyl) amino]-2-methylpropyl}phenyl)acetate

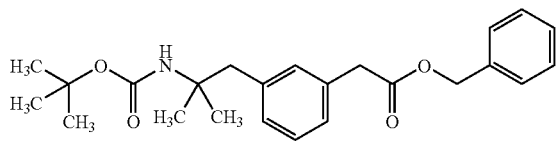

Caesium carbonate (6.03 g, 18.6 mmol) was added to a solution of the product of preparation 83 (5.7 g, 18.6 mmol) in N,N-dimethylformamide (40 mL) and the mixture was stirred for 1 hour at room temperature. The reaction mixture was then concentrated in vacuo and the residue was dissolved in N,N-dimethylformamide (80 mL), treated with benzylbromide (3.18 g, 18.6 mmol) and stirred for 3 hours at room temperature. The mixture was then filtered and concentrated in vacuo and the residue was dissolved in ethyl acetate (60 mL), washed with brine (60 mL), dried over magnesium sulfate and concentrated in vacuo to afford the title compound as a pale yellow oil in 76% yield, 5.6 g. ¹HNMR (CDCl₃, 400 MHz) δ: 1.25 (6H, s), 1.49 (9H, s), 2.98 (2H, s), 3.65 (2H, s), 4.30 (s, 1H), 5.14 (2H, s), 7.06–7.10 (2H, d), 7.15–7.20 (1H, m), 7.22–7.39 (6H, m); LRMS ESI m/z396 [M−H]⁻

Preparation 85: Benzyl [3-(2-amino-2-methylpropyl)phenyl]acetate

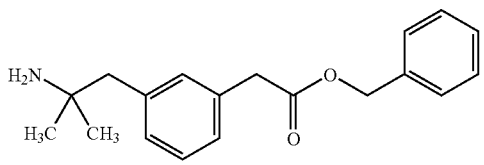

Trifluoroacetic acid (30 mL) was added to the product of preparation 84 (5.6 g, 14.1 mmol) and the mixture was stirred at room temperature for 18 hours. The reaction mixture was then concentrated in vacuo and the residue was diluted with dichloromethane (100 mL) and basified with saturated sodium hydrogen carbonate solution (300 mL). The organic layer was separated, washed with brine, dried over magnesium sulfate and concentrated in vacuo to afford the title compound as a yellow oil in 76% yield. ¹HNMR (CDCl₃, 400 MHz) δ: 1.10 (6H, s), 1.50 (9H, s), 2.64 (2H, s), 3.66 (2H, s), 5.13 (2H, s), 7.07–7.12 (2H, d), 7.14–7.18 (1H, m), 7.22–7.38 (6H, m); LRMS ESI m/z298 [M+H]⁺

Preparation 86: Benzyl (3-{2-[((2R)-2-[4-(benzyloxy)-3-(formylamino)phenyl]-2-{[tert-butyl(dimethyl)silyl]oxy}ethyl)amino]-2-methylpropyl}phenyl)acetate

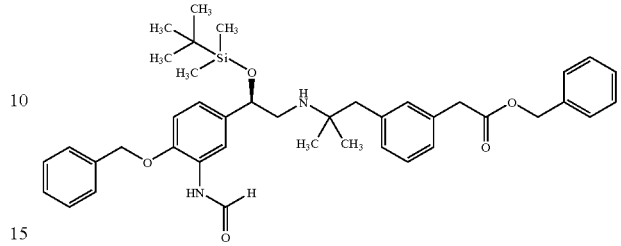

The title compound was prepared from the products of preparation 12 and preparation 85, using a similar method to that of preparation 13, in 55% yield. ¹H NMR (400 MHz, CDCl₃) δ: −0.20 (3H, m), −0.06 (3H, s), 0.78 (9H, s), 0.92 (3H, s), 0.95 (3H, s), 2.53–2.77 (4H, m), 3.57 (2H, s), 4.61–4.68 (1H, m), 5.01–5.02 (2H, m), 5.06 (2H, s), 6.84–6.87 (1H, m), 6.97–7.36 (14H, m), 7.62–7.70 (1H, m), 8.33–8.35 (1H, m), 8.34 (s), 8.67 (s), 8.70 (s); LRMS ESI m/z 681 [M+H]⁻

Preparation 87: {3-[2-({(2R)-2-{[tert-Butyl(dimethyl)silyl]oxy}-2-[3-(formylamino)-4-hydroxyphenyl]ethyl}amino)-2-methylpropyl]phenyl}acetic acid

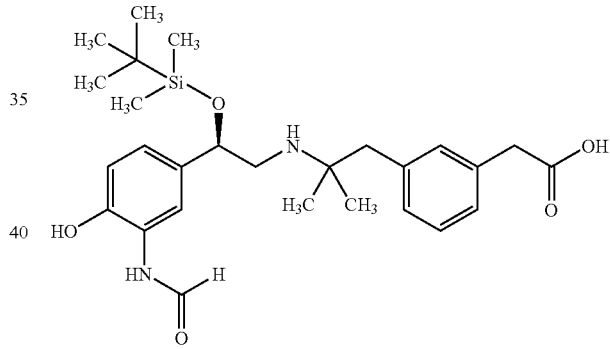

The title compound was prepared from the product of preparation 86, using a similar method to that of preparation 26, in 93% yield. ¹H NMR (400 MHz, CDCl₃) δ: −0.06 (3H, s), 0.05 (3H, s), 0.88 (9H, s), 1.00 (3H, s), 1.04 (3H, s), 2.58–2.88 (4H, m), 3.58 (2H, s), 4.64–4.67 (1H, m), 6.88–6.90 (1H, m), 6.95–6.98 (1H, m), 7.07–7.27 (5H, m), 8.04–8.05 (d), 8.25 (s), 9.55 (bs); LRMS ESI m/z 501 [M+H]⁻

Preparation 88: 2-Chloro-N-ethyl-5-hydroxybenzamide

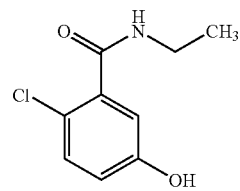

The title compound was prepared from 2-chloro-5-hydroxybenzoic acid and ethylamine, using a method similar to that used for preparation 52, as a colourless solid. ¹HNMR (400 MHz, CDCl₃) δ: 1.22 (3H, t), 3.42–3.49 (2H, m), 6.48–6.52 (1H, m), 6.80 (1H, dd), 7.13 (1H, d), 7.38 (1H, d); LRMS ESI m/z 200 [M+H]⁺

Preparation 89:
4-Chloro-3-[(ethylamino)methyl]phenol

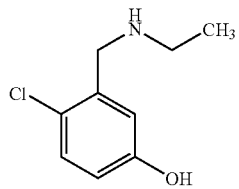

The title compound was prepared from the product of preparation 88 using the method of preparation 57, as a colourless solid. ¹HNMR (400 MHz, CD₃OD) δ: 1.15 (3H, t), 2.68 (2H, q), 3.79 (2H, s), 6.67–6.70 (1H, m), 6.84 (1H, d), 7.16 (1H, d).

Preparation 90: 4-{[tert-Butyl(dimethyl)silyl]oxy}-2-chlorobenzaldehyde

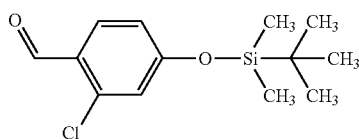

A solution of 2-chloro-4-hydroxybenzaldehyde (5.0 g, 32 mmol), tert-butyl(dimethyl)silyl chloride (5.3 g, 35 mmol), imidazole (2.9 g, 45 mmol) and N,N-dimethylaminopyridine (10 mg) in N,N-dimethylformamide (40 mL) was stirred at room temperature for 16 hours. The solvent was removed in vacuo and the residue was partitioned between ethyl acetate (100 mL) and water (100 mL). The organic phase was separated, washed with brine (50 mL), dried over sodium sulfate and concentrated in vacuo. Purification by column chromatography on silica gel, eluting with pentane: ethyl acetate, 75:25 to 67:33, afforded the title compound as a colourless oil in 75% yield, 6.50 g. ¹HNMR (400 MHz, CDCl₃) δ: 0.25 (6H, s), 0.97 (9H, s), 6.80 (1H, dd), 6.87 (1H, d), 7.84 (1H, d), 10.32 (1H, s)

Preparation 91: N-(4-{[tert-Butyl(dimethyl)silyl]oxy}-2-chlorobenzyl) prop-2-en-1-amine

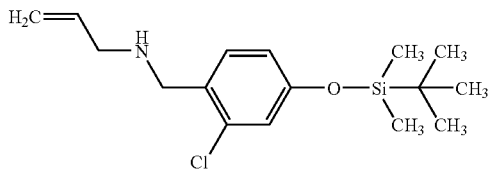

A solution of the aldehyde from preparation 90 (6.50 g, 24.0 mmol) and allylamine (1.51 g, 26.4 mmol) in dichloromethane (60 mL) was treated with sodium triacetoxyborohydride (7.6 g, 35.6 mmol) and the resulting suspension stirred at room temperature for 16 hours. Saturated sodium bicarbonate solution (50 mL) was added and the organic layer separated. The organic solution was washed with brine (50 mL), dried (sodium sulfate) and concentrated in vacuo to give a yellow oil. Purification of the oil by column chromatography on silica gel, eluting with pentane: ethyl acetate 75:25 to 67:33, afforded the title compound as a colourless oil in 38% yield, 2.80 g. ¹HNMR (400 MHz, CDCl₃) δ: 0.19 (6H, s), 0.97 (9H, s), 1.84 (1H, bs), 3.26 (2H, d), 3.81 (2H, s), 5.12 (1H, dd), 5.20 (1H, dd), 5.88–5.98 (1H, m), 6.71 (1H, dd), 6.85–6.86 (1H, d), 7.24 (1H, d); LRMS ESI m/z 312 [M+H]⁺

Preparation 92: (4-{[tert-Butyl(dimethyl)silyl]oxy}-2-chlorobenzyl)amine

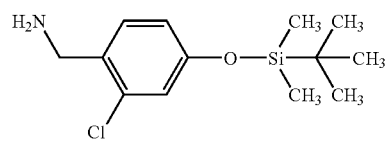

A solution of the product of preparation 91 (2.8 g, 9.0 mmol), dimethylbarbituric acid (7.0 g, 45 mmol) and tetrakis(triphenylphosphine)palladium(0) (0.10 g, 0.08 mmol) in dichloromethane (80 mL) was heated under reflux for 4 hours. The cooled solution was then concentrated in vacuo and the residue was partitioned between ethyl acetate (50 mL) and 1N aqueous sodium hydroxide solution (50 mL). The organic layer was separated, washed with brine (50 mL), dried over sodium sulfate and concentrated in vacuo. Purification of the residue by column chromatography on silica gel, eluting with dichloromethane:methanol:0.880 ammonia, 98:2:0 to 95:5:0.5, afforded the title compound as a colourless oil 70% yield, 1.70 g. ¹HNMR (400 MHz, CDCl₃) δ: 0.19 (6H, s), 0.97 (9H, s), 1.89 (2H, s), 3.85 (2H, s), 6.70 (1H, dd), 6.85–6.86 (1H, dd), 7.21 (1H, d)

Preparations 93 to 95:

The following compounds, of the general formula shown below were prepared from the product of preparation 87 and the appropriate amine, using a method similar to that described for preparation 27. The reactions were monitored by tlc analysis and were stirred at room temperature for 18–72 hours.

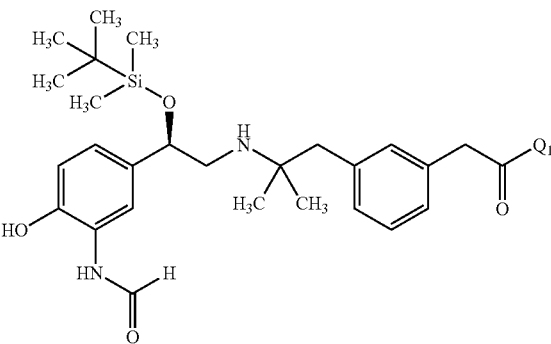

| No. | Q₁ | Data | Yield |
|---|---|---|---|
| 93 | (4-methoxycarbonylbenzyl)amino group | $^1$H NMR(400MHz, CD$_3$OD) δ: −0.18(3H, s), −0.07(3H, s), 0.75(9H, s), 1.01(3H, s), 1.04(3H, s), 2.59–2.83(4H, m), 3.56–3.58(2H, m), 3.89 (3H, s), 4.41–4.53(2H, m), 4.63–4.66(1H, m), 6.80–6.82(1H, m), 6.95–6.98(1H, m), 7.03–7.05 (1H, m), 7.09–7.11(2H, m), 7.21–7.26(4H, m), 7.93–7.69(2H, d); LRMS ESI m/z 648 [M + H]$^+$ | 41% |
| 94 | (2-chloro-5-hydroxybenzyl)(ethyl)amino group | $^1$H NMR(400MHz, CD$_3$OD) δ: −0.21 to −0.16 (3H, m), −0.04–0.01(3H, m), 0.76–0.83(9H, m), 1.02–1.09(9H, m), 2.61–2.77(3H, m), 2.84–2.92 (1H, m), 3.32–3.38(2H, m), 3.70, 3.81(2H, 2xs), 4.55, 4.63(2H, 2xs), 4.66, 4.72(1H, m), 6.62–6.69(1H, m), 6.78–6.87(2H, m), 6.90–6.96(1H, m), 6.99–7.26(5H, m), 8.07–8.10(1H, s), 8.29 (s), 8.60(s); LRMS APCI m/z 668 [M + H]$^+$ | 43% |
| 95 | (4'-hydroxybiphenyl-4-ylmethyl)amino group | $^1$H NMR(400MHz, CD$_3$OD) δ: −0.25(3H, s), −0.09(3H, s), 0.73(9H, m), 0.97(3H, s), 0.99 (3H, s), 2.56–2.83(4H, m), 3.47–3.48(2H, m), 4.31(2H, s), 4.59–4.63(1H, m), 6.73–7.41(15H, m), 8.08(s), 8.21(s), 8.57(s); LRMS ESI m/z 682 [M + H]$^+$ | 54% |

Preparation 96: 2-{3-[2-({(2R)-2-{[tert-Butyl(dimethyl)silyl]oxy}-2-[3-(formylamino)-4-hydroxyphenyl]ethyl}amino)-2-methylpropyl]phenyl}-N-(2-chloro-4-hydroxybenzyl)acetamide

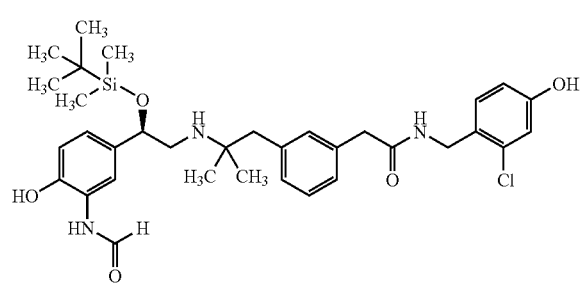

The title compound was prepared from the products of preparations 87 and 92 using a method similar to that of preparation 27, as brown foam in 62% yield. $^1$H NMR (400 MHz, CD$_3$OD) δ: −0.19 (3H, s), −0.03 (3H, s), 0.79 (9H, s), 1.01–1.10 (6H, m), 2.62–2.76 (3H, m), 2.85 (1H, m), 3.37–3.92 (2H, m), 4.34 (2H, s), 4.66 (1H, m), 6.62 (1H, m), 6.78–6.82 (2H, m), 6.91 (1H, m), 7.02–7.23 (5H, m), 8.09–8.11 (1H, m), 8.27 (s), 8.59 (s); LRMS APCI m/z 640 [M+H]$^+$ Preparation 97:
2-(3-Bromophenyl)-N-(3,4-dimethylbenzyl)acetamide

[Structure of 2-(3-Bromophenyl)-N-(3,4-dimethylbenzyl)acetamide]

The title compound was prepared from 3,4-dimethylbenzylamine and 3-bromophenylacetic acid, using a method similar to that of preparation 27, as a white solid in 93% yield. $^1$H NMR (400 MHz, CDCl$_3$) δ: 2.20 (6H, s), 3.50 (2H, s), 4.30 (2H, d), 5.80 (1H, brs), 7.60–7.80 (7H, m); LRMS ESI 332 [M]$^+$ Preparation 98: N-(3,4-Dimethylbenzyl)-2-{3-[(E)-2-(1,3-dioxo-1,3-dihydro-2H-isoindol-2-yl)vinyl]phenyl}acetamide

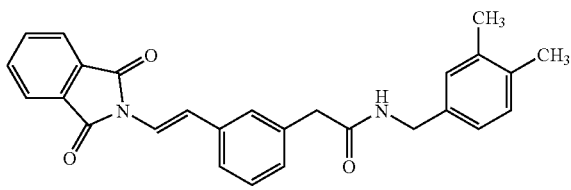

The product of preparation 97 (5.0 g, 15 mmol), N-vinylphthalimide (2.62 g, 15.1 mmol), tri-ortho-tolylphosphine (473 mg, 1.55 mmol), palladium(II)acetate (98 mg, 0.4 mmol) and N,N-diisopropylethylamine (30 mL, 172 mmol) in acetonitrile (35 mL) was heated under reflux for 16 hours. The reaction mixture was then cooled to room temperature and the precipitate was filtered off. The solid was then dissolved in dichloromethane, activated charcoal was added, and the solution was filtered through Celite®. The filtrate was concentrated in vacuo and the residue was re-crystallised from hot dichloromethane/methanol to afford the title compound as a yellow solid in 55% yield, 3.5 g. $^1$H NMR (400 MHz, CDCl$_3$) δ: 2.20 (6H, s), 3.80 (2H, s), 4.30 (2H, d), 6.0 (1 H, brs), 6.90 (2H, m), 7.01 (1H, m), 7.18 (1H, m), 7.26–7.40 (4H, m), 7.56–7.61 (1H, m), 7.75 (2H, m), 7.88 (2H, m)

Preparation 99: N-(3,4-Dimethylbenzyl)-2-{3-[2-(1,3-dioxo-1,3-dihydro-2H-isoindol-2-yl)ethyl]phenyl}acetamide

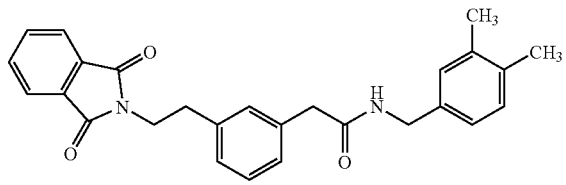

The product of preparation 98 (3.3 g, 7.7 mmol) and 10% palladium-on-carbon (1 g) were suspended in ethanol and the mixture was stirred under 50 psi of hydrogen gas, at room temperature for 16 hours. The reaction mixture was then filtered through Arbocel®, washing through with ethanol, and the filtrate was concentrated in vacuo to afford the title product as a yellow solid in 52% yield, 1.7 g. $^1$H NMR (400 MHz, CDCl$_3$) δ: 2.20 (6H, s), 2.95 (2H, t), 3.60 (2H, s), 3.90 (2H, t), 4.39 (2H, d), 5.95 (1H, brs), 6.90–7.20 (8H, m), 7.60–7.70 (3H, m)

Preparation 100: 2-[3-(2-Aminoethyl)phenyl]-N-(3,4-dimethylbenzyl)-acetamide

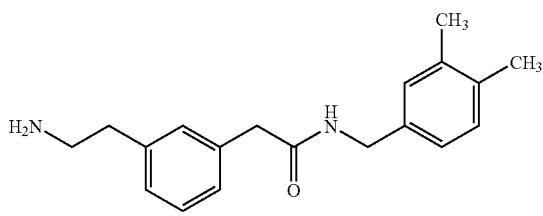

Hydrazine monohydrate (6 mL, 123.6 mmol) was added to a suspension of the product of preparation 99 (3.5 g, 8.2 mmol) in ethanol (125 mL) and the mixture was heated under reflux for 4 hours. The reaction mixture was then cooled to room temperature and filtered. The filtrate was concentrated in vacuo and the residue was purified by column chromatography on silica gel, eluting with dichloromethane: methanol: 0.88 ammonia, 95:5:1 to afford the title compound the title compound in 57% yield, 1.4 g. $^1$H NMR (400 MHz, CD$_3$OD) δ: 2.18 (6H, s), 2.73 (2H, m), 2.86 (2H, m), 3.50 (2H, s), 4.25 (2H, s), 6.87–7.25 (7H, m); LRMS ESI 297 [M+H]$^+$ Preparation 101: 2-(3-{2-[((2R)-2-[4-(Benzyloxy)-3-(formylamino)phenyl]-2[tert-butyl(dimethyl)silyl]oxy}ethyl)amino]ethylphenyl)-N-(3,4-dimethylbenzyl)acetamide

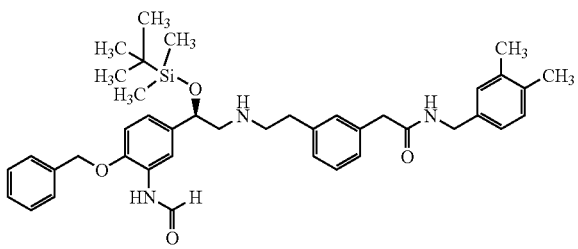

The title compound was prepared from products of preparation 12 and preparation 100, using a method similar to that of preparation 33, as a yellow oil in 37% yield. $^1$H NMR (400 MHz, CD$_3$OD) δ: −0.18 (3H, s), −0.03 (3H, s), 0.80 (9H, s), 2.20 (6H, m), 2.80 (4H, m), 3.40 (2H, m), 3.50 (2H, s), 4.25 (2H, s), 4.76 (1H, m), 5.18 (2H, s), 6.85–7.45 (15H, m), 8.23 (s), 8.30 (s); LRMS ESI 680 [M+H]$^+$ Preparation 102: 2-{3-[2-({(2R)-2-{[tert-butyl(dimethyl)silyl]oxy}-2-[3-(formylamino)-4-hydroxyphenyl]ethyl}amino)ethyl]phenyl}-N-(3,4-dimethylbenzyl)acetamide

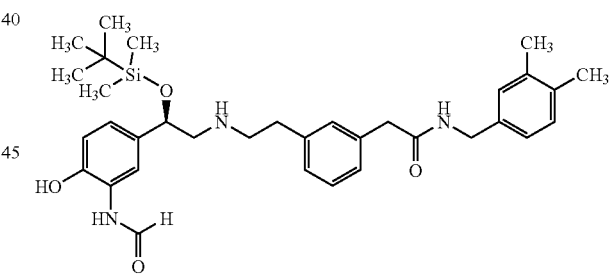

The title compound was prepared from the product of preparation 101, using a method similar to that of preparation 20, as a white foam in 83% yield. $^1$H NMR (400 MHz, CD$_3$OD) δ: −0.18 (3H, s), −0.05 (3H, s), 0.81 (9H, s), 2.18 (6H, m), 2.80 (4H, m), 3.29 (2H, m), 3.51 (2H, s), 4.25 (2H, s), 4.70 (1H, m), 6.80 (1H, d), 6.91–7.20 (9H, m), 8.03 (s), 8.25 (s); LRMS ESI 590 [M+H]$^+$ Preparations 103 to 110

The following compounds, of the general formula shown below were prepared from the product of preparation 87 and the appropriate amine, using a method similar to that described for preparation 27. The reactions were monitored by tlc analysis and were stirred at room temperature for 18–72 hours.

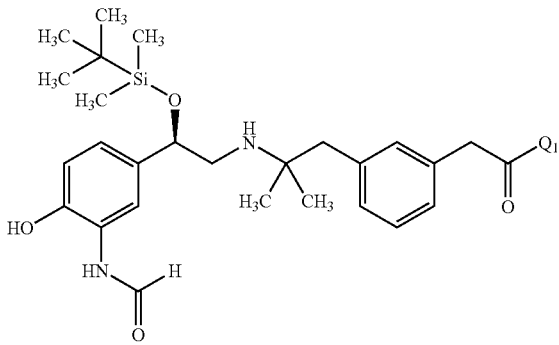

| No. | Q₁ | Data | Yield |
|-----|-----|------|-------|
| 103 | (4-methylthio-benzyl)HN- | ¹H NMR(400MHz, CD₃OD) δ: −0.25(3H, s), −0.08(3H, s), 0.73(9H, s), 0.97(3H, s), 0.99 (3H, s), 2.37(3H, s), 2.56–2.83(4H, m), 3.39–3.45(2H, m), 4.24(2H, s), 4.60–4.63(1H, m), 6.73–6.79(1H, m), 6.85(1H, dd), 6.97(1H, d), 7.03(1H, s), 6.97–7.16(6H, m), 8.04(d), 8.21 (s), 8.53(s); LRMS ESI m/z 658 [M + H]⁻ | 66% |
| 104 | (4-trifluoromethyl-benzyl)HN- | ¹H NMR(400MHz, CDCl₃) δ: −0.24(3H, s), −0.08(3H, s), 0.74(9H, s), 0.98(3H, s), 1.00 (3H, s), 2.57–2.83(4H, m), 3.48(2H, m), 4.37 (2H, s), 4.60–4.63(1H, m), 6.73(1H, d), 6.85 (1H, dd), 6.99–7.17(5H, m), 7.32(2H, d), 7.49 (2H, d), 8.04(d), 8.22(s), 8.52(s); LRMS APCI m/z 658 [M + H]⁺ | 55% |
| 105 | (4-cyano-benzyl)HN- | ¹H NMR(400MHz, CDCl₃) δ: −0.17(3H, s), −0.06(3H, s), 0.76(9H, s), 1.01(3H, s), 1.03 (3H, s), 2.59–2.83(4H, m), 3.56–3.68(2H, dd), 4.45–4.49(2H, m), 4.64–4.67(1H, m), 6.84–6.86(1H, m), 6.95(8H, m), 7.55–7.57(2H, m), 8.17(d), 8.63(s); LRMS ESI mfz 615 [M + H]⁺ | 19% |
| 106 | (4-trifluoromethoxy-benzyl)HN- | ¹H NMR(400MHz, CDCl₃) δ: −0.16(3H, s), −0.06(3H, s), 0.77(9H, s), 1.00(3H, s), 1.04 (3H, s), 2.57–2.85(4H, m), 2.53–3.67(2H, dd), 4.40(2H, m), 4.64–4.67(1H, m), 6.80(1H, m), 6.96(1H, m), 7.02(7H, m), 7.32–7.34(2H, m), 8.17(d), 8.74(s); LRMS APOI m/z 674 [M + H]⁺ | 52% |
| 107 | (4'-hydroxy-biphenyl-3-ylmethyl)HN- | ¹H NMR(400MHz, CD₃OD) δ: −0.26(3H, s), −0.10(3H, s), 0.72(9H, s), 0.93(3H, s), 0.95 (3H, s), 2.49–2.79(4H, m), 3.46–3.47(2H, m), 4.33(2H, s), 4.58–4.61(1H, m), 6.72–7.48 (15H, m), 8.04(1H, d), 8.21(s), 8.52(s) LRMS APCI m/z 682 [M + H]⁺ | 72% |
| 108 | (5-chloro-2-hydroxy-benzyl)HN- | ¹H NMR(400MHz, CD₃OD) δ: −.024(3H, s), 0.08(3H, s), 0.74(9H, s), 0.99(3H, s), 1.02 (3H, s), 2.59–2.87(4H, m), 3.47(2H, m), 4.23 (2H, s), 4.62–4.65(1H, m), 6.65(1H, d), 6.74 (1H, d), 6.90–6.95(1H, m), 7.01–7.07(3H, m), 7.10(1H, s), 7.14–7.24(2H, m), 8.05(1H, d), 8.22(s), 8.53(s); LRMS APCI m/z 640 [M + H]⁺ | 43% |
| 109 | (tetrahydrothiopyran-4-yl)HN- | ¹H NMR(400MHz, CD₃OD) δ: −0.24(3H, s), −0.08(3H, s), 0.73(9H, s), 1.00(3H, s), 1.02 (3H, s), 1.45–1.56(2H, m), 2.01–2.04(2H, m), 2.53–2.84(8H, m), 3.38(2H, s), 3.58(1H, s), 4.60–4.63(1H, m), 6.73(1H, d), 6.85(1H, dd), 6.97(1H, d), 7.05–7.14(3H, m), 8.04(1H, d), 8.24(s), 8.53(s); LRMS APCI m/z 598 [M + H]⁺ | 83% |

-continued

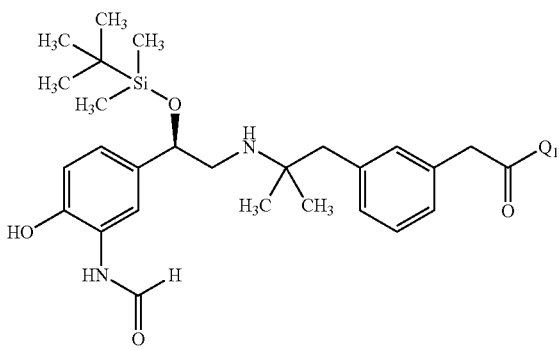

| No. | Q₁ | Data | Yield |
|---|---|---|---|
| 110 | ![sulfonyl benzyl amine] | $^1$H NMR(400MHz, CD$_3$OD) δ: −0.18(3H, s), −0.02(3H, s), 0.80(9H, s), 1.05(3H, s), 1.07 (3H, s), 2.61–2.91(4H, m), 3.08(3H, s), 3.55 (2H, d), 4.45(2H, s), 4.66(2H, dd), 6.79(1H, d), 6.91(1H, dd), 7.05(1H, d), 7.13(1H, s), 7.15–7.25(3H, m), 7.45(2H, d), 7.85(2H, d), 8.10(1H, d), 8.28(s), 8.60(s); LRMS APCI m/z 668 [M + H]⁺ | |

Preparations 111 to 119

1-(3-Dimethylaminopropyl)-3-ethylcarbodiimide hydrochloride (40 mg, 205 μmol) was added to a solution of preparation 42 (100 mg, 206 μmol), hydroxybenzotriazole hydrate (32 mg, 205 μmol) and triethylamine (0.55 μL, 412 μmol) in dichloromethane (2 mL) followed by the amine (205 μmol) and the mixture was stirred at room temperature for 18 hours. The solvent was then removed in vacuo and the residue was diluted with ethyl acetate, washed with sodium hydrogencarbonate solution (20 mL) and brine (20 mL), dried (Na$_2$SO$_4$) and concentrated in vacuo to leave a film which was suspended in diethylether (×3) to afford a foam.

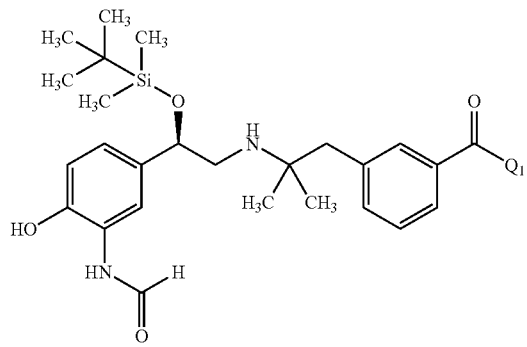

| No. | Q₁ | Data | Yield |
|---|---|---|---|
| 111 | ![phenethylamine] | LRMS ESI m/z 590 [M + H]⁺ | 81% |
| 112 | ![cyclohexylmethylamine] | LRMS APCl m/z 582 [M + H]⁺ | 74% |

-continued

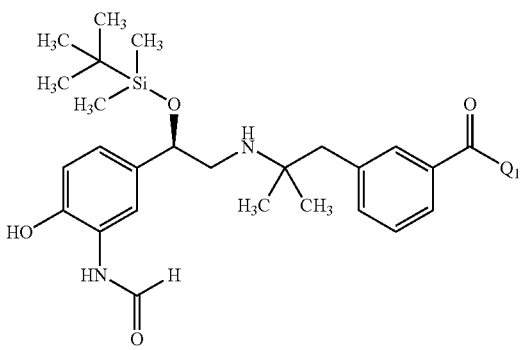

| No. | Q₁ | Data | Yield |
|---|---|---|---|
| 113 | (piperidin-1-yl) | LRMS APCl m/z 554 [M + H]⁺ | 94% |
| 114 | HN-CH₂CH₂-(3-CF₃-C₆H₄) | LRMS APCl m/z 658 [M + H]⁺ | 87% |
| 115 | HN-CH₂CH₂CH₂-Ph | LRMS APCl m/z 604 [M + H]⁺ | 83% |
| 116 | HN-(indan-2-yl) | LRMS APCl m/z 602 [M + H]⁺ | 89% |
| 117 | HN-CH₂CH₂-(pyridin-2-yl) | LRMS APCl m/z 591 [M + H]⁺ | 74% |
| 118 | HN-CH₂CH₂-(4-OMe-C₆H₄) | LRMS APCl m/z 620 [M + H]⁺ | 90% |
| 119 | HN-CH₂CH₂-(4-SO₂NH₂-C₆H₄) | LRMS APCl m/z 669 [M + H]⁺ | 80% |
| 120* | (1,2,3,4-tetrahydroisoquinolin-2-yl) | LRMS APCl m/z 602 [M + H]⁺ | 92% |
| 121* | HN-(adamantan-1-yl) | LRMS APCl m/z 620 [M + H]⁺ | 38% |

*no evaporation from diethylether

Preparation 122: N-{5-[(2R)-2-{2-[3-(10-Aza-tricyclo[6.3.1.0*2,7*]dodeca-2(7),3,5-triene-10-carbonyl)phenyl]-1,1-dimethylethylamino}-1-(tert-butyldimethylsilanyloxy)ethyl]-2-hydroxyphenyl}formamide

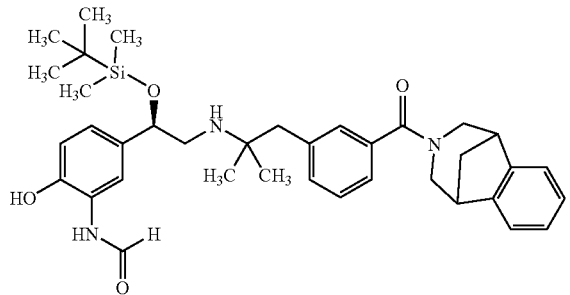

The title compound was prepared with 10-aza-tricyclo[6.3.1.0*2,7*]dodeca-2(7),3,5-triene, using a method similar to that of preparation 69. LRMS APCI m/z 628 [M+H]$^+$ Preparation 123: 3-{2-[(2R)-2-(tert-Butyldimethylsilanyloxy)-2-(3-formylamino-4-hydroxyphenyl)ethylamino]-2-methylpropyl}-N-[2-(5-chloro-2-hydroxyphenyl)ethyl]benzamide

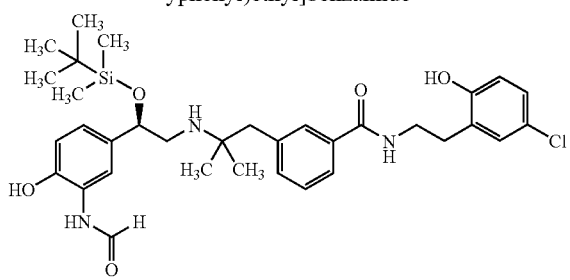

The title compound was prepared with 2-(2-aminoethyl)-4-chlorophenol, using a method similar to that of preparation 69. LRMS APCI m/z 640 [M+H]$^+$ Preparations 124 to 128

The amine (412 μmol) was added to a mixture of preparation 42 (200 mg, 412 μmol), hydroxybenzotriazole hydrate (63 mg, 412 lmol), 1-(3-dimethylaminopropyl)-3-ethylcarbodiimide hydrochloride (79 mg, 412 μmol) and triethylamine (0.11 mL, 824 μmol) in dichloromethane (2 mL) and the mixture was stirred at room temperature for 18 hours. The solvent was then removed in vacuo and the residue was diluted with ethyl acetate, washed with sodium hydrogencarbonate solution (3×20 mL) and brine (3×20 mL), dried (MgSO$_4$). The crude material was purified by chromatography on silica gel, eluting with dichloromethane: 0.88 ammonia, 99.7:0.3. The appropriate fractions were evaporated under reduced pressure and the residue and concentrated in vacuo, the resulting white foam was suspended in diethylether (×3) and evaporated.

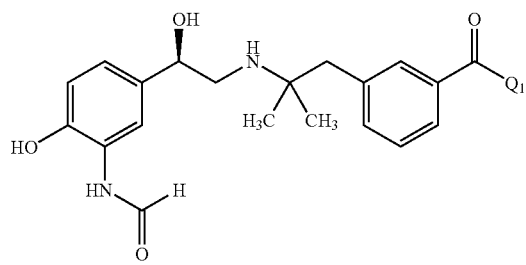

| No. | Q$_1$ | Data | Yield |
|---|---|---|---|
| 124 | ![structure with CH3, CH3, HN-CH2CH2-phenyl] | $^1$H NMR(400MHz, CDCl$_3$) δ: −0.23(3H, s), −0.09(3H, s), 0.69(9H, s), 1.07(3H, s), 1.08 (3H, s), 2.27(3H, s), 2.29(3H, s), 2.60–2.82 (4H, m), 2.98(2H, t), 3.64–3.73(2H, m), 4.61– 4.65(1H, m), 6.39(1H, m), 6.84–7.42(10H, m), 7.80(1H, s), 8.24(1H, s), 9.70–9.80(m); LRMS APCl m/z 619 [M + H]$^+$ | 63% |
| 125 | ![structure with Cl, HN-CH2CH2-phenyl] | $^1$H NMR(400MHz, CDCl$_3$) δ: −0.23(3H, s), −0.09(3H, s), 0.70(9H, s), 1.02(3H, s), 1.04 (3H, s), 2.60–2.79(4H, m), 3.09–3.12(2H, t), 3.74–3.79(2H, m), 4.58–4.60(1H, m), 6.35– 6.39(1H, m), 6.88(1H, d), 6.94(1H, d), 7.10 (1H, s), 7.20–7.34(4H, m), 7.38–7.42(2H, m), 7.76(1H, s), 8.24(1H, s), 9.76(1H, s); LRMS APCl m/z 624 [M + H]$^+$ | 70% |

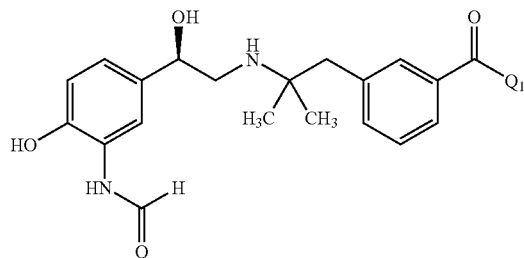

| No. | Q₁ | Data | Yield |
|---|---|---|---|
| 126 | (2,6-dimethylphenyl)ethylamino | ¹H NMR(400MHz, CDCl₃) δ: −0.22(3H, s), −0.09(3H, s), 0.71(9H, s), 1.20(3H, s), 1.22 (3H, s), 2.34(6H, s), 2.61–2.78(4H, m), 3.00 (2H, t), 3.56–3.60(2H, m), 4.59–4.62(1H, m), 6.39–6.43(1H, m), 6.86(1H, d), 6.96–7.07 (3H, m), 7.16(1H, s), 7.28–7.33(2H, m), 7.42 (1H, d), 7.77(1H, s), 8.24(1H, s), 9.65(1H, s); LRMS APCl m/z 618 [M + H]⁺ | 96% |
| 127 | (4-methylphenyl)ethylamino | ¹H NMR(400MHz, CDCl₃) δ: −0.23(3H, s), −0.09(3H, s), 0.70(9H, s), 1.04(3H, s), 1.05 (3H, s), 2.33(3H, s), 2.61–2.76(4H, m), 2.88–2.92(2H, 1), 3.67–3.74(2H, m), 4.57–4.60(1H, m), 6.25–6.29(1H, m), 6.88(1H, d), 6.98(1H, d), 7.09–7.33(7H, m), 7.75(1H, s), 8.23(1H, s), 9.82(1H, s); LRMS APCl m/z 604 [M + H]⁺ | 73% |
| 128 | (naphthalen-1-yl)ethylamino | ¹H NMR(400MHz, CDCl₃) δ: −0.23(3H, s), −0.10(3H, s), 0.68(9H, s), 1.03(3H, s), 1.04 (3H, s), 2.59–2.76(4H, m), 3.42–3.48(2H, m), 3.80–3.94(2H, m), 4.58–4.61(1H, m), 6.30–6.34(1H, m), 6.89(1H, d), 6.98(1H, d), 7.10 (1H, s), 7.23–7.60(6H, m), 7.75(1H, s), 7.77 (1H, d), 8.15(1H, d), 8.18(1H, d), 9.77(1H, s); LRMS APCl m/z 640 [M + H]⁺ | 19% |

Preparation 129: 3-(2-Oxo-propyl)benzoic acid methyl ester

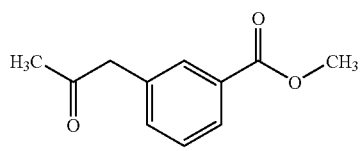

Tributyltin methoxide (80.3 mL, 279 mmol), methyl 3-bromobenzoate (53.5 g, 249 mmol), isopropenyl acetate (39.4 ml, 358 mmol), palladium(II)acetate (2.6 g, 11.6 mmol) and tri-ortho-tolylphosphine (7.1 g, 23.2 mmol) were stirred together in toluene (350 mL) at 100° C. under nitrogen for 18 hours. After cooling, the reaction was treated with potassium fluoride solution (4M, 560 ml) and stirred for 2 hours. The resulting mixture was diluted with further toluene (200 mL) and filtered through Celite®, washing the filter pad with ethyl acetate. The organic phase was separated, dried (sodium sulfate) and reduced in vacuo. The residue was purified by chromatography eluting with ethylacetate: pentane 10:90 to 20:80 to give the title compound (45.3 g) as an orange oil. ¹H NMR (400 MHz, CDCl₃) δ: 2.18 (3H, s), 3.75 (2H, s), 3.91 (3H, s), 7.43–7.37 (2H, m), 7.87 (1H, s), 7.95–7.93 (1H, d); LRMS ESI m/z 215 [M+Na]⁺, 191 [M−H]⁻.

Preparation 130: 3-[(2R)-2-((1R)-1-Phenylethylamino)propyl]benzoic acid methyl ester hydrochloride

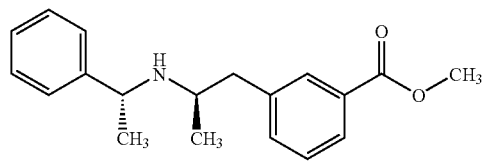

The title compound was prepared with preparation 129, using a method similar to that of preparation 19, to give the title compound (27.3 g) as a colourless crystalline solid. ¹H NMR (400 MHz, CD₃OD) δ: 1.17–1.16, (3H, d), 1.71–1.69 (3H, d), 2.71–2.65 (1H, dd), 3.25–3.19 (1H, m), 3.43–3.38 (1H, dd), 3.90 (3H, s), 4.68–4.63 (1H, q), 7.35–7.33 (1H, d), 7.45–7.42 (1H, dd), 7.55–7.49 (5H, m), 7.75 (1H, s), 7.92–7.90 (1H, d).

Preparation 131: Methyl {3-[(2R)-2-aminopropyl]phenyl}acetate

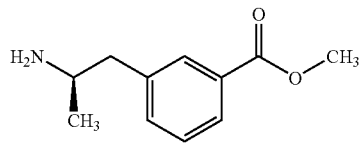

The title compound was prepared with preparation 130, using a method similar to that of preparation 20, to give the title compound (8.48 g) as a pale yellow oil. ¹H NMR (400 MHz, CDCl₃) δ: 1.14–1.12 (3H, d), 2.64–2.59 (1H, dd), 2.78–2.73 (1H, dd), 3.26–3.17 (1H, m), 3.90 (3H, s), 7.38–7.34 (2H, m), 7.90–7.87 (2H, m); LRMS ESI m/z 194 [M+H]⁺.

Preparation 132:
3-((2R)-2-tert-Butoxycarbonylaminopropyl)benzoic acid methyl ester

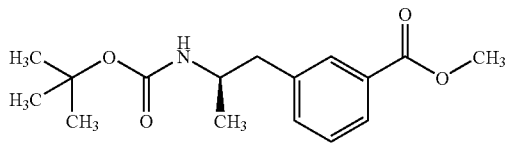

A mixture of preparation 131 (5.00 g, 26.0 mmol), di-tert-butyldicarboxylate (6.22 g, 28.5 mmol) and sodium hydrogencarbonate (4.35 g, 52 mmol) were stirred in a mixture of 1,4-dioxane (100 mL) and water (10 mL) for 20 h. The solvent was removed and the material partitioned between ethyl acetate (200 mL) and hydrochloric acid (2M, 100 mL), the organics were washed with brine (100 mL) and dried (MgSO₄). Removal of the solvent left a white solid (7.12 g, 93%). ¹H NMR (400 MHz, CD₃OD) δ: 1.09 (3H, d), 1.35 (9H, s), 2.73–2.79 (2H, m), 3.76–3.83 (1H, m), 3.89 (3H, s), 6.54 (1H, d), 7.26–7.46 (2H, m), 7.84–7.87 (2H, m); LCMS Rt 4.53 min m/z 294 [M+H]⁺

Preparation 133:
3-((2R)-2-tert-Butoxycarbonylaminopropyl)benzoic acid

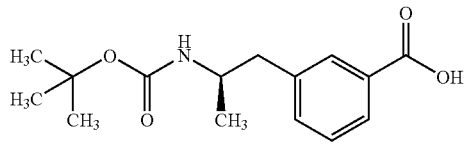

A mixture of preparation 132 (7.10 g, 24.3 mmol) and lithium hydroxide (1.00 M, 50.0 mL, 50.0 mmol) in tetrahydrofuran (100 mL) were stirred for 20 h. The reaction mixture was diluted with ethyl acetate (250 mL) and acidified to pH 2 with hydrochloric acid (2M). The aqueous phase was re-extracted with ethyl acetate (150 mL) and the combined organics washed with brine (300 mL) and dried (MgSO₄). Filtration and removal of the solvent gave 5.53 g (82%) of the title compound. ¹H NMR (400 MHz, CD₃OD) δ: 1.10 (3H, d), 1.36 (9H, s), 2.82–2.81 (2H, m), 3.77–3.84 (1H, m), 7.35–7.45 (2H, m), 7.84–7.89 (2H, m); LRMS APCI m/z 278 [M–H]⁻

Preparation 134:
3-((2R)-2-tert-Butoxycarbonylaminopropyl)benzoic acid benzyl ester

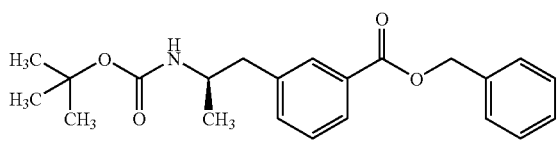

Caesium carbonate (6.50 g, 19.8 mmol) in water (10 mL) was added to a solution of preparation 133 (5.50 g, 19.8 mmol) in N,N-dimethylformamide (50 mL) and the resulting mixture stirred at room temperature for 1 h. Benzylbromide (3.42 g, 19.8 mmol) was then added and the mixture stirred for 20 h. Ethyl acetate (50 mL) was added and the suspension filtered, the filtrate was washed with saturated brine (100 mL) and dried (MgSO₄). Filtration and removal of the solvent left 7.20 g of the title compound. ¹H NMR (400 MHz, CD₃OD) δ: 1.09 (3H, d), 1.32 (9H, s), 2.74 (2H, d), 2.75–2.83 (1H, m), 5.34 (2H, s), 7.29–7.40 (4H, m), 7.43–7.47 (3H, m), 7.85–7.90 (2H, m); LRMS APCI m/z 270 [M-BOC]⁺

Preparation 135: 3-((2R)-2-Aminopropyl)benzoic acid benzyl ester

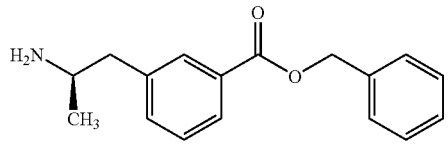

Preparation 134 (7.20 g, 19.0 mmol) was treated with trifluoroacetic acid (35 mL) and the mixture left to stir for 20 h. The trifluoroacetic acid was removed in vacuo and dichloromethane (175 mL) added. The mixture was basified with sat. sodium hydrogencarbonate (150 mL) and washed with sodium hydroxide (1M, 50 mL). The combined organics were washed with brine (150 mL) and dried (MgSO₄) to leave a brown oil (3.70 g, 72%). ¹H NMR (400 MHz, CD₃OD) δ: 1.04 (3H, d), 2.66 (2H, d), 3.05 (1H, dt), 5.33 (2H, s), 7.28–7.44 (7H, m), 7.86–7.90 (2H, m); LRMS APCI m/z 270 [M+H]⁺

Preparation 136: 3-{(2R)-2-[(2R)-2-(4-Benzyloxy-3-formylaminophenyl)-2-(tert-butyidimethylsilanyloxy)ethylamino]propyl}benzoic acid benzyl ester

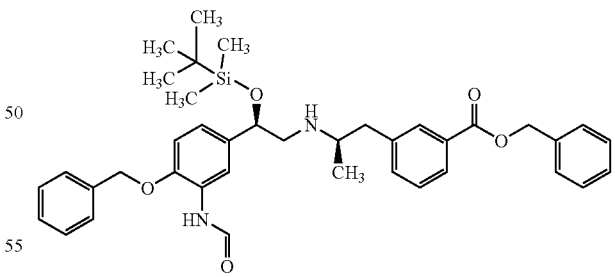

Preparation 135 (3.70 g, 13.8 mmol) and preparation 12 (3.20 g, 6.9 mmol) were heated to 90° C. for 26 h. The mixture was allowed to cool and diluted with dichloromethane (100 mL). The organics were washed with sat. sodium hydrogencarbonate (200 mL) and concentrated in vacuo. The crude material was purified by chromatography (×2), eluting with ethyl acetate: heptane 0:100 to 40:60 to yield 2.0 g (52%) of the title compound. LRMS APCI m/z 270 [M+H]⁺

Preparation 137: 3-{(2R)-2-[(2R)-2-(tert-Butyidimethylsilanyloxy)-2-(3-formylamino-4-hydroxyphenyl)ethylamino]propyl}benzoic acid

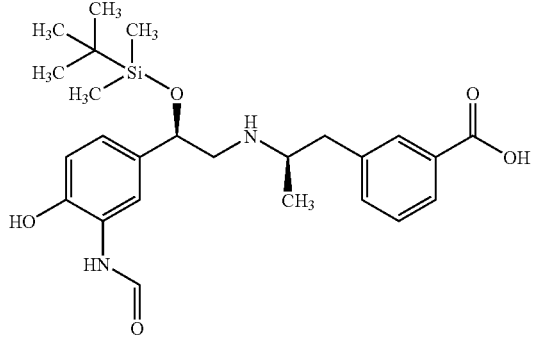

Preparation 136 (2.0 g, 3.1 mmol) and palladium-on-carbon (10%, 205 mg) in methanol (100 mL) were hydrogenated at 60 psi/RT for 20 h. A solution of ammonia in methanol (2M, 50 mL) was added and the mixture allowed to stir for 2 min. The mixture was then filtered through a filter-aid, which was washed with the ammonia in methanol solution (2M, 250 mL), and the resulting organics concentrated to yield a dark green solid. The crude material was purified by chromatography, eluting with dichloromethane: methanol: 0.88 ammonia 100:0:0 to 75:20:5 to yield the title compound as a dark green solid (131 mg). $^1$H NMR (400 MHz, DMSO-d$_6$) δ: −0.18 (3H, s), −0.06 (3H, s), 0.77 (9H, s), 0.89 (3H, d), 2.61–2.68 (2H, m), 2.65–2.73 (2H, m), 2.80–2.86 (1H, m), 4.56–4.60 (1H, m), 6.75 (1H, d), 6.81 (1H, dd), 7.83 (2H, d), 7.70–7.75 (2H, m), 8.00 (d), 8.25 (s), 9.53 (s); LRMS APCI m/z 473 [M+H]$^+$.

Preparation 138: 3-{(2R)-2-[(2R)-2-(tert-Butyidimethylsilanyloxy)-2-(3-formylamino-4-hydroxyphenyl)ethylamino]propyl}-N-[2-(4-hydroxyphenyl)-2-methylpropyl]benzamide

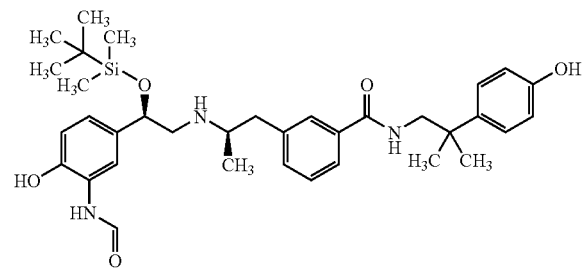

The title compound was prepared with 4-(2-amino-1,1-dimethylethyl)phenol hydrochloride (*Acta Chem. Scand.* 8, 1203, 1207; 1954), using a method similar to that of preparation 27. $^1$H NMR (400 MHz, CD$_3$OD) δ: −0.24 (3H, s), −0.08 (3H, s), 0.76 (9H, s), 0.99 (3H, d), 1.28 (6H, s), 2.54–2.92 (5H, m), 3.46 (2H, s), 4.60–4.63 (1H, m), 6.66–6.70 (3H, m), 6.77–6.80 (1H, dd), 7.20–7.34 (4H, m), 7.45 (1H, s), 7.50 (1H, d), 7.92–7.93 (1H, d), 8.21 (s), 8.55 (s); LRMS APCI m/z 620 [M+H]$^+$

Preparation 139: Methyl (2E)-3-[3-(2-oxopropyl)phenyl]acrylate

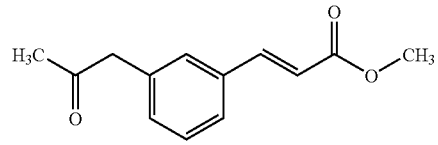

A solution of 3-bromophenylacetone (50.0 g, 235 mmol), methyl acrylate (40.4 g, 469 mmol), palladium(II)acetate (7.9 g, 35.2 mmol), tri-ortho-tolylphosphine (21.4 g, 70.4 mmol) and triethylamine (82 mL) in acetonitrile (900 mL) was heated at reflux under a nitrogen atmosphere for 16 hours. The reaction mixture was cooled to room temperature and the solvent removed in vacuo. Purification by flash column chromatography eluting with pentane:ethyl acetate 90:10 to 70:30 gave the title compound as an orange oil (54.3 g). $^1$H NMR (400 MHz, CD$_3$OD) δ: 2.15 (3H, s), 3.70 (2H, s), 3.77 (3H, s), 6.43–6.39 (1H, d), 7.20–7.18 (1H, d), 7.34–7.31 (2H, t), 7.41–7.39 (1H, d), 7.66–7.62 (1H, d); LRMS ESI: m/z 241 [M+Na]$^+$, 217 [M−H]$^−$.

Preparation 140: Methyl 3-[3-(2-oxopropyl)phenyl]propanoate

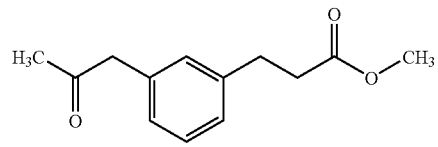

Prepared according to the procedure used for preparation 26 using preparation 139 to give the title compound as an orange oil. $^1$H NMR (400 MHz, CD$_3$OD) δ: 2.14 (3H, s), 2.64–2.60 (2H, t), 2.96–2.92 (2H, t), 3.66 (5H, s), 7.05–7.04 (2H, d), 7.11–7.09 (1H, d), 7.27–7.23 (1H, q); LRMS ESI m/z 243 [M+Na]$^+$, 219 [M−H]$^−$.

Preparation 141: Methyl [3-((2R)-2{[(1R)-1-phenylethyl]amino}propyl)phenyl]propanoate hydrochloride

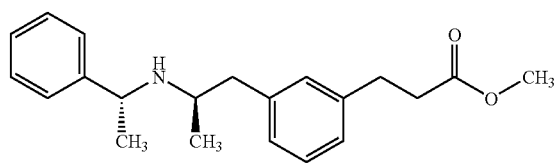

Prepared according to the procedure used for preparation 19, using preparation 140 to give the title compound as a white crystalline solid. $^1$H NMR (400 MHz, CD$_3$OD) δ: 1.18–1.16 (3H, d), 1.71–1.69 (3H, d), 2.62–2.56 (3H, m), 2.89–2.85 (2H, t), 3.20–3.12 (1H, m), 3.34–3.29 (1H, m), 3.61 (3H, s), 4.64–4.59 (1H, q), 6.92–6.91 (2H, d), 7.12–7.10 (1H, d), 7.23–7.19 (1H, t), 7.54–7.47 (5H, m); LRMS ESI m/z 326 [M+H]$^+$.

Preparation 142: 3-{3-[(2R)-2-((1R)-1-Phenylethylamino)propyl]phenyl}-propionic acid

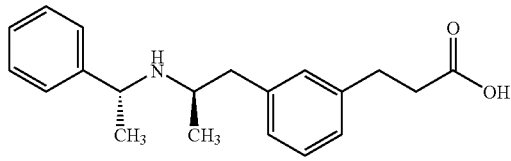

Preparation 141 (3.25 g, 8.98 mmol) and sodium hydroxide (5M, 9.0 mL, 45.0 mmol) were stirred in 1,4-dioxane (40 mL) and water (40 mL) for 18 h. The solvent was removed in vacuo and the material dissolved in water, acidified to pH 6 with hydrochloric acid (2M) which solidified over 18 h. The solid was filtered off and dried in vacuo (1.0 g, 36%). The filtrate was concentrated and tetrahydrofuran added and the mixture filtered. The filtrate was evaporated to leave a foam which was suspended in diethylether (×3) to yield a colourless foam (1.96 g, 70%). $^1$H NMR (400 MHz, CD$_3$OD) δ: 1.13 (3H, d), 1.62 (3H, d), 2.42 (2H, t), 2.55–2.64 (1H, m), 2.84 (2H, t), 3.08–3.42 (2H, m), 4.46–4.52 (1H, m), 6.86 (1H, d), 6.98 (1H, s), 7.11–7.22 (2H, m), 7.45–7.52 (5H, m); LCMS APCI m/z 312 [M+H]$^+$

Preparation 143: 1-(3,4-Dihydro-1H-isoquinolin-2-yl)-3-{3-[(2R)-2-((1R)-1-phenylethylamino)propyl]phenyl}propan-1-one

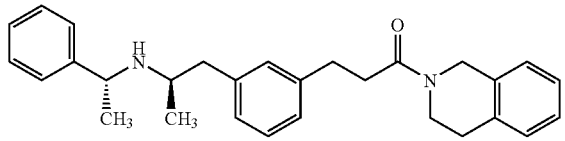

Preparation 142 (1.95 g, 6.27 mmol), triethylamine (2.62 mL, 19.0 mmol) in dichloromethane (80 mL) were treated with 2-chloro-1,3-dimethylimidazoline hexafluorophosphate (1.75 g, 6.27 mmol) and the resulting solution left to stir for 3 h. The solvent was removed and the residue taken up in ethyl acetate and washed with sat. sodium hydrogencarbonate (3×20 mL), brine (3×20 mL) and dried (Na$_2$SO$_4$). After filtration and removal of the solvent the material was purified by chromatography, eluting with dichloromethane:methanol:0.88 ammonia 99.7:0:0.3 to 96.7:3:0.3. The product was evaporated from diethylether (×3) to yield a semi-solid (2.3 g, 86%). $^1$H NMR (400 MHz, CDCl$_3$) δ: 0.88 (3H, d), 1.30 (3H, d), 2.42–2.50 (1H, m), 2.64–2.98 (8H, m), 3.55–3.62 (1H, m), 3.78–3.96 (2H, m), 4.51 (1H, s), 4.72 (1H, s), 6.88–7.38 (13H, m); LCMS APCI m/z 427 [M+H]$^+$

Preparation 144: 3-[3-((2R)-2-Aminopropyl)phenyl]-1-(3,4-dihydro-1H-isoquinolin-2-yl)propan-1-one

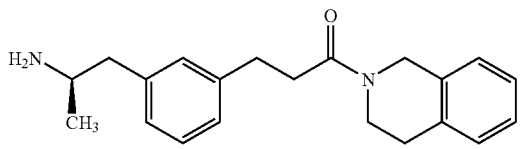

Preparation 143 (2.20 g, 5.16 mmol), ammonium formate (1.63 g, 26.0 mmol) and palladium hydroxide (500 mg) in ethanol (40 mL) were heated and stirred at 70° C. for 4 h. The mixture was filtered through a filter-aid and the solvent removed. The material was purified by chromatography, eluting with dichloromethane:methanol:0.88 ammonia 99.7:0:0.3 to 94.7:5:0.3 to yield a colourless oil which was evaporated from diethylether (×3) (1.26 g, 76%). $^1$H NMR (400 MHz, CDCl$_3$) δ: rotamers 1.10/1.11 (3H, 2×d), 2.43–2.48 (1H, m), 2.62–2.76 (3H, m), 2.78–2.86 (2H, m), 2.96–3.02 (2H, m), 3.08–3.18 (1H, m), 3.58 (1H, t), 3.81 (1H, t), 4.53/4.73 (2H, 2×s), 6.98–7.24 (8H, m); LCMS APCI m/z 323 [M+H]$^+$

Preparation 145: N-{2-Benzyloxy-5-[(1R)-1-(tert-butyldimethylsilanyloxy)-2-((1R)-2-{3-[3-(3,4-dihydro-1H-isoquinolin-2-yl)-3-oxo-propyl]phenyl}-1-methylethylamino)ethyl]phenyl}formamide

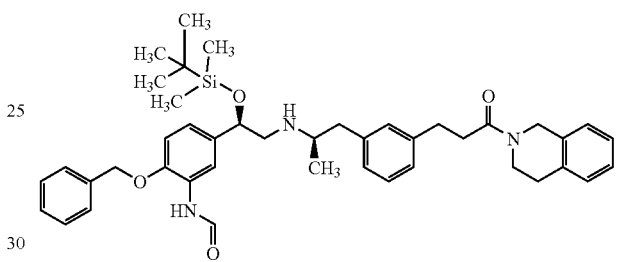

The title compound was prepared with preparation 144 and preparation 12, using a method similar to that of preparation 136 (216 mg, 67%). $^1$H NMR (400 MHz, CD$_3$OD) δ: rotamers −0.19 (3H, s), −0.01 (3H, s), 0.82 (9H, s), 0.98–1.04 (3H, s), 2.48–2.96 (11H, m), 3.57–3.62/3.72–3.76 (2H, m), 4.53–4.70 (3H, m), 5.18 (2H, m), 6.87–6.97 (3H, m), 6.99–7.18 (7H, m), 7.28–7.39 (3H, m), 7.45–7.60 (2H, m), 8.20 (d), 8.31 (d); LCMS APCI m/z 707 [M+H]$^+$

Preparation 146: N-{5-[(1R)-1-(tert-Butyldimethylsilanyloxy)-2-((1R)-2-{3-[3-(3,4-dihydro-1H-isoquinolin-2-yl)-3-oxo-propyl]phenyl}-1-methylethylamino)ethyl]-2-hydroxyphenyl}formamide

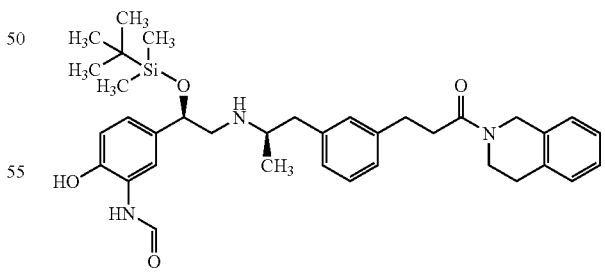

Prepared using the amide from preparation 145 and the method described for preparation 15 to yield a brown foam (280 mg, 100%). $^1$H NMR (400 MHz, CD$_3$OD) δ: rotamers −0.14 (3H, s), −0.03 (3H, s), 0.84 (9H, s), 1.08–1.12 (3H, m), 2.54–3.20 (11H, m), 3.60–3.65/3.74–3.77 (2H, 2×t), 4.56–4.66 (2H, 2×s), 4.78–4.84 (1H, m), 6.80–7.24 (1H, m), 8.10 (s), 8.31 (s); LCMS APCI m/z 617 [M+H]$^+$

EXAMPLE 1

N-Benzyl-2-(3-{2-[(2R)-2-(3-formylamino-4-hydroxyphenyl)-2-hydroxyethylamino]-2-methylpropyl}phenyl)acetamide

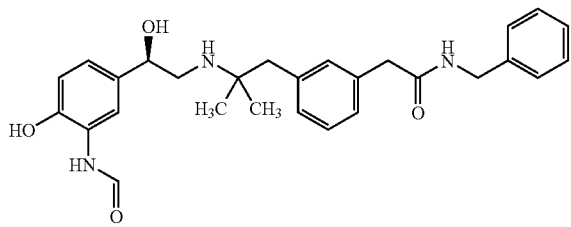

Preparation 15 (24 mg, 40 μmol), formic acid (0.5 mL), tetrahydrofuran (5 mL) and water (0.5 mL) were heated to 90° C. for 18 h. A further aliquot of formic acid (0.5 mL) and tetrahydrofuran (5 mL) were added and heating continued for a further 18 h. The solvent was removed and the product purified by chromatography (0–10% methanol in dichloromethane+0.3% ammonia). The product was dissolved in methanol (×3) and evaporated (10 mg). $^1$HNMR (CD$_3$OD, 400 MHz) δ: 1.05–1.09 (6H, m), 2.69–2.78 (2H, m), 2.78–2.83 (1H, m), 2.87–2.93 (1H, m), 3.53 (2H, s), 4.35 (2H, s), 4.65 (1H, dd), 6.82–6.86 (1H, m), 6.99 (1H, dd), 7.03–7.06 (1H, m), 7.13–7.28 (7H, m), 8.08 (d), 8.28 (s), 8.55 (s), 8.61 (s); MS (APCI) m/z 476 [M+H]$^+$; HRMS C$_{28}$H$_{33}$N$_3$O$_4$ 476.2544 [M+H]$^+$ found 476.2533.

EXAMPLE 2

N-(3,4-Dimethylbenzyl)-2-(3-{2-[(2R)-2-(3-formylamino-4-hydroxy-phenyl)-2-hydroxyethylamino]-2-methylpropyl}phenyl)acetamide

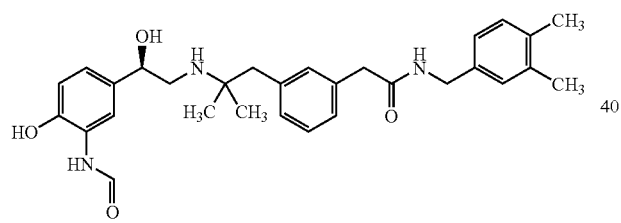

Prepared using the amide from Preparation 16 and the method described for Example 1. $^1$H NMR (CD$_3$OD, 400 MHz) δ: 1.05–1.08 (6H, m), 2.18 (3H, s), 2.19 (3H, s), 2.67–2.94 (4H, m), 3.52 (2H, s), 4.27 (2H, s), 4.62 (1H, dd), 4.65 (1H, dd), 6.81–7.06 (6H, m), 7.12–7.24 (3H, m), 8.07 (d), 8.27 (s), 8.55 (s), 8.61 (s). MS (APCI) M/Z 504 [M+H]$^+$; HRMS C$_{30}$H$_{37}$N$_3$O$_4$ 504.2857 [M+H]$^+$ FOUND 504.2842.

EXAMPLE 3

N-[4-(dimethylamino)benzyl]-2-{3-[(2R)-2-({(2R)-2-[3-(formylamino)-4-hydroxyphenyl]-2-hydroxyethyl}amino)propyl]phenyl}acetamide

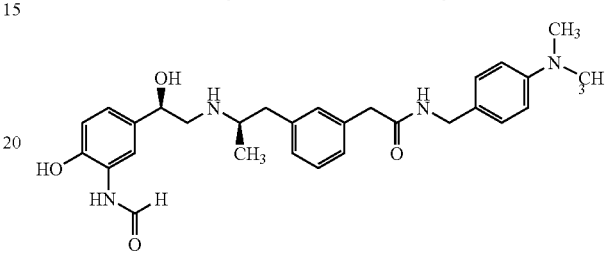

A mixture of the product of preparation 27, (131 mg, 0.21 mmol) and triethylamine trihydrofluoride (16 μL, 0.10 mmol) in tetrahydrofuran (2 mL) was stirred at room temperature for 3 days. The mixture was then concentrated in vacuo and the residue was purified by column chromatography on silica gel, eluting with dichloromethane:methanol:0.88 ammonia, 100:0:0 to 90:10:1 to afford the title compound as a brown foam in 36% yield, 18 mg. $^1$H NMR (400 MHz, CD$_3$Cl$_3$) δ: 1.07 (3H, m), 2.57 (1H, dd), 2.67–2.76 (2H, m), 2.85–2.99 (2H, m), 2.87 (6H, s), 3.47 (1H, m), 4.23 (2H, s), 4.68 (1H, dd), 6.67–6.71 (2H, m), 6.77–6.79 (2H, d), 6.90 (1H, m), 6.97–7.70 (m, 6H), 7.97 (d), 8.27 (s), 8.35 (s); LRMS APCI m/z 619 [M+H]$^-$

EXAMPLES 4 TO 12

The following compounds, of the general formula shown below were prepared using a method similar to that described for example 3. The appropriate starting material was treated with 1–1.1 eq of triethylamine trihydrofluoride at room temperature for 18–72 hours.

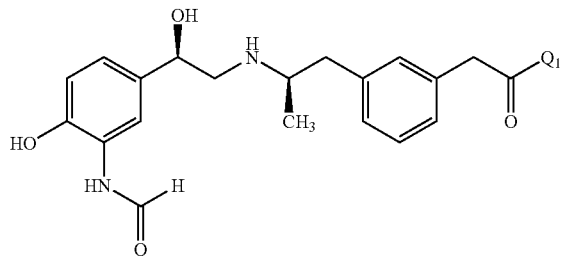

| No. | Q$_1$ | Data | Yield |
|---|---|---|---|
| 4 | ![structure] | $^1$H NMR(400MHz, CD$_3$Cl$_3$) δ: 1.00(3H, d), 2.09(3H, s), 2.55(1H, dd), 2.64–2.71(2H, m), 2.83–2.93(2H, m), 3.13(m, 1H), 3.49 (2H, s), 4.30(2H, s), 4.64–4.69(1H, m), 6.76 (1H, d), 6.89(1H, dd), 6.98(1H, d), 7.06 (1H, m), 7.09–7.19(4H, m), 7.45(2H, d), 7.99(d), 8.03(s), 8.28(s), 8.35(s); LRMS APCl m/z 517 [M − H]$^-$ | 17% |

-continued

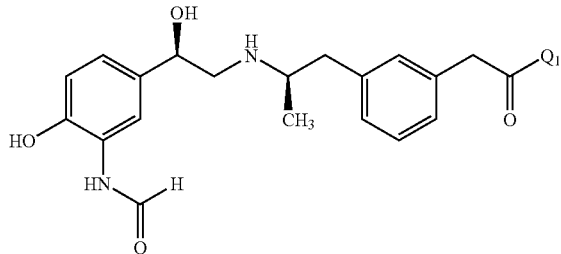

| No. | Q₁ | Data | Yield |
|---|---|---|---|
| 5 | -HN-CH₂-C₆H₄-C(O)NH₂ | ¹H NMR(400MHz, CD₃Cl₃) δ: 1.09(3H, d), 2.60(1H, dd), 2.74–2.82(2H, m), 2.90–2.96 (1H, m), 3.00–3.08(1H, m), 3.53(2H, s), 4.40(2H, s), 4.61(1H, dd), 6.78(1H, d), 6.91(1H, dd), 7.02(1H, d), 7.08–7.10(1H, m), 7.12–7.25(3H, m), 7.29(2H, d), 7.78 (2H, d), 7.99(d), 8.28(s), 8.56(s) LRMS APOI m/z 503 [M − H]⁻ | 12% |
| *6 | -HN-CH₂-(3-biphenyl)-4'-OH | ¹H NMR(400MHz, CD₃OD) δ: 1.05, 1.07 (3H, d), 2.54–3.06(5H, m), 3.53(2H, s), 4.40(2H, s), 4.60–4.65(1H, m), 6.80–7.42 (14H, m), 8.00(1H, s), 8.27(s), 8.59(s); LRMS APCl m/z 554 [M + H]⁺ | 10% |
| *7 | -HN-CH₂-(3,5-diMe-4-OH-C₆H₂) | ¹H NMR(400MHz, CD₃OD) δ: 1.07, 1.08 (3H, d), 2.14(6H, s), 2.54–3.02(5H, m), 3.47(2H, s), 4.18(2H, m), 4.56–4.64(1H, m)6.76–7.22(8H, m), 7.97(1H, s), 8.27(s), 8.56(s); LRMS APCl m/z 506 [M + H]⁺ | 31% |
| *8 | -HN-CH₂-(2-OH-1-naphthyl) | ¹H NMR(400MHz, CD₃OD) δ: 0.96, 0.97 (3H, d), 2.42–2.84(5H, m), 3.46(2H, s), 4.54–4.60(1H, m), 4.78(2H, s), 6.76–7.40 (8H, m), 7.66–7.74(3H, m), 7.85–7.91(1H, m), 7.96(1H, s), 8.27(s), 8.54(s); LRMS APCl m/z 528 [M + H]⁺ | 38% |
| *9 | -HN-CH₂-(2-OH-5-Cl-C₆H₃) | ¹H NMR(400MHz, CD₃OD) δ: 1.07, 1.08 (3H, d), 2.58–3.00(5H, m), 3.51(2H, s), 4.29(2H, s), 4.58–4.64(1H, m), 6.71–7.23 (9H, m), 7.96(1H, s), 8.28(s), 8.56(s); LRMS APCl m/z 512 [M + H]⁺ | 25% |
| *10 | -HN-CH₂-(2-OH-3,5-diCl-C₆H₂) | ¹H NMR(400MHz, CD₃OD) δ: 1.09, 1.10 (3H, d), 2.58–3.04(5H, m), 3.52(2H, s), 4.32(2H, s), 4.60–4.64(1H, m), 7.05–7.24 (8H, m), 7.97(1H, s), 8.29(s), 8.57(s); LRMS APCl m/z 546 [M + H]⁺ | 24% |
| *11 | -HN-CH₂-(6-OH-2-naphthyl) | ¹H NMR(400MHz, CD₃OD) δ: 1.02, 1.04 (3H, d), 2.54–2.94(5H, s), 3.52(2H, s), 4.45 (2H, s), 4.55–4.60(1H, m), 6.76–7.29(9H, m), 7.53–7.61(3H, m), 7.96(1H, s), 8.28(s), 8.55(s); LRMS APCl m/z 528 [M + H]⁺ | 30% |
| *12 | -HN-CH₂-(4-biphenyl)-4'-OH | ¹H NMR(400MHz, CD₃OD) δ: 1.05, 1.06 (3H, d), 2.46–2.98(5H, m), 3.51(2H, s), 4.36(2H, s), 4.52–4.60(1H, m), 6.75–7.25 (10H, m), 7.39–7.47(4H, m), 7.96(1H, s), 8.27(s), 8.54(s); LRMS APCl m/z 554 [M + H]⁺ | 35% |

-continued

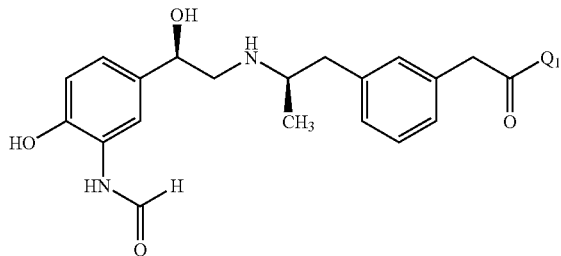

| No. | Q₁ | Data | Yield |
|---|---|---|---|

\* crude compounds were azeotroped with 2M methanolic ammonia before purification by column chromatography on silica gel, eluting with dichloromethane:methanol:0.88 ammonia 90:10:1. This was followed by further azeotropes in methanol (x3) and diethyl ether(x3) to afford desired products as white solids

EXAMPLES 13 TO 23

The following compounds, of the general formula shown below were prepared using a method similar to that described for example 3. The appropriate starting material was treated with 1–1.1 eq of triethylamine trihydrofluoride at room temperature for 18–72 hours.

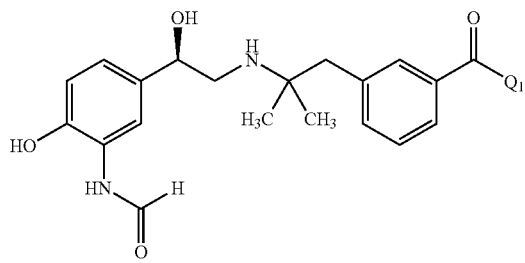

| No. | $Q_1$ | Data | Yield |
|---|---|---|---|
| 13 | 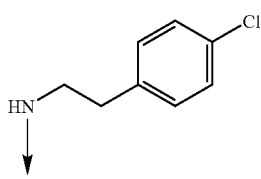 | $^1$H NMR(400MHz, CD$_3$OD) δ: 1.09, 1.10 (3H, 2xs), 1.14, 1.16(3H, 2xs), 2.76–3.04 (6H, m), 3.56(2H, m), 4.67(1H, dd), 6.84 (1H, d), 7.02(1H, m), 7.20–7.28(4H, m), 7.33–7.40(2H, m), 7.60–7.67(2H, m), 8.12 (1H, d), 8.29(s), 8.64(s); LRMS ESI m/z 534 [M + Na]$^+$ | 65% |
| 14 | 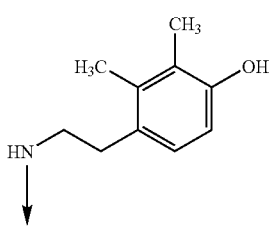 | $^1$H NMR(400MHz, CD$_3$OD) δ: 1.06(3H, s), 1.13(3H, s), 2.10(3H, s), 2.21(3H, s), 2.70–3.02(6H, m), 3.51(2H, t), 4.62–4.68(1H, m), 6.79–6.81(1H, m), 6.82–6.87(2H, m), 7.01–7.07(1H, m), 7.31–7.39(2H, m), 7.69 (2H, m), 8.09(1H, s), 8.29(s), 8.63(s); LRMS APCl m/z 520 [M + H]$^+$ | 90% |
| *15 | 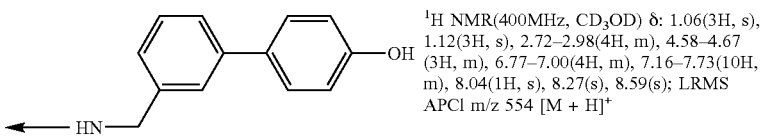 | $^1$H NMR(400MHz, CD$_3$OD) δ: 1.06(3H, s), 1.12(3H, s), 2.72–2.98(4H, m), 4.58–4.67 (3H, m), 6.77–7.00(4H, m), 7.16–7.73(10H, m), 8.04(1H, s), 8.27(s), 8.59(s); LRMS APCl m/z 554 [M + H]$^+$ | 39% |

-continued

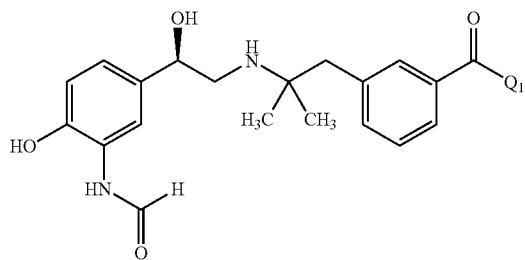

| No. | Q₁ | Data | Yield |
|---|---|---|---|
| 16 | (4'-hydroxybiphenyl-4-yl)methyl-NH- | ¹H NMR(400MHz, CD₃OD) δ: 1.06(3H, s), 1.13(3H, s), 2.72–3.00(4H, m), 4.54–4.70 (3H, m), 6.78–6.86(3H, m), 6.97–6.99(1H, d), 7.34–7.58(8H, m), 7.71–7.76(2H, m), 8.05(1H, s), 8.27(s), 8.59(s); LRMS APCl m/z 554 [M + H]⁺ | 41% |
| *17 | 2-(4-hydroxy-2,5-dimethylphenyl)ethyl-NH- | ¹H NMR(400MHz, CD₃OD) δ: 1.09(3H, s), 1.16(3H, s), 2.08(3H, s), 2.21(3H, s), 2.75–3.06(6H, m), 3.45–3.51(2H, m), 4.66–4.71 (1H, m), 6.53(1H, s), 6.83–6.88(3H, m), 7.02–7.04(1H, m), 7.32–7.41(2H, m), 7.63–7.68(2H, m), 8.11(s), 8.29(s), 8.63(s); LRMS APCl m/z 520 [M + H]⁺⁻ | 40% |
| *18 | 2-(4-hydroxy-3-methylphenyl)ethyl-NH- | ¹H NMR(400MHz, CD₃OD) δ: 1.06(3H, s), 1.13(3H, s), 2.13(3H, s), 2.71–3.00(6H, m), 3.47–3.56(2H, m), 4.64–4.69(1H, m), 6.63–6.65(1H, m), 6.83–7.39(6H, m), 7.60–7.69 (2H, m), 8.09(1H, s), 8.29(s), 8.63(s); LRMS APCl m/z 506 [M + H]⁺⁻ | 43% |
| *19 | (2-hydroxynaphthalen-1-yl)methyl-NH- | ¹H NMR(400MHz, CD₃OD) δ: 1.09(3H, s), 1.14(3H, s), 2.77–3.00(4H, m), 4.63–4.67 (1H, m), 4.98(2H, s), 6.38–6.40(1H, m), 6.81–6.83(1H, m), 7.12–7.14(1H, d), 7.26–7.48(5H, m), 7.70–7.78(4H, m), 8.06(1H, s), 8.28(s), 8.60(s); LRMS APCl m/z 528 [M + H]⁺ | 33% |
| *20 | (4-hydroxy-3,5-dimethylphenyl)methyl-NH- | ¹H NMR(400MHz, CD₃OD) δ: 1.09(3H, s), 1.15(3H, s), 2.17(6H, s), 2.75–3.00(4H, m), 4.37–4.46(2H, m), 4.64–4.82(1H, m), 6.79–6.82(1H, m), 6.91(2H, s), 6.97–7.01(1H, m), 7.33–7.40(2H, m), 7.68–7.74(2H, m), 8.05(1H, s), 8.28(s), 8.61(s); LRMS APCl m/z 506 [M + H]⁺ | 48% |
| *21 | (3,6-dichloro-2-hydroxyphenyl)methyl-NH- | ¹H NMR(400MHz, CD₃OD) δ: 1.13(3H, s), 1.18(3H, s), 2.80–3.06(4H, m), 4.52(2H, m), 4.64–4.77(1H, m), 6.82–6.84(1H, m), 7.00–7.25(3H, m), 7.39–7.44(2H, m), 7.73–7.78(2H, m), 8.08(1 H, s), 8.29(s), 8.62(s); LRMS APCl m/z 546 [M + H]⁺ | 20% |
| *22 | (7-hydroxynaphthalen-2-yl)methyl-NH- | ¹H NMR(400MHz, CD₃OD) δ: 1.07(3H, s), 1.13(3H, s), 2.73–2.98(4H, m), 4.63–4.76 (3H, m), 6.75–6.78(1H, m), 6.95–7.05(3H, m), 7.33–7.40(3H, m), 7.60–7.80(5H, m), 8.04(1H, s), 8.26(s), 8.60(s); LRMS APCl m/z 528 [M + H]⁺ | 62% |

-continued

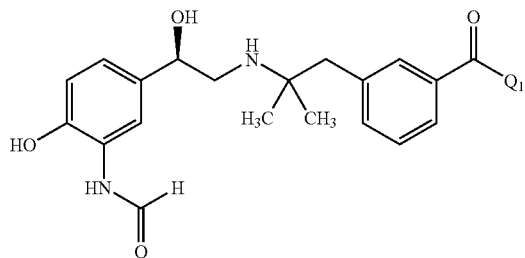

| No. | Q₁ | Data | Yield |
|---|---|---|---|
| 23 |  (structure with HN-CH₂-C(CH₃)₂-CH₂-phenyl-OH) | $^1$H NMR(400MHz, CD$_3$OD) δ: 1.07(3H, s), 1.11(3H, s), 1.33(6H, s), 2.74–2.96(4H, m), 3.52(2H, s), 4.56–4.70(2H, m), 6.72–6.74 (1H, d), 6.82–6.84(1H, d), 7.04(1H, m), 7.20–7.36(4H, m), 7.49–7.57(2H, m) 8.06 (1H, s), 8.29(s), 8.63(s); LRMS APCl m/z 520 [M + H]$^+$ | 35% |

Example 14: was azeotroped with 2M methanolic ammonia before purification.
*crude compounds were azeotroped with 2M methanolic ammonia before purification by column chromatography on silica gel, eluting with dichloromethane:methanol:0.88 ammonia 90:10:1. This was followed by further azeotropes in methanol(x3) and diethyl ether(x3) to afford desired products as white solids

EXAMPLES 24 TO 27

The following compounds, of the general formula shown below were prepared using a method similar to that described for example 3. The appropriate starting material was treated with 1–1.1 eq of triethylamine trihydrofluoride at room temperature for 18–72 hours.

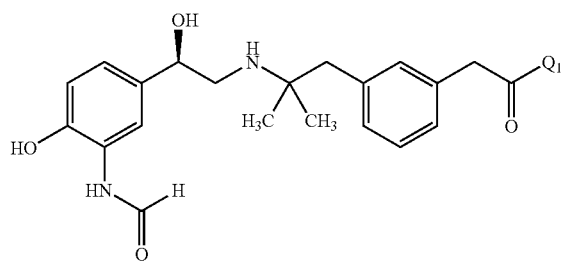

| No. | Q₁ | Data | Yield |
|---|---|---|---|
| 24 | HN-CH₂-phenyl-C(O)-O-CH₃ | $^1$H NMR(400MHz, CD$_3$OD) δ: 1.01(3H, s), 1.03(3H, s), 2.63–2.87(4H, m), 3.52(2H, s), 3.84(3H, s), 4.38(2H, s), 4.56–4.60(1H, m), 6.78–6.80(1H, m), 6.94–6.97(1H, m), 7.00–7.02(1H, m), 7.11–7.20(4H, m), 7.26–7.29 (2H, m), 7.87–7.89(2H, d), 7.98–7.99(d), 8.21 (s), 8.54(s); LRMS ESI m/z 534 [M + H]$^-$ | 75% |
| 25 | H₃C-CH₂-N(CH₂-phenyl(OH)(Cl)) | $^1$H NMR(400MHz, CDCl$_3$) δ: 0.96–1.04(9H, m), 2.60–2.88(4H, m), 3.16–3.33(2H, m), 3.66, 3.79(2H, 2xs), 4.61, 4.66(2H, 2xs), 4.64, 4.79(1H, m), 6.56(1H, m), 6.73–6.79 (2H, m), 6.92–7.19(6H, m), 7.98(1H, m), 8.23 (s), 8.65(s); LRMS APCl m/z 554 [M + H]$^+$ | 41% |

-continued

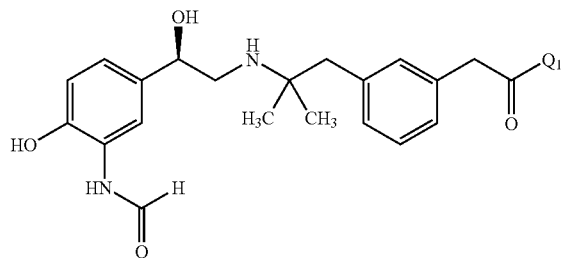

| No. | Q₁ | Data | Yield |
|---|---|---|---|
| 26 | (4-hydroxybiphenyl-4'-ylmethylamino) | $^1$H NMR(400MHz, CDCl$_3$) δ: 0.98(3H, s), 1.00(3H, s), 2.61–2.84(4H, m), 3.48(2H, s), 4.30(2H, s), 4.54–4.57(1H, m), 6.75–6.77(3H, m), 6.91–6.94(1H, m), 6.96–6.99(1H, m), 7.08–7.18(6H, m), 7.33–7.40(4H, m), 7.98(s), 8.21(s), 8.56(s); LRMS ESI m/z 568 [M + H]$^+$ | 93% |
| 27 | (3-chloro-4-hydroxybenzylamino) | $^1$H NMR(400MHz, CD$_3$OD) δ: 1.05(3H, s), 1.08(3H, s), 2.66–2.93(4H, m), 3.52(2H, m), 4.34(2H, s), 4.61(1H, m), 6.81(1H, m), 6.79 (1H, d), 6.81(1H, d), 6.99–7.22(6H, m), 8.06 (1H, d), 8.28(s), 8.61(s); LRMS APCI m/z 526 [M + H]$^+$ | 44% |

Example 28

N-1-Adamantyl-2-{3-[(2R)-2-({(2R)-2-[3-(formylamino)phenyl]-2-hydroxyethyl}amino)propyl]phenyl}acetamide

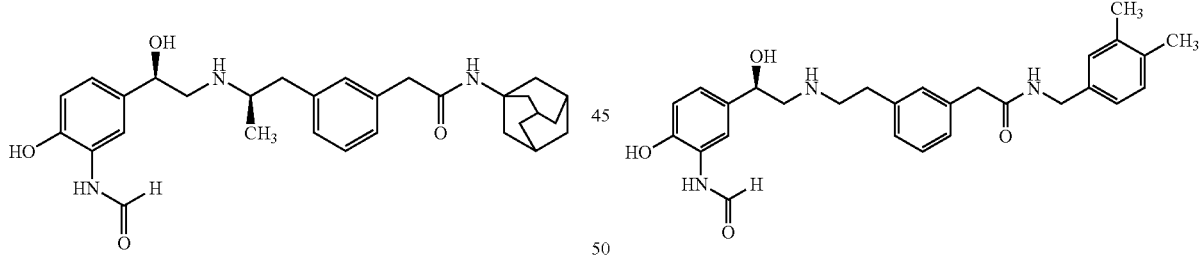

a mixture of the product of preparation 34 (500 mg, 0.81 mmol) and ammonium fluoride (200 mg, 5.4 mmol) in methanol (5 mL) and water (1.5 mL) was heated at 40° C. for 18 hours. The reaction mixture was then concentrated in vacuo and the residue was purified by column chromatography on silica gel, eluting with dichloromethane: methanol: 0.88 ammonia, 90:10:0.1, to afford the title compound as a foam in 84% yield, 347 mg. $^1$H NMR (400 MHz, CD$_3$OD) δ: 1.05–1.10 (m, 3H), 1.64–1.74 (6H, m), 1.98–2.03 (9H, m), 2.36–2.98 (5H, m), 3.36 (2H, s), 4.46–4.60 (1H, m), 6.46–7.20 (6H, m), 7.96 (1H, s), 8.28 (s), 8.56 (s); LRMS ESI m/z 506 [M+H]$^+$

EXAMPLE 29

N-(3,4-Dimethylbenzyl)-2-{3-[2-({(2R)-2-[3-(formylamino)-4-hydroxy phenyl]-2-hydroxyethyl}amino)ethyl]phenyl}acetamide The title compound was prepared from the product of preparation 102, using a similar method to that of examples 4–12, as solid. $^1$H NMR (400 MHz, CD$_3$OD) 2.20 (6H, m), 3.00 (2H, m), 3.18 (2H, m), 3.28 (2H, m), 3.56 (2H, s), 4.28 (2H, s), 4.81 (1H, m), 6.81 (1H, d), 6.98 (2H, m), 7.05 (2H, m), 7.20 (4H, m), 7.30 (1H, t), 8.10 (s), 8.30 (s); LRMS ESI 476 [M+H]$^+$

EXAMPLES 30 TO 37

The following compounds, of the general formula shown below were prepared using a method similar to that described for example 3. The appropriate starting material was treated with 1–1.1 eq of triethylamine trihydrofluoride at room temperature for 18–72 hours.

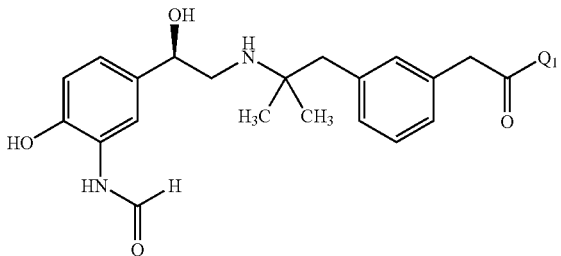

| No. | Q₁ | Data | Yield |
|---|---|---|---|
| 30 | HN~⟍–⟨phenyl⟩–S–CH₃ (4-methylthiobenzyl) | ¹H NMR (400 MHz, CD₃OD) δ: 0.94 (3H, s), 0.97 (3H, s), 2.33 (3H, s), 2.56–2.81 (4H, m), 3.43 (2H, s), 4.21 (2H, s), 4.52–4.55 (1H, m), 6.73 (1H, m), 6.89–6.95 (2H, m), 7.03–7.13 (7H, m), 7.98 (d), 8.19 (s), 8.52 (s); LRMS ESI m/z 522 [M + H]⁻ | 26% |
| 31 | HN~⟍–⟨phenyl⟩–CF₃ | ¹H NMR (400 MHz, CD₃OD) δ: 0.99 (3H, s), 1.01 (3H, s), 2.60–2.85 (4H, m), 3.49 (2H, s), 4.36 (2H, s), 4.54–4.59 (1H, m), 6.75 (1H, d), 6.92 (1H, dd), 6.98 (1H, d), 7.08–7.18 (3H, m), 7.31 (2H, d), 7.48 (2H, d), 8.00 (d), 8.22 (s), 8.64 (s); LRMS APCI m/z 544 [M + H]⁺ | 27% |
| 32 | HN~⟍–⟨phenyl⟩–CN | ¹H NMR (400 MHz, CD₃OD) δ: 0.97 (3H, s), 1.00 (3H, s), 2.59–2.86 (4H, m), 3.48 (2H, s), 4.34 (2H, s), 4.53–4.56 (1H, m), 6.74 (1H, d), 6.92 (1H, d), 6.98 (1H, bd), 7.08–7.17 (3H, m), 7.29 (2H, d), 7.55 (2H, d), 8.00 (1H, d), 8.22 (s), 8.64 (s); LRMS ESI m/z 501 [M + H]⁺ | 38% |
| 33 | HN~⟍–⟨phenyl⟩–OCF₃ | ¹H NMR (400 MHz, CD₃OD) δ: 1.00 (3H, s), 1.02 (3H, s), 2.62–2.86 (4H, m), 3.47 (2H, s), 4.30 (2H, s), 4.55–4.58 (1H, m), 6.82 (1H, d), 6.99 (1H, dd), 7.04 (1H, d), 7.14–7.23 (5H, m), 7.29 (1H, s), 7.31 (1H, s), 8.07 (1H, d0, 8.29 (s), 8.64 (s); LRMS APCI m/z 560 [M + H]⁺ | 49% |
| 34 | HN~⟍–⟨phenyl⟩–⟨phenyl⟩–OH (biphenyl-4-ol) | ¹H NMR (400 MHz, CD₃OD) δ: 0.93 (3H, s), 0.96 (3H, s), 2.51–2.83 (4H, m), 3.47 (2H, s), 4.34 (2H, s), 4.52–4.55 (1H, m), 6.73–6.76 (3H, m), 6.90–6.97 (2H, m), 7.04–7.06 (2H, m), 7.12–7.14 (2H, m), 7.20–7.33 (5H, m), 7.99 (1H, bs), 8.21 (s), 8.54 (s); LRMS APCI m/z 568 [M + H]⁺ | 82% |
| 35 | HN~⟍–⟨phenyl(HO, Cl)⟩ (2-hydroxy-5-chlorobenzyl) | ¹H NMR (400 MHz, CD₃OD) δ: 0.99 (3H, s), 1.01 (3H, s), 2.61–2.86 (4H, m), 3.47 (2H, s), 4.23 (2H, s), 4.55–4.58 (1H, m), 6.64–6.66 (1H, m), 6.75–6.79 (1H, m), 6.92–7.16 (8H, m), 7.99 (1H, d), 8.22 (s), 8.54 (s); LRMS APCI m/z 526 [M + H]³⁰ | 50% |
| 36 | HN–⟨tetrahydrothiopyran-4-yl⟩ | ¹H NMR (400 MHz, CD₃OD) δ: 1.02 (3H, s), 1.04 (3H, s), 1.44–1.55 (2H, m), 2.00–2.04 (2H, m), 2.52–2.87 (8H, m), 2.39 (2H, s), 3.55–3.61 (1H, m), 4.56–4.59 (1H, m), 6.76 (1H, d), 6.93–6.98 (2H, m), 7.07–7.16 (3H, m), 8.00 (1H, d), 8.23 (s), 8.55 (s); LRMS APCI m/z 486 [M + H]⁺ | 40% |
| 37 | HN~⟍–⟨phenyl⟩–S(O)₂CH₃ | ¹H NMR (400 MHz, CD₃OD) δ: 1.06 (3H, s), 1.08 (3H, s), 2.67–2.95 (4H, m), 3.07 (3H, s), 3.56 (2H, s), 4.45 (2H, s), 4.60 (1H, dd), 6.81 (1H, d), 6.98 (1H, dd), 7.04 (1H, d), 7.14–7.25 (4H, m), 7.44 (2H, d), 7.84 (2H, d), 8.06 (1H, d), 8.28 (s), 8.61 (s); LRMS APCI m/z 554 [M + H]⁺ | |

EXAMPLES 38 TO 46

The appropriate amides, triethylamine trihydrofluoride (1 equivalent) in tetrahydrofuran (5 mL) was stirred at room temperature for 2 days. The mixture was then concentrated in vacuo and the residue treated with methanolic ammonia and evaporated (×3) to leave a foam which was taken up in dichloromethane:methanol:0.88 ammonia, 90:10:1 filtered, then purified by column chromatography on silica gel, eluting with dichloromethane: methanol: 0.88 ammonia, 90:10:1 to afford the title compound as a film which was dissolved in methanol and evaporated (×3), then suspended in diethylether and evaporated (×3) to yield a white solid.

| No. | $Q_1$ | Data | Yield |
|---|---|---|---|
| 38 | HN-CH2CH2-phenyl | $^1$H NMR (400 MHz, CD$_3$OD) δ: 1.07 (3H, s), 1.14 (3H, s), 2.73–3.00 (6H, m), 3.57–3.62 (2H, m), 4.65–4.70 (1H, m), 6.83 (1H, d), 7.01–7.05 (1H, m), 7.16–7.40 (7H, m), 7.61–7.67 (2H, m), 8.09 (1H, d), 8.29 (s), 8.63 (s); LRMS APCl m/z 476 [M + H]$^+$ | 52% |
| 39 | HN-CH2-cyclohexyl | $^1$H NMR (400 MHz, CD$_3$OD) δ: 0.94–1.34 (11H, m), 1.58–1.80 (6H, m), 2.74–3.00 (4H, m), 3.14–3.30 (2H, m), 4.65–4.69 (1H, m), 6.83 (1H, d), 7.02–7.06 (1H, m), 7.32–7.31 (2H, m), 7.37–7.73 (2H, m), 8.07 (1H, d), 8.30 (s), 8.63 (s); LRMS APCl m/z 468 [M + H]$^+$ | 65% |
| 40 | N-piperidinyl | $^1$H NMR (400 MHz, CD$_3$OD) δ: 1.09 (3H, s), 1.11 (3H, s), 1.46–1.80 (6H, m), 2.76–2.95 (4H, m), 3.35 (2H, bs), 3.69 (2H, bs), 4.62–4.65 (1H, m), 6.82 (1H, d), 6.99–7.02 (1H, m), 7.18–7.30 (3H, m), 7.33–7.37 (1H, m), 8.04 (1H, s), 8.29 (s), 8.63 (s); LRMS APCl m/z 438 [M + H]$^+$ | 69% |
| 41 | HN-CH2CH2-(3-CF3-phenyl) | $^1$H NMR (400 MHz, CD$_3$OD) δ: 1.04 (3H, s), 1.11 (3H, s), 2.69–3.03 (6H, m), 3.47–3.67 (2H, m), 4.63–4.67 (1H, m), 6.82 (1H, d), 7.00–7.06 (1H, m), 7.30–7.64 (8H, m), 8.08 (1H, s), 8.29 (s), 8.63 (s); LRMS APCl m/z 542 [M + H]$^+$ | 52% |
| 42 | HN-CH2CH2CH2-phenyl | $^1$H NMR (400 MHz, CD$_3$OD) δ: 1.05 (3H, s), 1.13 (3H, s), 1.88–1.98 (2H, m), 2.64–2.80 (4H, m), 2.89–3.00 (2H, m), 3.38–3.46 (2H, m), 4.63–4.67 (1H, m), 6.81 (1H, d), 6.98–7.08 (1H, m), 7.10–7.30 (5H, m), 7.30–7.40 (2H, m), 7.62–7.70 (2H, m), 8.08 (1H, s), 8.27 (s), 8.61 (s); LRMS APCl m/z 488 [M + H]$^+$ | 59% |
| 43 | HN-indanyl | $^1$H NMR (400 MHz, CD$_3$OD) δ: 1.06 (3H, s), 1.13 (3H, s), 2.71–3.04 (8H, s), 4.50–4.80 (2H, m), 6.80 (1H, d), 6.96–7.06 (1H, m), 7.11–7.20 (4H, m), 7.31–7.42 (2H, m), 7.68–7.71 (2H, m), 8.06 (1H, d), 8.27 (s), 8.61 (s); LRMS APCl m/z 488 [M + H]$^+$ | 56% |
| 44 | HN-CH2CH2-(2-pyridyl) | $^1$H NMR (400 MHz, CD$_3$OD) δ: 1.04 (3H, s), 1.11 (3H, s), 2.70–2.97 (4H, m), 3.06 (2H, t), 3.71 (2H, t), 4.64–4.68 (1H, m), 6.82–6.86 (1H, m), 7.00–7.06 (1H, m), 7.19–7.38 (4H, m), 7.61–7.64 (2H, m), 7.72 (1H, t), 8.08 (1H, s), 8.28 (s), 8.45 (1H, d), 8.63 (s); LRMS APCl m/z 477 [M + H]$^+$ | 62% |

-continued

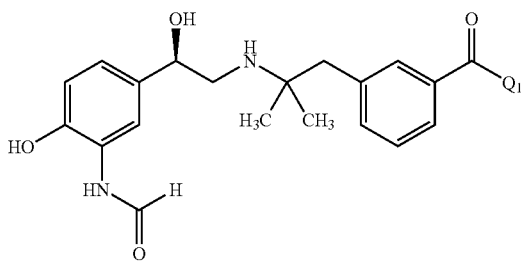

| No. | Q₁ | Data | Yield |
|---|---|---|---|
| 45 | (4-methoxyphenethylamino) | ¹H NMR (400 MHz, CD₃OD) δ: 1.05 (3H, s), 1.12 (3H, s), 2.70–3.00 (6H, m), 3.50–3.60 (2H, m), 3.74 (3H, s), 4.63–4.66 (1H, m), 6.80–6.86 (3H, m), 7.00–7.06 (1H, m), 7.12 (2H, d), 7.30–7.39 (2H, m), 7.60–7.65 (2H, m), 8.09 (1H, s), 8.29 (s), 8.63 (s); LRMS APCl m/z 506 [M + H]⁺ | 28% |
| 46 | (4-sulfamoylphenethylamino) | ¹H NMR (400 MHz, CD₃OD) δ: 1.13 (3H, s), 1.18 (3H, s), 2.75–3.06 (6H, m), 3.62 (2H, t), 4.68–4.75 (1H, m), 6.85 (1H, d), 7.03 (1H, d), 7.37–7.45 (4H, m), 7.62–7.70 (2H, m), 7.80 (2H, d), 8.12 (1H, s), 8.30 (s), 8.64 (s); LRMS APCl m/z 555 [M + H]⁺ | 27% |
| 47 | (1,2,3,4-tetrahydroisoquinolin-2-yl) | ¹H NMR (400 MHz, CD₃OD) δ: 1.14–1.24 (6H, m), 2.80–3.06 (7H, m), 3.80–3.84 (1H, bs), 3.93–3.97 (1H, bs), 4.55–4.59 (1H, bs), 4.68–4.73 (1H, m), 6.87 (1H, dd), 7.00–7.15 (3H, m), 7.20–7.30 (2H, m), 7.82–7.87 (1H, m), 8.09 (1H, s), 8.28 (s), 8.63 (s); LRMS APCl m/z 488 [M + H]⁺ | 57% |
| 48 | (adamantylamino) | ¹H NMR (400 MHz, CD₃OD) δ: 1.14 (3H, s), 1.19 (3H, s), 1.74 (6H, s), 2.07 (3H, s), 2.15 (6H, s), 2.76–3.10 (4H, m), 4.56 (1H, bs), 4.64–4.72 (1H, m), 6.84 (1H, d), 7.03 (1H, d), 7.31–7.39 (2H, m), 7.58–7.62 (2H, m), 8.11 (1H, s), 8.30 (s), 8.63 (s); LRMS APCl m/z 506 [M + H]⁺ | 8% |
| 49 | (2-azatricyclic) | ¹H NMR (400 MHz, CD₃OD) δ: 1.00–1.08 (6H, m), 2.00 (1H, d), 2.26–2.38 (1H, m), 2.63–3.30 (7H, m), 3.40–3.58 (2H, m), 4.46–4.56 (1H, d), 4.60–4.68 (1H, m), 6.58–6.68 (2H, m), 6.80–6.90 (1H, m), 6.96–7.34 (7H, m), 8.08 (1H, s), 8.30 (s), 8.63 (s); LRMS APCl m/z 514 [M + H]⁺ | 19% |
| 50 | (5-chloro-2-hydroxyphenethylamino) | ¹H NMR (400 MHz, CD₃OD) δ: 1.10 (3H, s), 1.14 (3H, s), 2.27–3.00 (6H, m), 3.57–3.60 (2H, t), 4.63–4.71 (1H, m), 6.71 (1H, d), 6.82 (1H, d), 6.99–7.09 (3H, m), 7.32–7.39 (2H, m), 7.61–7.67 (2H, m), 8.08 (1H, s), 8.29 (s), 8.63 (s); LRMS APCl m/z 526 [M + H]⁺ | 17% |

EXAMPLES 51 TO 55

The following compounds, of the general formula shown below were prepared using a method similar to that described for example 3. The appropriate starting material was treated with 1–1.1 eq of triethylamine trihydrofluoride at room temperature for 18–72 hours.

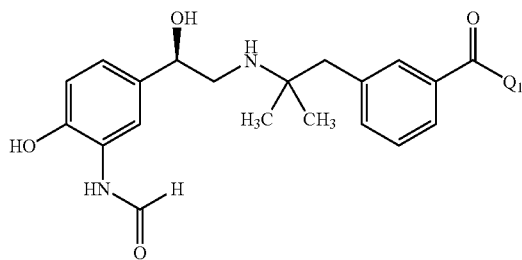

| No. | Q₁ | Data | Yield |
|---|---|---|---|
| 51 | ![HN-CH2CH2-(2,3-dimethylphenyl)] | ¹H NMR (400 MHz, CD₃OD) δ: 1.04 (3H, s), 1.12 (3H, s), 2.24 (6H, s), 2.69–3.01 (6H, m), 3.52–3.55 (2H, m), 4.62–4.66 (1H, m), 6.82–6.84 (1H, m), 6.95–7.10 (4H, m), 7.31–7.37 (2H, m), 7.60–7.70 (2H, m), 8.09 (1H, s), 8.28 (s), 8.63 (s); LRMS APCl m/z 504 [M + H]⁺ | 81% |
| 52 | ![HN-CH2CH2-(2-chlorophenyl)] | ¹H NMR (400 MHz, CD₃OD) δ: 1.04 (3H, s), 1.11 (3H, s), 2.69–2.96 (4H, m), 3.01–3.08 (2H, m), 3.61–3.66 (2H, m), 4.62–4.65 (1H, m), 6.82 (1H, d), 7.00–7.03 (1H, m), 7.16–7.21 (2H, m), 7.28–7.40 (4H, m), 7.61–7.65 (2H, m), 8.08 (1H, s), 8.28 (s), 8.63 (s); LRMS APCl m/z 510 [M + H]⁺ | 79% |
| 53 | ![HN-CH2CH2-(2,6-dimethylphenyl)] | ¹H NMR (400 MHz, CD₃OD) δ: 1.05 (3H, s), 1.13 (3H, s), 2.34 (6H, s), 2.71–2.79 (2H, m), 2.95–3.01 (4h, m), 3.43–3.49 (2H, m), 4.64–4.67 91H, m), 6.83 (1H, d), 6.95–6.97 (3H, m), 7.02–7.08 (1H, m), 7.33–7.41 (2H, m), 7.67–7.73 (2H, m), 8.12 (1H, s), 8.29 (s), 8.63 (s); LRMS APCl m/z 504 [M + H]⁺ | 96% |
| 54 | ![HN-CH2CH2-(4-methylphenyl)] | ¹H NMR (400 MHz, CD₃OD) δ: 1.04 (3H, s), 1.11 (3H, s), 2.27 (3H, s), 2.69–2.98 (6H, m), 3.54–3.60 (2H, m), 4.62–4.65 (1H, m), 6.82 (1H, d), 7.00–7.14 (5H, m), 7.30–7.38 (2H, m), 7.59–7.67 (2H, m), 8.08 (1H, s), 8.29 (s), 8.62 (s); LRMS APCl m/z 504 [M + H]⁺ | 86% |
| 55 | ![HN-CH2CH2-(1-naphthyl)] | ¹H NMR (400 MHz, CD₃OD) δ: 1.04 (3H, s), 1.12 (3H, s), 2.68–3.02 (4H, m), 3.62–3.97 (2H, m), 3.70–3.74 (2H, m), 4.64–4.68 (1H, m), 6.83 (1H, d), 7.02 (1H, d), 7.34–7.48 (6H, m), 7.62 (1H, s), 7.65–7.67 (1H, m), 7.72–7.76 (1H, m), 7.80–7.84 (1H, m), 8.18 (1H, s), 8.20 (1H, d), 8.29 (s), 8.62 (s); LRMS APCl m/z 526 [M + H]⁺ | 76% |

EXAMPLES 56

3-{(2R)-2-[(2R)-2-(3-Formylamino-4-hydroxyphenyl)-2-hydroxyethylamino]propyl}-N-[2-(4-hydroxyphenyl)-2-methylpropyl]benzamide

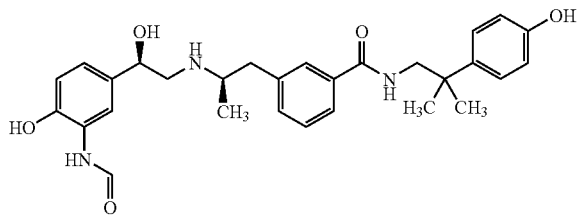

The title compound was prepared from the product of preparation 138, using a method similar to that of examples 38–50, as a brown glass (35 mg, 31%). $^1$H NMR (400 MHz, CD$_3$OD) δ: 1.03 (3H, d), 1.27 (6H, s), 2.56–2.90 (4H, m), 3.45 (2H, s), 4.55–4.58 (1H, m), 6.67–6.72 (3H, m), 6.85–6.87 (1H, m), 7.19–7.26 (5H, m), 7.38 (1H, s), 7.43 (1H, d), 7.91 (d), 8.21 (s), 8.51 (s); LRMS APCI m/z 506 [M+H]$^+$

EXAMPLE 57

N-{5-[(1R)-2-((1R)-2-{3-[3-(3,4-Dihydro-1H-isoquinolin-2-yl)-3-oxopropyl]phenyl}-1-methylethylamino)-1-hydroxyethyl]-2-hydroxyphenyl}formamide

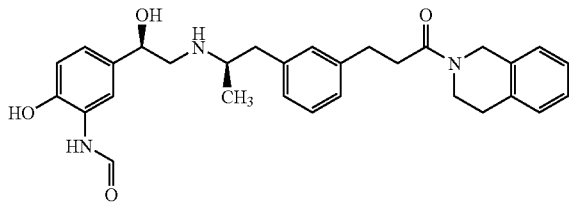

The title compound was prepared from the product of preparation 138, using a method similar to that of examples 38–50, as a brown glass (35 mg, 31%) $^1$H NMR (400 MHz, CD$_3$OD) δ: 1.00–1.05 (3H, m), 2.48–2.92 (11H, m), 3.59 (1H, t), 3.73 (1H, t), 4.54–4.65 (3H, m), 6.75–7.18 (10H, m), 7.97 (s), 8.28 (d), 8.56 (d); LRMS APCI m/z 502 [M+H]$^+$ The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-Pig Trachea

Male, Dunkin-Hartley guinea pigs (475–525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3–4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 µM Indomethacin (Sigma I7378), 10 µM Guanethidine (Sigma G8520) and 10 µM Atenolol (Sigma A7655), heated at 37° C. and gassed with 95% O$_2$/5% CO$_2$, before applying an initial tension of 1 g. The preparations are allowed to equilibrate for a further 30–45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma I5627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The EC$_{50}$ value for beta-2 agonist according to the present invention refers to the concentration of compound required to produce half maximal effect. Data for beta-2 agonists according to the present invention are then expressed as relative potency to isoprenaline defined by the ratio (EC$_{50}$ beta-2 agonist)/ (EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β2 antagonist) which results in the case of a beta-2 mediated effect in a rightward-shift of the test compound dose response curve.

According to another alternative, the agonist potency for the β2 receptor of the compounds of the formula (1) may also be determined by the measure of the concentration of compound according to the present invention required to produce half maximal effect (EC$_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46–50, 1987 and Bouvier et al., Mol Pharmacol 33: 133–139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040-174) and resuspended in stimulation buffer (NEN, SMP004B) to give $1\times10^6$ cells/ml CHOhB2. Compounds were incubated with 50 µl/well cells for 1 hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the compounds of formula (1) according to the present invention that are illustrated in examples 1 to 57 above show a β2 cAMP $EC_{50}$ below 5 nM.

The invention claimed is:

1. A compound of formula (1),

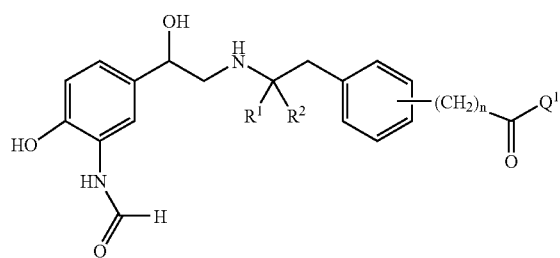
(1)

or a pharmaceutically acceptable salt thereof,
wherein the $(CH_2)_n$—C(=O)$Q^1$ group is in the meta or para position;
$R^1$ and $R^2$ are independently H or $C_1$–$C_4$ alkyl;
n is 0, 1 or 2;
$Q^1$ is

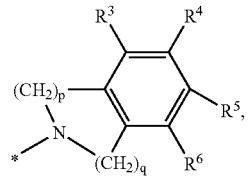

said group being optionally bridged by one carbon atom;

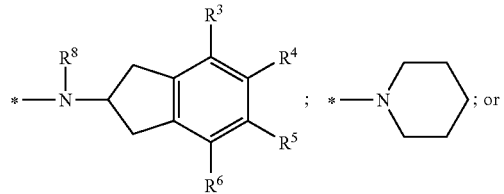

*—$NR^8$—$Q^2$—A;
p is 1 or 2;
q is 1 or 2;
$Q^2$ is $C_1$–$C_4$ alkylene;
$R^8$ is H or $C_1$–$C_4$ alkyl;
A is pyridyl; $C_3$–$C_{10}$ cycloalkyl, 2 or 3 carbon atoms of said cycloalkyl being optionally bridged by 1, 2, 3 or 4 $C_1$–$C_4$ alkyl, said alkylene bridge being optionally branched; tetrahydropyranyl; piperidinyl; tetrahydrothiopyranyl;

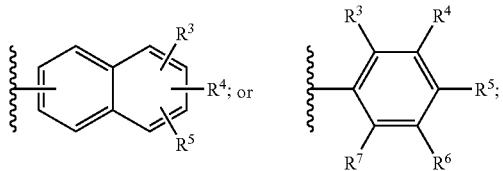

$R^3$, $R^4$, $R^5$, $R^6$ and $R^7$ are independently H, $C_1$–$C_4$ alkyl, $OR^9$, $SR^9$, $SOR^9$, $SO_2R^9$, halo, $CO_2R^9$, $CF_3$, CN, $OCF_3$, $SO_2NR^9R^{10}$, $CONR^9R^{10}$, $NR^9R^{10}$, $NHCOR^{10}$ or phenyl optionally substituted with 1 to 3 $OR^9$, halo or $C_1$–$C_4$ alkyl;
$R^9$ and $R^{10}$ are independently H or $C_1$–$C_4$ alkyl; and
the * represents the attachment point to the carbonyl group.

2. A compound of claim 1 or a pharmaceutically acceptable salt thereof wherein $Q^1$ is *—NH-$Q^2$-A; and A is cyclohexyl or adamantyl.

3. A compound of claim 1 or a pharmaceutically acceptable salt thereof wherein $Q^1$ is *—NH-$Q^2$-A; and A is

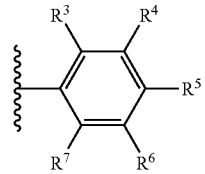

provided at least 2 of $R^3$ to $R^7$ are equal to H.

4. A compound of claim 3 or a pharmaceutically acceptable salt thereof wherein $Q^1$ is *—NH-$Q^2$-A; and A is

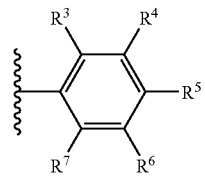

wherein $R^3$, $R^4$, $R^5$, $R^6$ and $R^7$ are independently H, OH, $CH_3$, $OCH_3$, $OCF_3$, $OCH_2$—$CH_3$, $SCH_3$, $N(CH_3)_2$, N(C=O)CH₃, C(=O)NH₂, COOCH₃, SO₂CH₃, SO₂NH₂, CN, halo, CF₃ or phenyl optionally substituted with OH.

5. A compound of claim 1 or a pharmaceutically acceptable salt thereof wherein A is

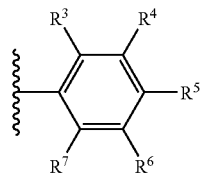

wherein one of $R^3$ to $R^7$ is OH or phenyl substituted with OH.

6. A compound of claim 1 or a pharmaceutically acceptable salt thereof wherein A is naphthyl optionally susbstituted with OH.

7. A compound of claim 1 or a pharmaceutically acceptable salt thereof wherein $Q^2$ is —CH₂—, —(CH₂)₂—, —(CH₂)₃—, —CH₂—C(CH₃)₂— or —C(CH₃)₂—.

8. A compound of claim 7 or a pharmaceutically acceptable salt thereof wherein $Q^2$ is —CH₂—.

9. A compound of claim 1 or a pharmaceutically acceptable salt thereof wherein $Q^1$ is

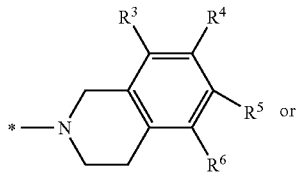 or

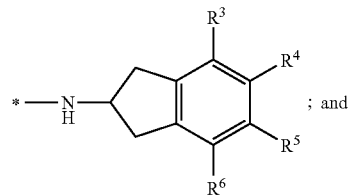 ; and $R_3$, $R_4$, $R_5$ and $R_6$ are H.

10. A compound of claim 1 or a pharmaceutically acceptable salt thereof wherein $R^1$ is H or $C_1$–$C_4$ alkyl and $R^2$ is $C_1$–$C_4$ alkyl.

11. A compound of claim 10 or a pharmaceutically acceptable salt thereof wherein $R^1$ is H or CH₃ and $R^2$ is H or CH₃.

12. A compound of claim 1 or a pharmaceutically acceptable salt thereof wherein n is 0 or 1.

13. The (R,R)-stereoisomer of a compound of claim 1 or a pharmaceutically acceptable salt thereof.

14. A compound of claim 1 or a pharmaceutically acceptable salt thereof wherein the (CH₂)ₙ—C(=O)Q¹ group is in the meta position.

15. A pharmaceutical composition comprising an effective amount of a compound of claim 1 or a pharmaceutically acceptable salt thereof and a pharmaceutically acceptable exipient or additive.

* * * * *